United States Patent
Lee et al.

(10) Patent No.: US 10,897,013 B2
(45) Date of Patent: Jan. 19, 2021

(54) COMPOUND FOR ORGANIC ELECTRIC DEVICE, ORGANIC ELECTRIC DEVICE USING SAME, AND ELECTRONIC DEVICE COMPRISING SAME

(71) Applicant: DUK SAN NEOLUX CO., LTD., Cheonan-si (KR)

(72) Inventors: Mun Jae Lee, Cheonan-si (KR); Bum Sung Lee, Hwaseong-si (KR); Sun Hee Lee, Hwaseong-si (KR); Soung Yun Mun, Cheonan-si (KR); Dae Sung Kim, Yongin-si (KR); Jae Taek Kwon, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 347 days.

(21) Appl. No.: 15/763,027

(22) PCT Filed: Sep. 12, 2016

(86) PCT No.: PCT/KR2016/010248
§ 371 (c)(1),
(2) Date: Mar. 23, 2018

(87) PCT Pub. No.: WO2017/052129
PCT Pub. Date: Mar. 30, 2017

(65) Prior Publication Data
US 2019/0058129 A1     Feb. 21, 2019

(30) Foreign Application Priority Data
Sep. 25, 2015 (KR) .................. 10-2015-0136175

(51) Int. Cl.
| | | |
|---|---|---|
| H01L 51/00 | (2006.01) | |
| C09K 11/06 | (2006.01) | |
| C07C 209/10 | (2006.01) | |
| C07C 211/61 | (2006.01) | |
| C07D 307/77 | (2006.01) | |
| C07D 307/91 | (2006.01) | |
| H01L 51/50 | (2006.01) | |
| C07D 209/88 | (2006.01) | |

(52) U.S. Cl.
CPC ........ *H01L 51/0061* (2013.01); *C07C 209/10* (2013.01); *C07C 211/61* (2013.01); *C07D 307/77* (2013.01); *C09K 11/06* (2013.01); *H01L 51/0003* (2013.01); *H01L 51/006* (2013.01); *H01L 51/0052* (2013.01); *H01L 51/0058* (2013.01); *H01L 51/0059* (2013.01); *H01L 51/0067* (2013.01); *H01L 51/0072* (2013.01); *H01L 51/0073* (2013.01); *H01L 51/0074* (2013.01); *C07C 2603/18* (2017.05); *C07C 2603/97* (2017.05); *C07D 209/88* (2013.01); *C07D 307/91* (2013.01); *C09K 2211/1007* (2013.01); *C09K 2211/1011* (2013.01); *C09K 2211/1014* (2013.01); *C09K 2211/1018* (2013.01); *H01L 51/0056* (2013.01); *H01L 51/5012* (2013.01); *H01L 51/5056* (2013.01); *H01L 51/5064* (2013.01); *H01L 51/5096* (2013.01)

(58) Field of Classification Search
CPC ............ H01L 51/0061; H01L 51/0059; H01L 51/0003; H01L 51/0067; H01L 51/0074; H01L 51/0052; H01L 51/0058; H01L 51/006; H01L 51/0072; H01L 51/0073; H01L 51/5064; H01L 51/0056; H01L 51/5012; H01L 51/5056; H01L 51/5096; C07C 209/10; C07C 211/61; C07C 2603/97; C07C 2603/18; C07D 307/77; C07D 307/91; C07D 209/88; C09K 11/06; C09K 2211/1007; C09K 2211/1011; C09K 2211/1014; C09K 2211/1018
See application file for complete search history.

(56) References Cited

U.S. PATENT DOCUMENTS

| | | | | |
|---|---|---|---|---|
| 2013/0207046 A1* | 8/2013 | Pflumm | .............. | H01L 51/0058 252/500 |
| 2014/0231774 A1* | 8/2014 | Huh | ........................ | C09B 57/00 257/40 |

FOREIGN PATENT DOCUMENTS

| | | |
|---|---|---|
| JP | 2009-200493 A | 9/2009 |
| KR | 10-2013-0028673 A | 3/2012 |
| KR | 10-2013-0099098 A | 9/2013 |
| KR | 10-1379133 B1 | 3/2014 |
| KR | 10-2015-0058396 A | 5/2015 |

OTHER PUBLICATIONS

Park, S.J., et al.; Optics Express, 2014, p. 12392-12397.*
Ma, J., et al.; Electronics and Signal Processing, 2011, p. 541-546.*

* cited by examiner

*Primary Examiner* — Robert S Jones, Jr.
(74) *Attorney, Agent, or Firm* — Vorys, Sater, Seymour & Pease LLP; Mih Suhn Koh

(57) ABSTRACT

Provided is an organic electric element including an electron blocking layer and a hole transport layer capable of improving the luminous efficiency, stability, and lifetime of the organic electric element, and an electronic device including the same.

14 Claims, 1 Drawing Sheet

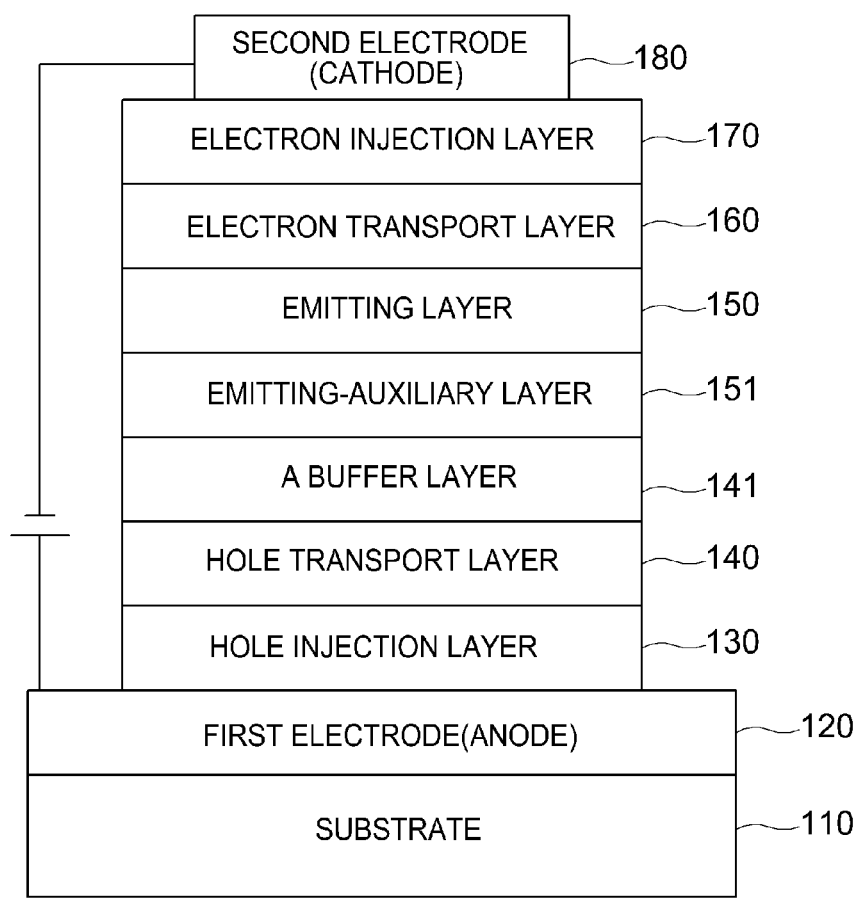

COMPOUND FOR ORGANIC ELECTRIC DEVICE, ORGANIC ELECTRIC DEVICE USING SAME, AND ELECTRONIC DEVICE COMPRISING SAME

BACKGROUND

Technical Field

The present invention relates to compound for organic electric element, organic electric element using the same, and an electronic device thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

In the organic electroluminescent device, the most problematic is the lifetime and the efficiency. As the display becomes large, the efficiency and the lifetime problem must be solved.

Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase.

However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, recently, in organic electroluminescent devices, in order to solve the emission problem in the a hole transport layer, an electron blocking layer must be present between the hole transport layer and an emitting layer, and it is necessary to develop an electron blocking layer commonly used for each of the emitting layers (R, G, B)

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value. As a result, the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic device are lowered and the life span is shortened. Therefore, it is urgently required to develop an electron blocking layer having a high T 1 value and a HOMO level between the HOMO energy level of the hole transport layer and the HOMO energy level of the emitting layer.

That is, in order to sufficiently exhibit the excellent characteristics of the organic electric element, a material for forming an organic material layer in an element such as a hole injection material, a hole transport material, a light emitting material, an electron transport material, an electron injection material, an electron blocking layer material should be supported by stable and efficient materials. However, such a stable and efficient organic material layer material for an organic electric element has not been sufficiently developed yet. Therefore, development of new materials is continuously required, and development of materials for the electron blocking layer and the hole transport layer is urgently required.

DETAILED DESCRIPTION OF THE INVENTION

Summary

The present invention provides an organic electric element having improved driving voltage, device efficiency and lifetime by increasing the charge balance in an emitting layer by optimal combination of a novel compound for an electron blocking layer and a compound for a hole transport layer and an electronic device using the same.

Technical Solution

The present invention provides an organic electronic device and an electronic device in which a compound represented by Formula (1) is comprised in an electron blocking layer and a compound represented by Formula (2) is comprised in a hole transport layer.

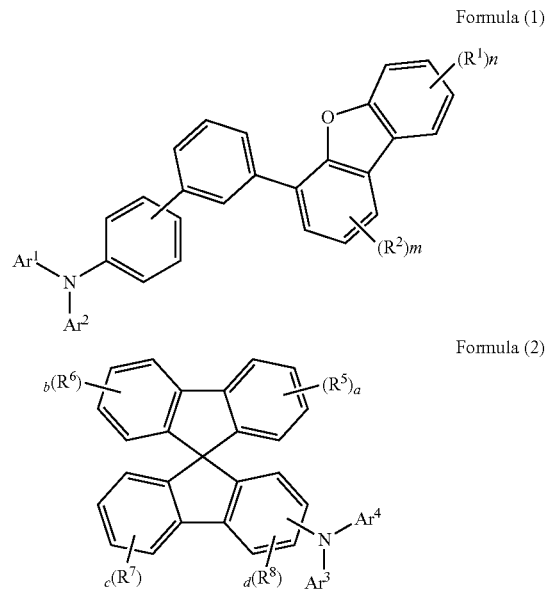

Formula (1)

Formula (2)

Effects of the Invention

By using the laminate including the electron blocking layer and the hole transport layer according to the present invention, deterioration of the interface of the emitting layer can be prevented, and by increasing the charge balance in the emitting layer, it is possible to greatly improve the high luminous efficiency, low driving voltage, high color purity and lifetime.

BRIEF DESCRIPTION OF THE DRAWINGS

The FIGURE is an illustration of an organic electroluminescent device according to the present invention.

| | |
|---|---|
| 100: organic electric element, | 110: substrate |
| 120: the first electrode(anode), | 130: the hole injection layer |
| 140: the hole transport layer, | 141: a buffer layer |
| 150: the emitting layer, | 151: the emitting auxiliary layer |
| 160: the electron transport layer, | 170: the electron injection layer |
| 180: the second electrode(cathode) | |

DETAILED DESCRIPTION

Hereinafter, some embodiments of the present invention will be described in detail with reference to the accompanying drawings, It is to be noted that, in adding reference numerals to the constituent elements of the drawings, the same constituent elements are denoted by the same reference numerals whenever possible, even if they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component. Also, when an element such as a layer, film, region, plate, or the like is referred to as being "over" or "on" another element, it should be understood that this may include not only the case "directly above" another element but also the case where there is another element in between. On the contrary, when an element is referred to as being "directly on" another element, it should be understood that there is no other element in between.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "fluorenyl group" or "fluorenylene group", as used herein, means a monovalent or divalent functional group in which, in the following structures, R, R' and R" are both hydrogen, and "substituted fluorenyl group" or "substituted fluorenylene group" means that at least one of substituents R, R', R" is a substituent other than hydrogen, and R and R' are bonded to each other to form a spiro compound together with the carbon to which they are bonded.

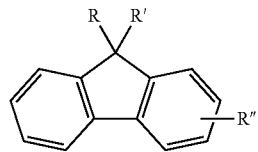

Unless otherwise stated, the term "aryl group" or "arylene group", as used herein, has 6 to 60 carbon atoms, but is not limited thereto. In the present invention, the aryl group or the arylene group includes a single ring type, a ring bonding group, a plurality of bonded ring systems, a spiro compound, and the like.

The term "heterocyclic group", as used herein, includes not only aromatic rings such as "heteroaryl groups" or "heteroarylene groups" but also nonaromatic rings and, unless otherwise stated, means a ring a C2 to C60 aryl containing one or more of hetero atoms or arylene group, but is not limited thereto. Unless otherwise stated, the term "heteroatom", as used herein, represents at least one of N, O, S, P, or Si, and the heterocyclic group means a single ring including a hetero atom, a ring junction, a plurality of ring systems bonded together, a spiro compound, and the like.

Also, the term "heterocyclic group" may include a ring containing $SO_2$ instead of carbon consisting of cycle. For example, "heterocyclic group" includes compound below.

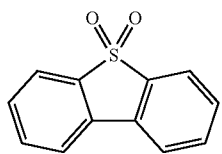 [SMILES: O=S1(=O)c2ccccc2-c2ccccc21]

The term "ring", as used herein, includes monocyclic and polycyclic rings, and includes not only hydrocarbon rings but also heterocycles containing at least one heteroatom, including aromatic and non-aromatic rings.

The term "polycyclic", as used herein, includes ring assemblies such as biphenyl, terphenyl, and the like, fused multiple ring systems and spiro compounds, and includes not only aromatic but also non-aromatic, and includes a heterocycle including at least one heteroatom as well as a hydrocarbon ring.

The term "ring assemblies", as used herein, means that two or more ring systems (a single ring or a fused ring system) are directly linked to each other through a single bond or a double bond and that the number of direct connections between such rings is one less than the total number of rings in the compound. The ring assemblies may be directly linked to each other through a single bond or a double bond of the same or different ring systems.

The term "fused ring system", as used herein, means a fused ring form sharing at least two atoms, and includes a form in which two or more hydrocarbons ring system is fused, and a form in which at least one heterocyclic system containing at least one hetero atom is fused. These fused multiple ring systems may be aromatic rings, heteroaromatic rings, aliphatic rings or a combination of these rings.

The term "spiro compound", as used herein, has a "spiro union", and the spiro union means a link consisting of two rings sharing only one atom. At this time, atoms shared in the two rings are referred to as 'spiro atoms' and these compounds are called 'monospiro-', 'di-spiro-', and 'tri-spiro' compounds, depending on the number of atoms in a compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

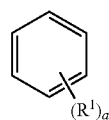

wherein, when a is an integer of zero, the substituent $R^1$ is absent, when a is an integer of 1, the sole substituent $R^1$ is linked to any one of the carbon constituting the benzene ring, when a is an integer of 2 or 3, they are respectively bonded as follows, in which $R^1$ may be the same as or different from each other, when a is an integer of 4 to 6, it bonds to the carbon of the benzene ring in a similar manner, and the indication of the hydrogen bonded to the carbon forming the benzene ring is omitted.

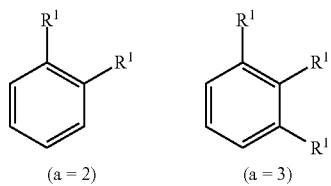

The FIGURE is an illustration of an organic electric element according to an embodiment of the present invention.

Referring to the FIGURE, the organic electric element (100) according to the present invention includes a first electrode(120) formed on a substrate(110), a second electrode(180), and an organic material layer between the first electrode(120) and the second electrode(180), which contains the compound represented by Formula 1. Here, the first electrode(120) may be an anode (positive electrode), and the second electrode(180) may be a cathode (negative electrode). In the case of an inverted organic electric element, the first electrode may be a cathode, and the second electrode may be an anode.

The organic material layer may include a hole injection layer(130), a hole transport layer(140), an emitting layer (150), an electron transport layer(160), and an electron injection layer(170) formed in sequence on the first electrode(120). Here, at least one of these layers may be omitted, or a hole blocking layer, an electron blocking layer, an emitting-auxiliary layer(151), a buffer layer(141), etc. may be further included, and the electron transport layer(160) and the like may serve as a hole blocking layer.

Although not shown, the organic electric element according to the present invention may further include a protective layer or a Capping layer formed on at least one side of the first and second electrodes, which is a side opposite to the organic material layer.

The organic electroluminescent device according to an embodiment of the present invention may be manufactured using various deposition methods. It can be manufactured using a deposition method such as PVD or CVD, for example, the organic electric element may be manufactured by depositing a metal or a conductive metal oxide or a mixture thereof on the substrate(110) to form the anode (120), and thereon forming the organic material layer including the hole injection layer(130), the hole transport layer (140), the emitting layer(150), the electron transport layer (160), and the electron injection layer(170), and then thereon, depositing a material, which can be used as the cathode(180). Further, an emitting-auxiliary layer (151) or an electron blocking layer may be additionally formed between the hole transport layer(140) and the emitting layer(150).

In addition, the organic material layer can be fabricated into a smaller number of layers by using various polymer materials in a solution process or a solvent process such as a spin coating process, a nozzle printing process, an inkjet printing process, a slot coating process, a dip coating process or a roll-to-roll process, a doctor blading process, a screen printing process or heat transfer method etc. Since the organic material layer according to the present invention can be formed by various methods, the scope of the present invention is not limited by the method of forming the organic material layer.

The organic electric element according to an embodiment of the present invention may be a front emission type, a back emission type, or a both-sided emission type, depending on the material used. WOLED (White Organic Light Emitting Device) has advantages of high resolution realization and excellent fairness, and can be manufactured using conventional LCD color filter technology. Various structures for a white organic light emitting device mainly used as a backlight device have been proposed and patented. Representatively, there are side-by-side arrangement of the emitting part of the red (R), green (G) and blue (B), a stacking method in which R, G, and B emitting layers are laminated on top and bottom, electroluminescence by the blue (B) organic emitting layer and, by using the light from this, a color conversion material (CCM) method using a photo-luminescence of an inorganic phosphor, etc., and the present invention may be applied to such WOLED.

The organic electric element according to the present invention may be one of an OLED, an organic solar cell, an organic photo conductor, an organic transistor and an element for monochromic or white illumination.

Another embodiment of the present invention may include a display device including the above-described organic electric element of the present invention and an electronic device including a control unit for driving the display device. Here, the electronic device may be a wired/wireless communication terminal which is currently used or will be used in the future, and covers all kinds of electronic devices including a mobile communication terminal such as a cellular phone, a personal digital assistant(PDA), an electronic dictionary, a point-to-multipoint (PMP), a remote controller, a navigation unit, a game player, various kinds of TVs, and various kinds of computers.

Hereinafter, the compound according to one aspect of the present invention will be described.

The present invention provides an organic electric element comprising a first electrode, a second electrode, and an organic material layer formed between the first electrode and the second electrode, wherein the organic material layer forms a hole transport layer between the first electrode and the emitting layer, and includes an electron blocking layer between the hole transport layer and the emitting layer, wherein the electron blocking layer comprises a compound represented by Formula (1), and wherein the hole transport layer comprises a compound represented by Formula (2).

Formula (1)

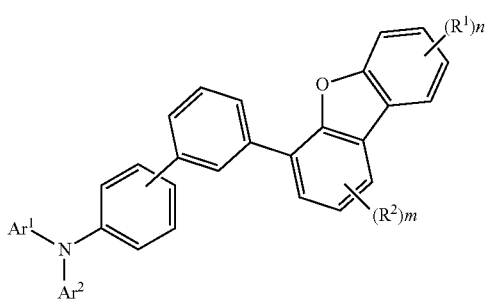

-continued

Formula (2)

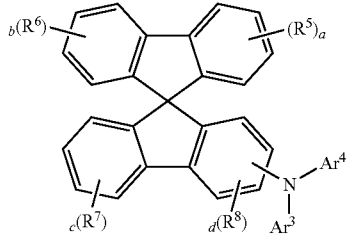

{In Formula (1) to (2), 1) n is an integer of 0 to 4, and m is an integer of 0 to 3, 2) $R^1$ and $R^2$ are each independently selected from a deuterium; a halogen; the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$)(where, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and the $R_a$ and $R_b$ may be independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P), or in case m, n, are 2 or more, and are each in plural and are the same or different, and a plurality of $R^1$ or a plurality of $R^2$ may be bonded to each other to form a ring, 3) $Ar^1$ and $Ar^2$ are each independently a $C_{12}$-$C_{20}$ aryl group unsubstituted or substituted with deuterium, 4) a, b, and c are each independently integer of 0 to 4, and d is an integer of 0 to 3, 5) $R^5$, $R^6$, $R^7$ and $R^8$ are each independently selected from a deuterium; a halogen; the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or in case a, b, c, d, e and f are 2 or more, and are each in plural and are the same or different, and a plurality of $R^5$ or a plurality of $R^6$ or a plurality of $R^7$ or a plurality of $R^8$ may be bonded to each other to form a ring, 6) $Ar^3$ and $Ar^4$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring;

In Formula (2), the aryl group, the fluorenyl group, the heterocyclic group, the fused ring group, the alkyl group, the alkenyl group, the alkynyl group, the alkoxyl group and the aryloxy group may be each independently substituted with one or more substituents selected from a group consisting of a deuterium; halogen; a silane group; a siloxane group; a boron group; a germanium group; a cyano; a nitro group; -L'-N($R_a$)($R_b$); a $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, and also, these substituents may combine each other and form a ring, wherein the term 'ring' means $C_3$-$C_{60}$ aliphatic ring or $C_6$-$C_{60}$ aromatic ring or a $C_2$-$C_{60}$ heterocyclic ring or a fused ring formed by the combination of them, and includes a saturated or unsaturated ring.}

More specially, the electron blocking layer provides an organic electric element wherein the compound represented by Formula (1) is represented by any one of the following Formulas (3) to (5).

<Formula (3)>

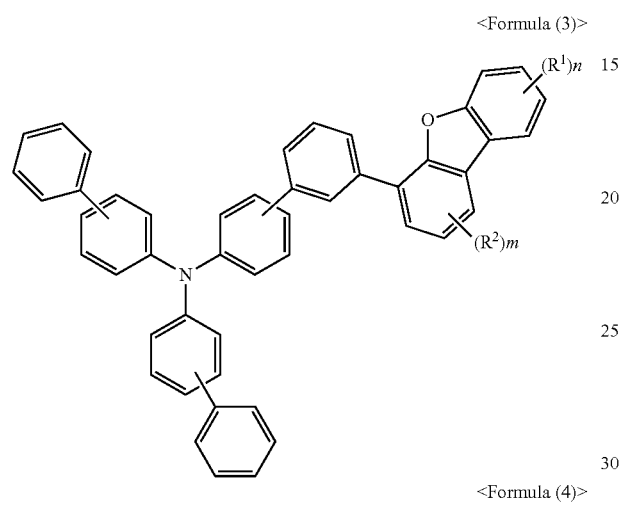

<Formula (4)>

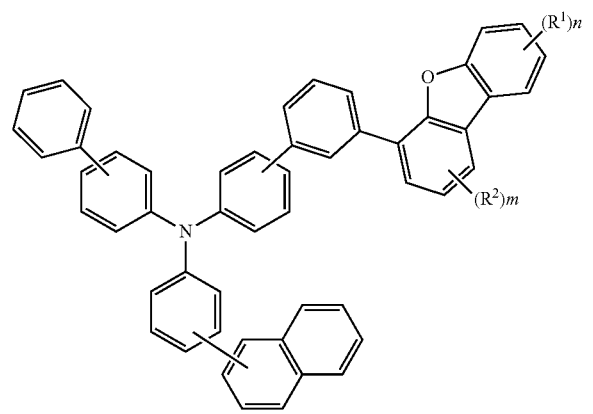

<Formula (5)>

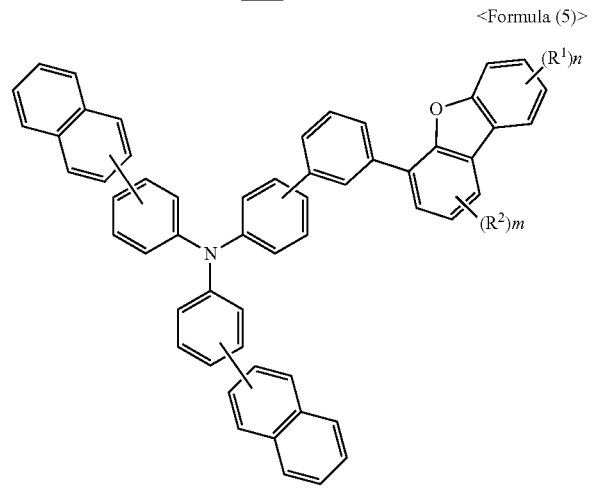

{In Formulas (3) to (5),

1) $R^1$, $R^2$, m and n are the same as defined above.}

Also, the hole transport layer of the present invention provides an organic electric element wherein the compound represented by Formula (2) is represented by any one of the following Formulas (6) to (8).

<Formula (6)>

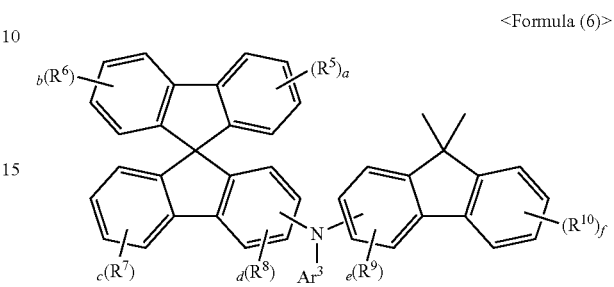

<Formula (7)>

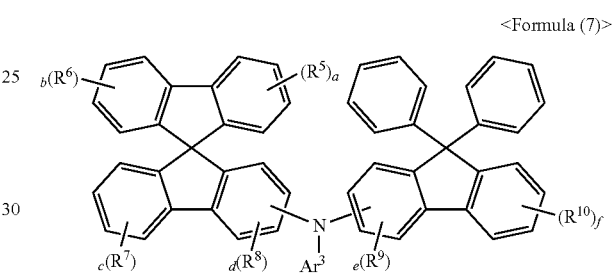

<Formula (8)>

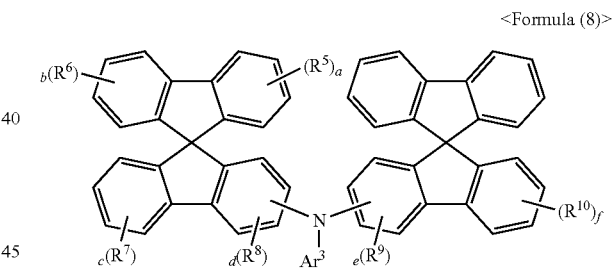

{In Formulas (6) to (8),

1) $R^5$, $R^6$, $R^7$, $R^8$, a, b, c, d and $Ar^3$ are the same as defined above, 2) f is an integer of 0 to 4, and e is an integer of 0 to 3, $R^9$ and $R^{10}$ are each independently selected from a deuterium; halogen; a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$), or in case e and f are 2 or more, and are each in plural and are the same or different, and a plurality of $R^9$ or a plurality of $R^{10}$ may be bonded to each other to form a ring}

As a specific example of the organic electric element provided by the present invention, the electron blocking layer provides an organic electric element wherein the compound represented by Formula (1) is any one of the following compounds 1-1 to 3-12.

1-1
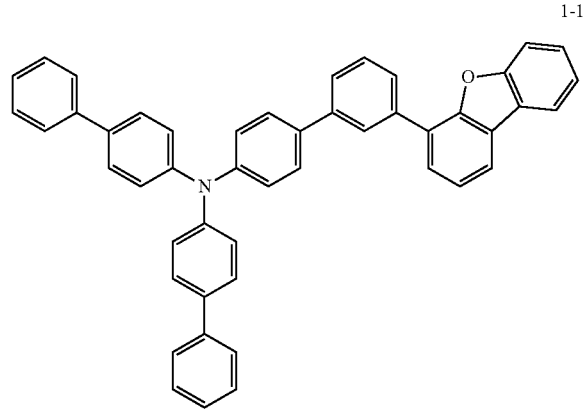
1-2
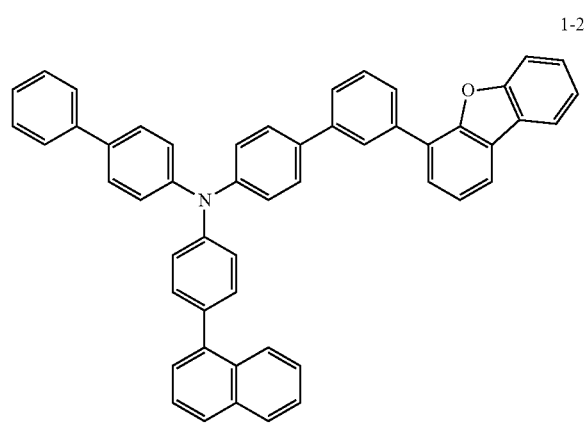
1-3
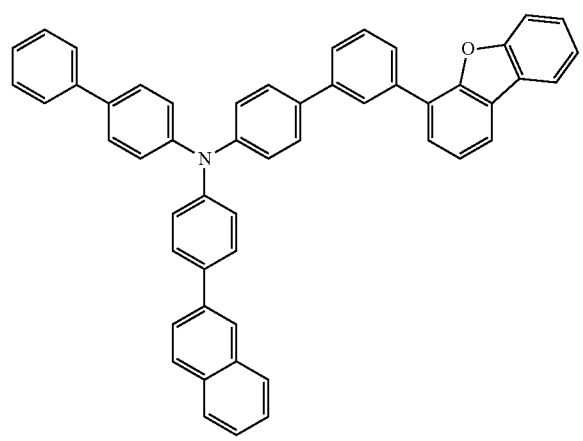
1-4
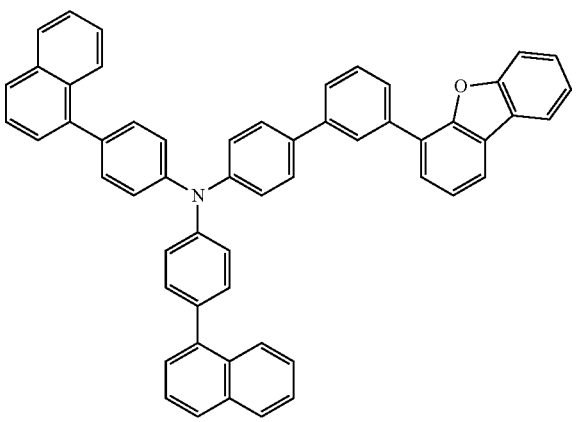
1-5
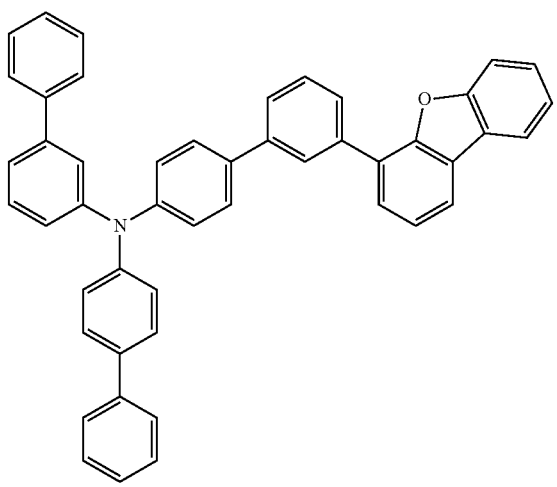
1-6
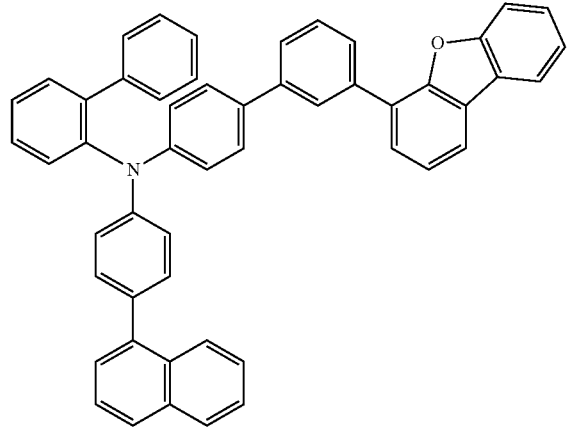

1-7
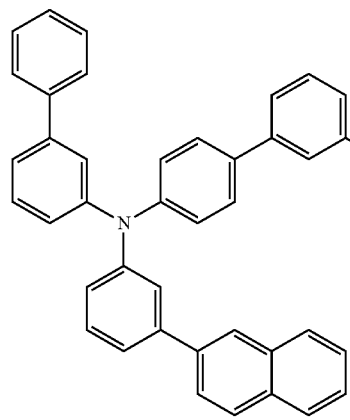
1-8
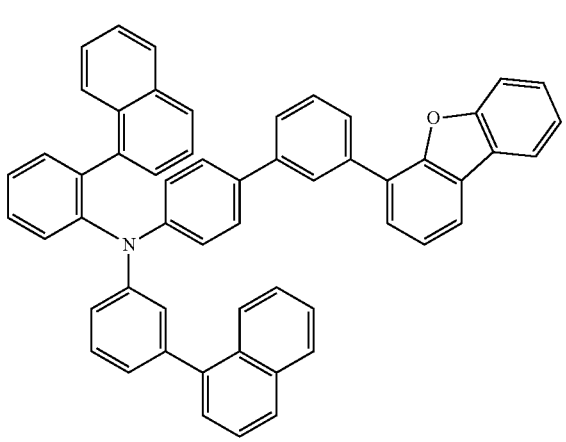
1-9
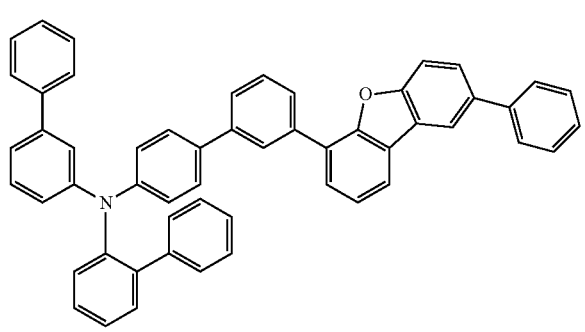
1-10
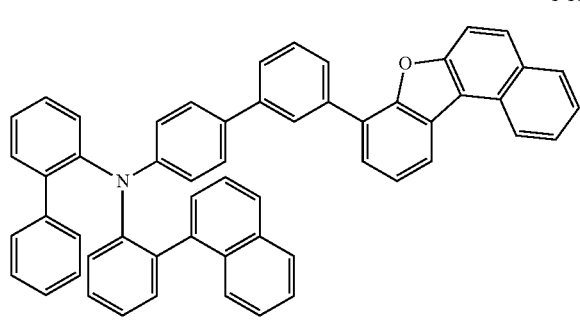
1-11
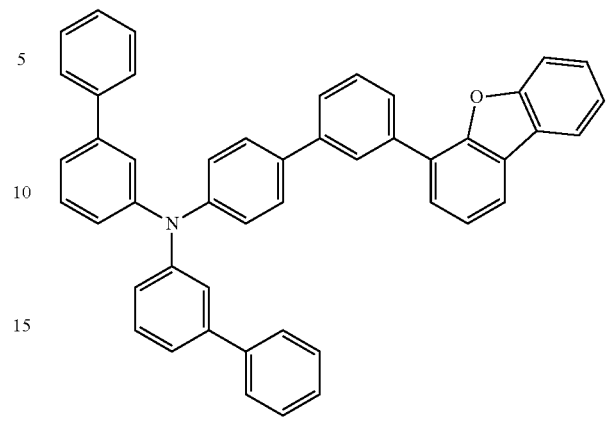
1-12
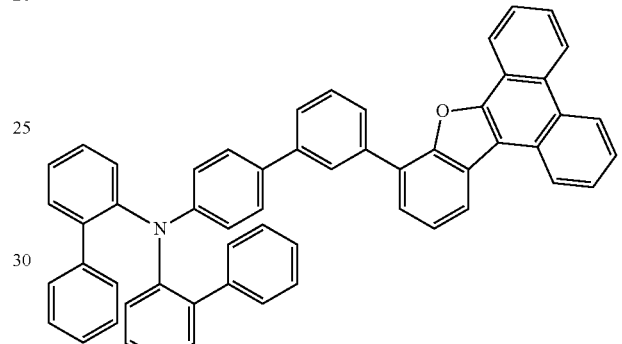
2-1
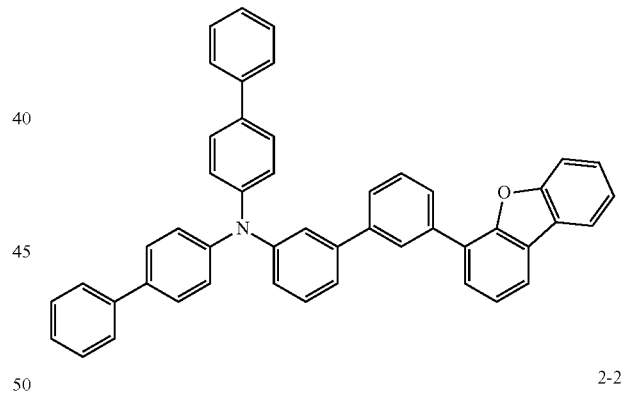
2-2
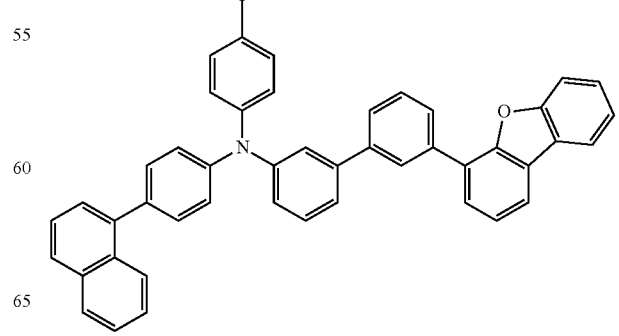

2-3
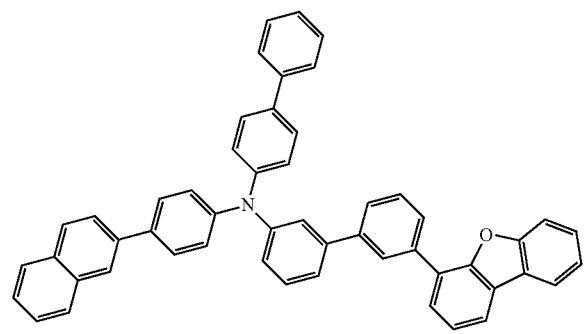
2-4
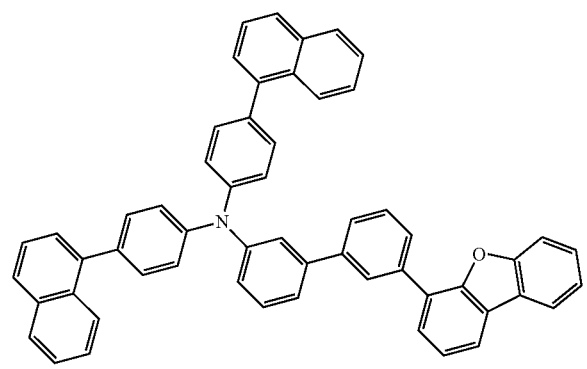
2-5
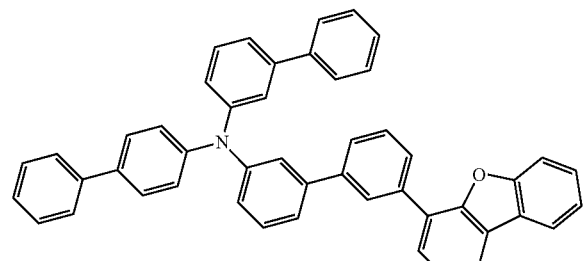
2-6
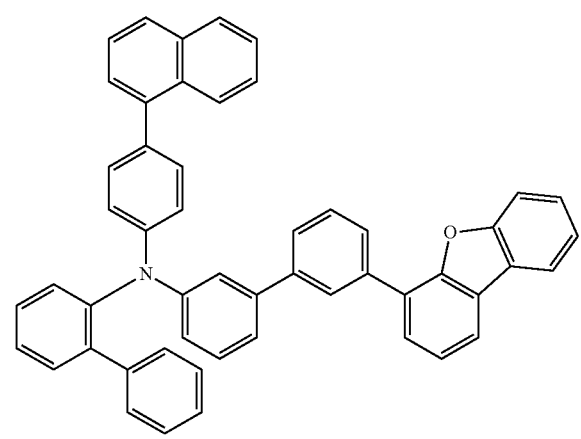
2-7
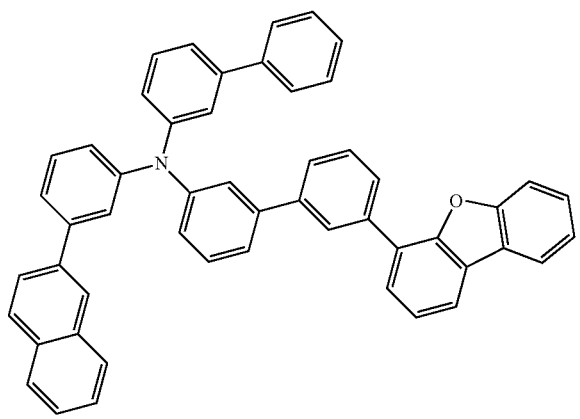
2-8
2-9
2-10
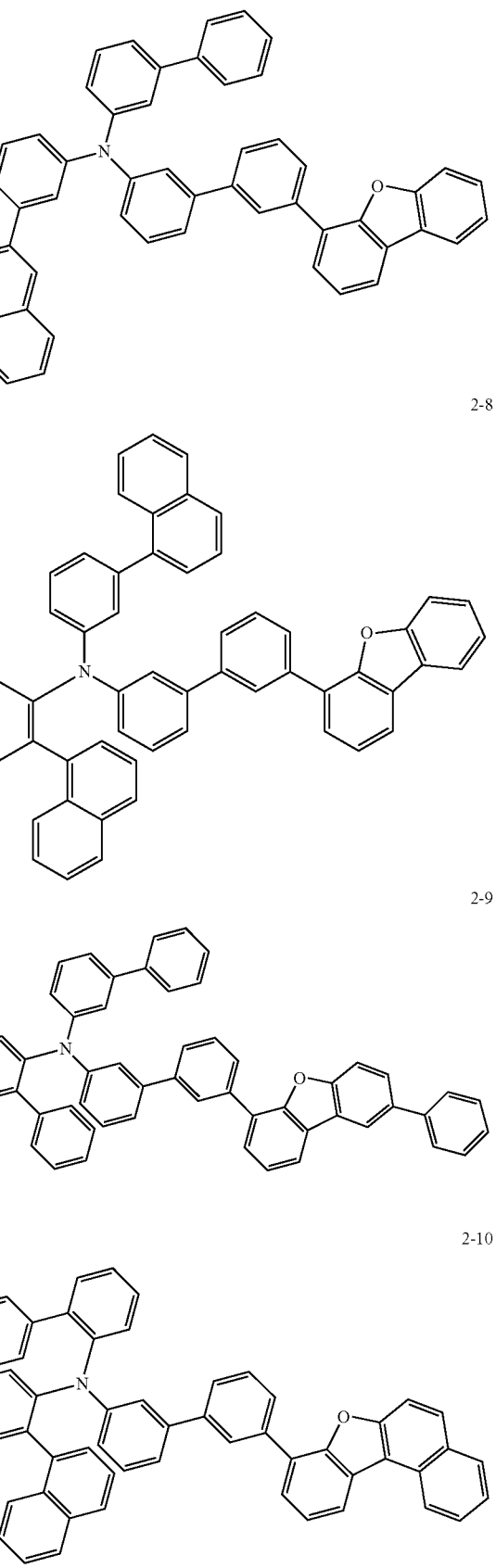

2-11
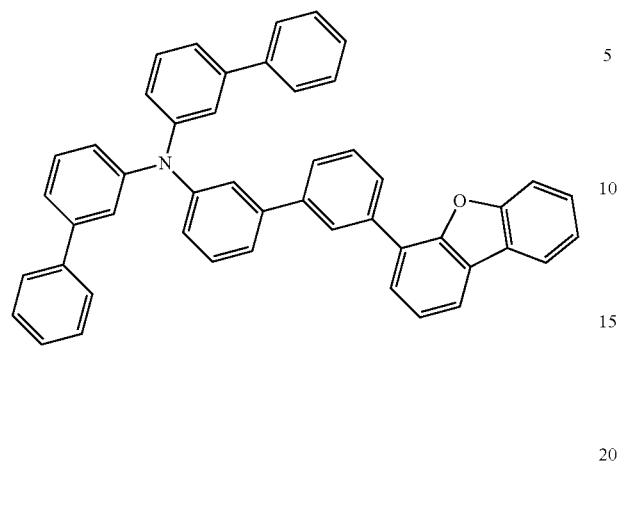
3-2
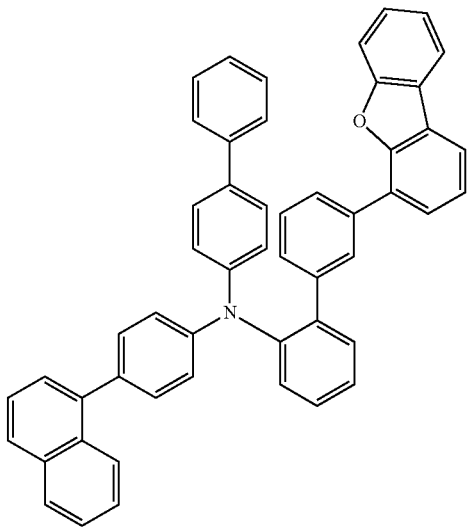
2-12
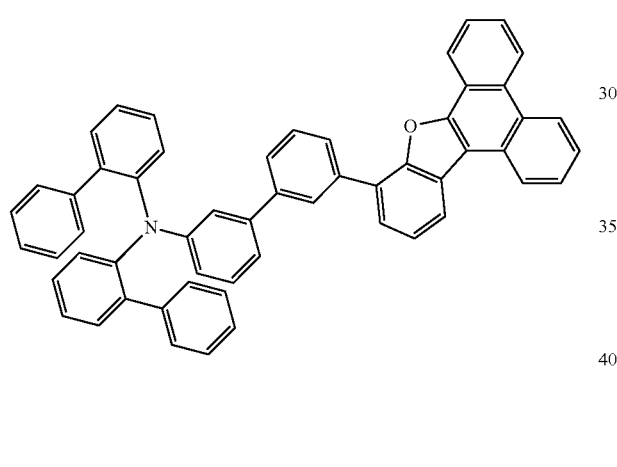
3-3
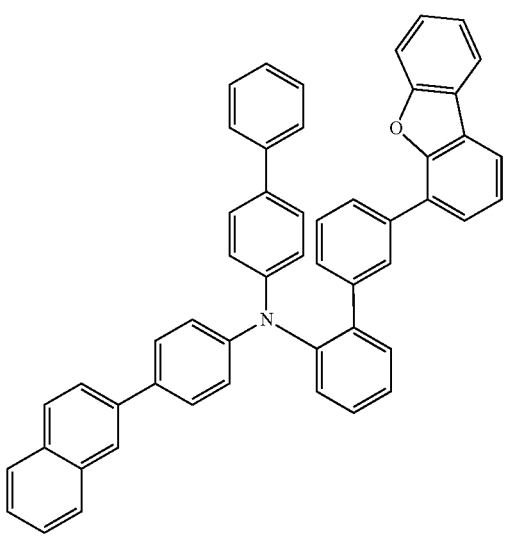
3-1
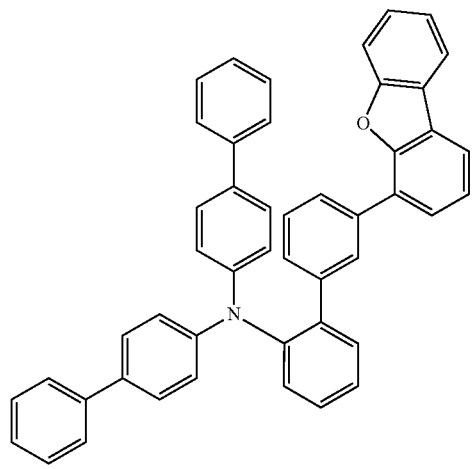
3-4
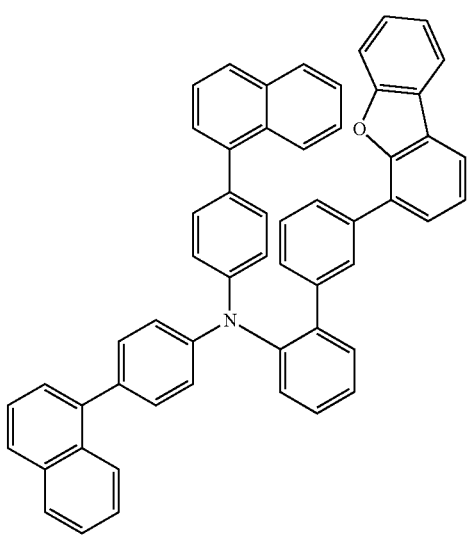

3-5
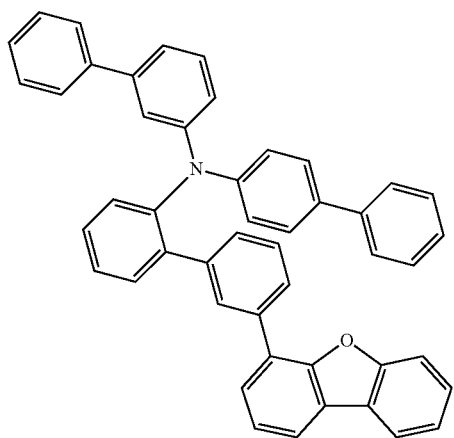
3-6
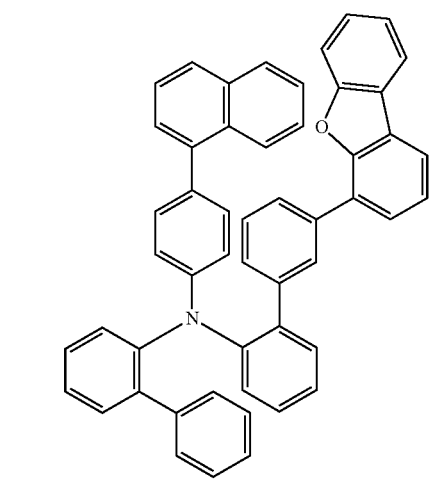
3-7
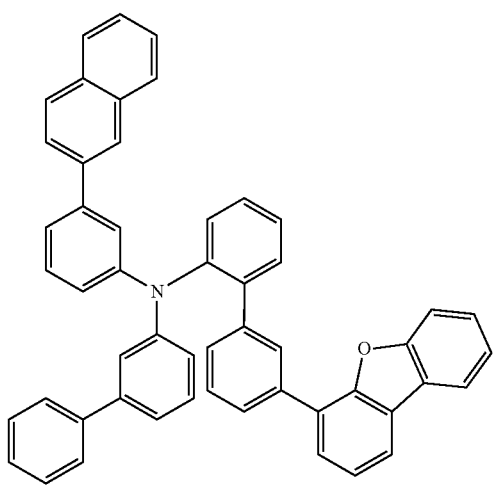
3-8
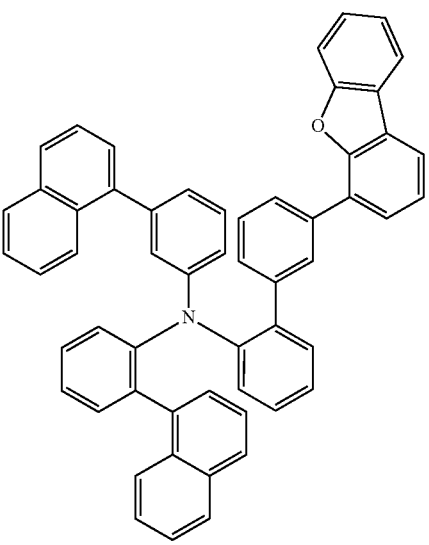
3-9
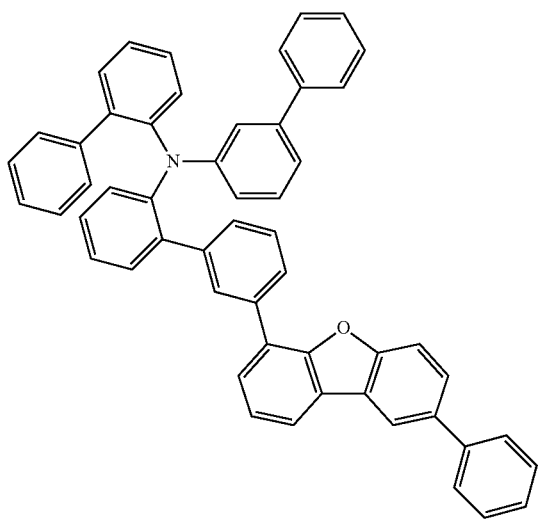
3-10
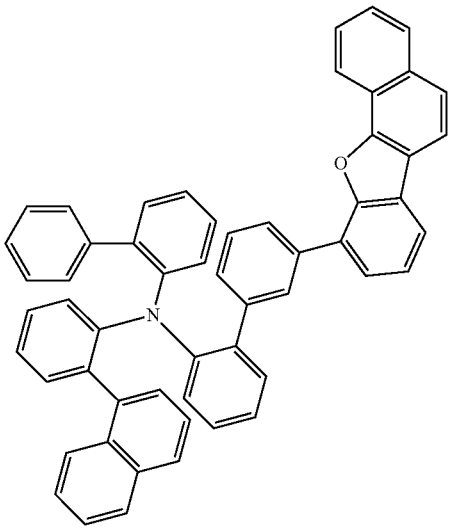

3-11
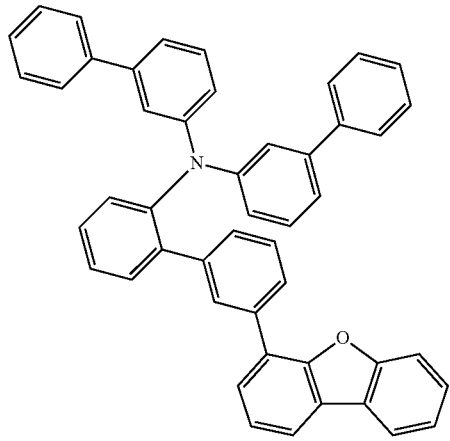
3-12
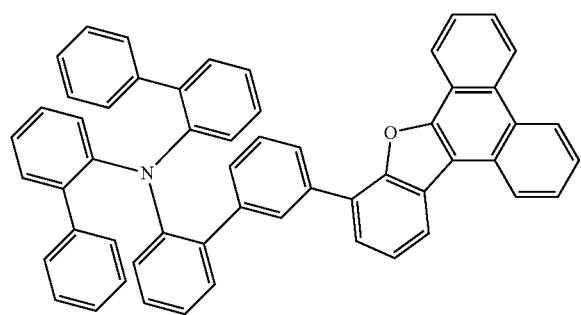
Also, the hole transport layer provides an organic electric element wherein the compound represented by Formula (2) is any one of the following compounds 4-1 to 4-36.
4-1
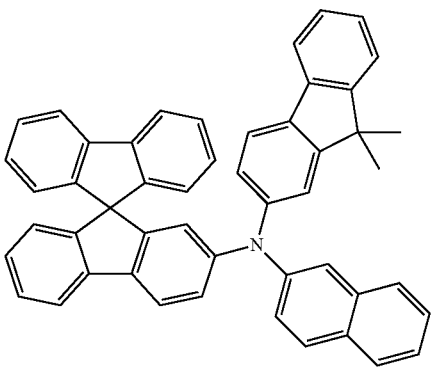
4-2
4-3
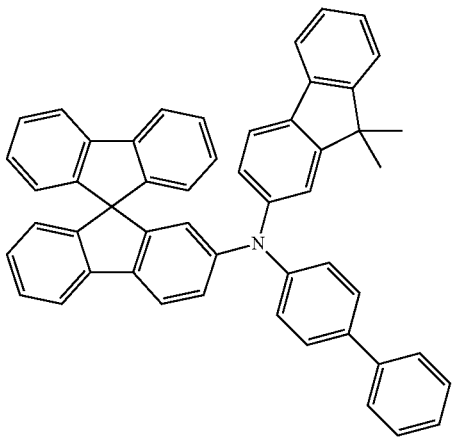
4-4
4-5
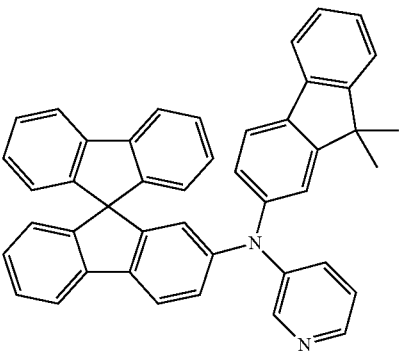
4-6
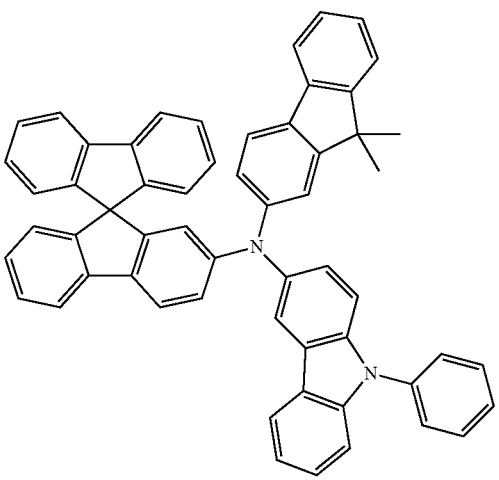

-continued
4-7
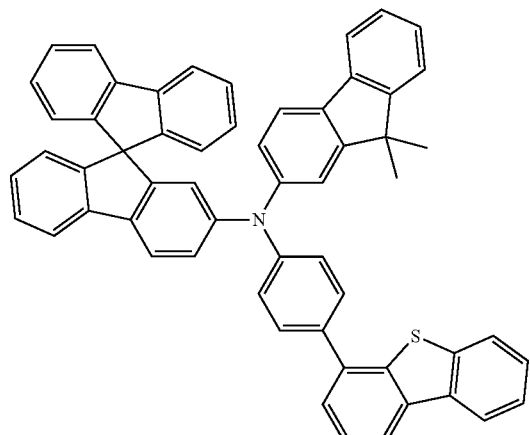
4-8
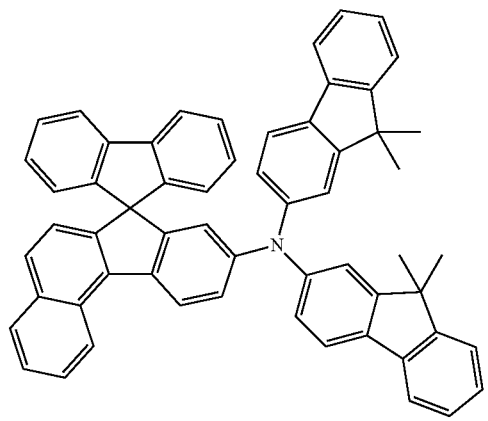
4-9
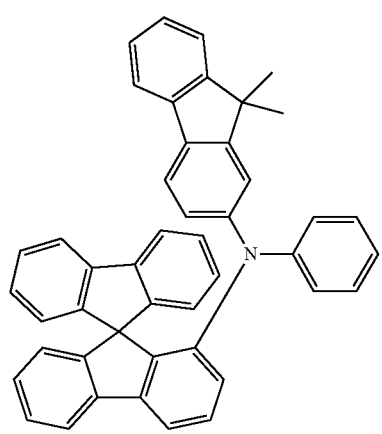
-continued
4-10
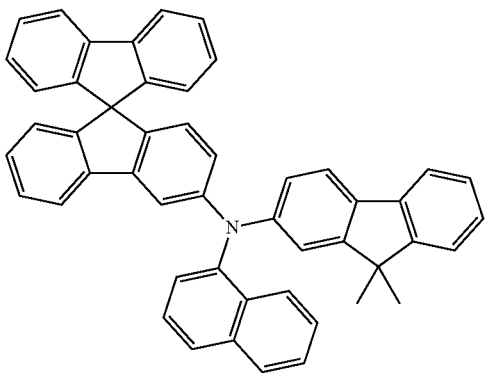
4-11
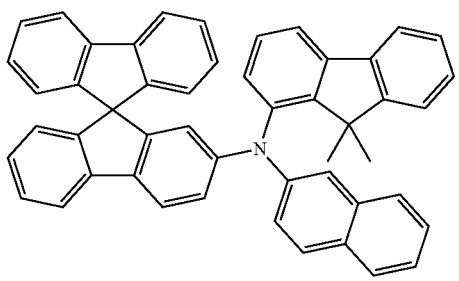
4-12
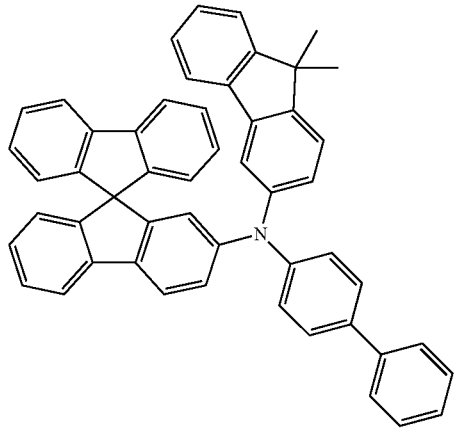
4-13
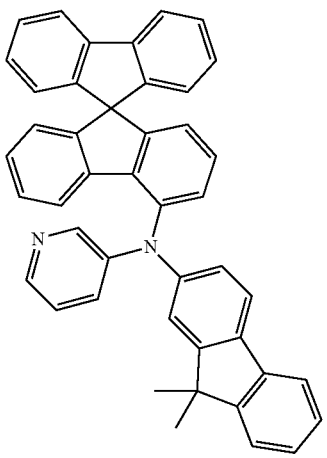

-continued
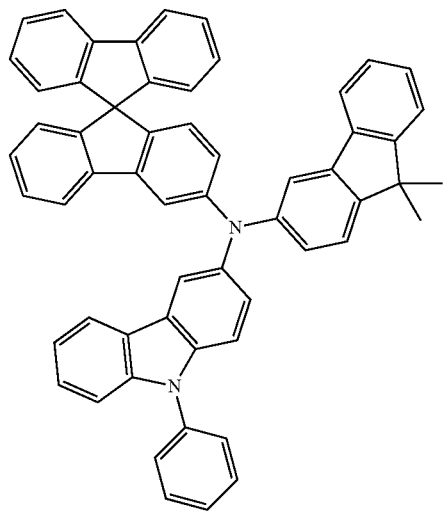
4-14
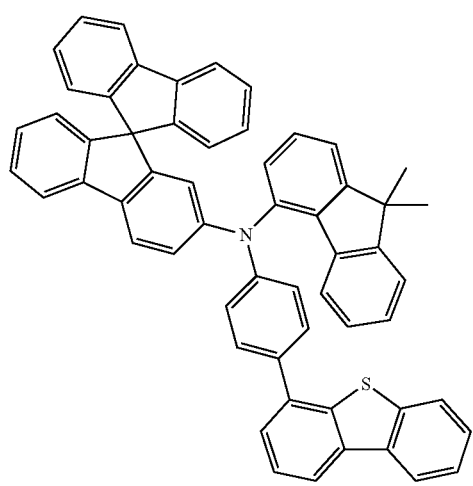
4-15
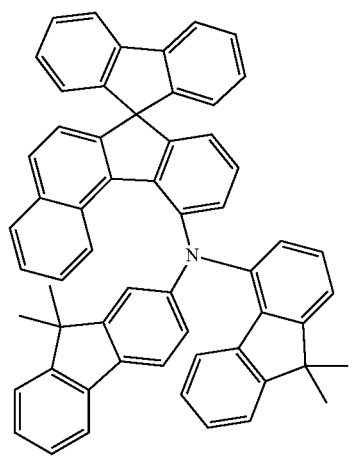
4-16
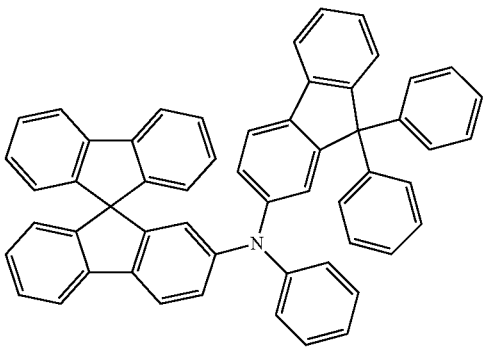
4-17
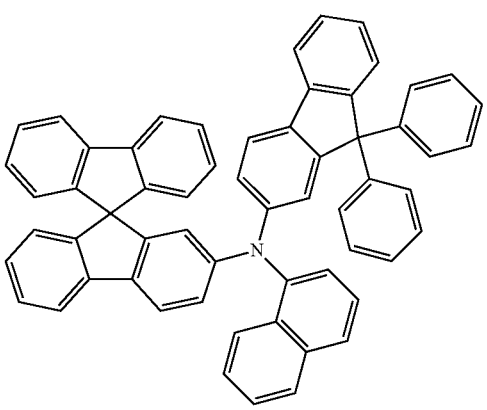
4-18
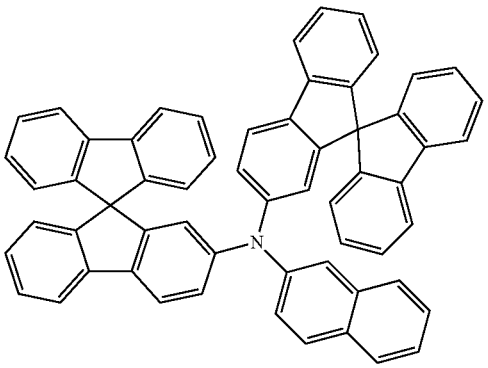
4-19
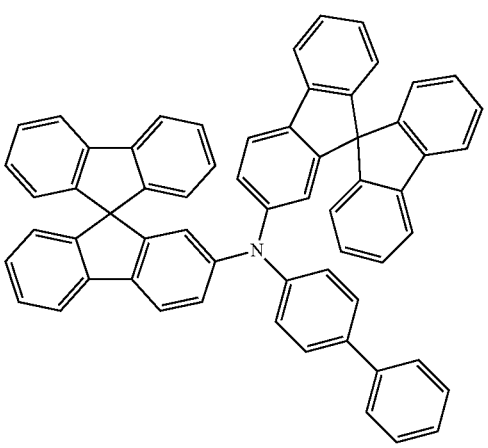
4-20

4-21
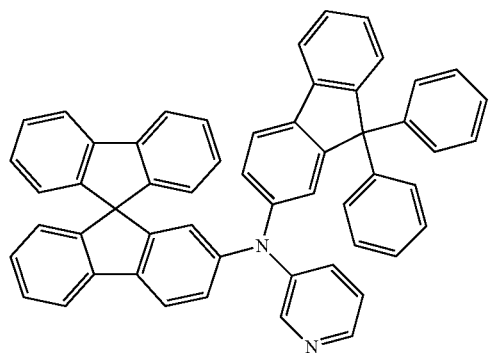
4-22
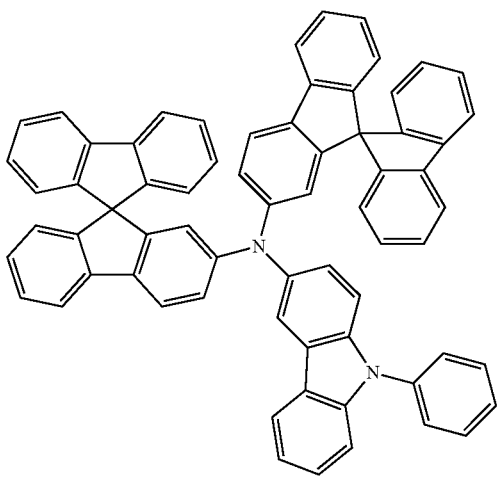
4-23
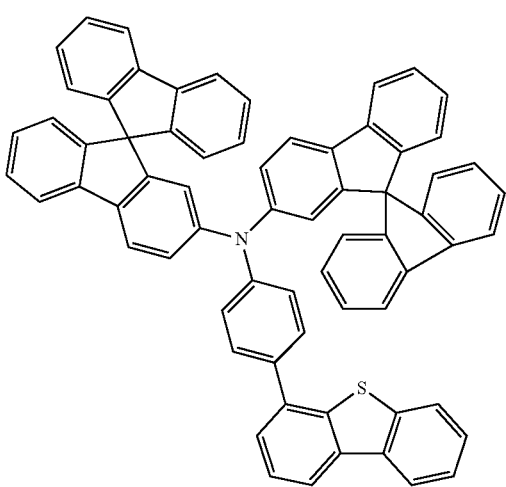
4-24
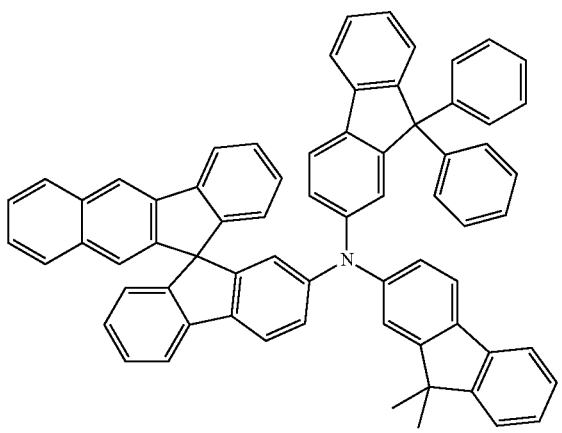
4-25
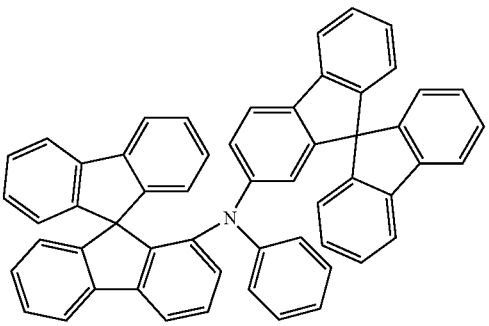
4-26
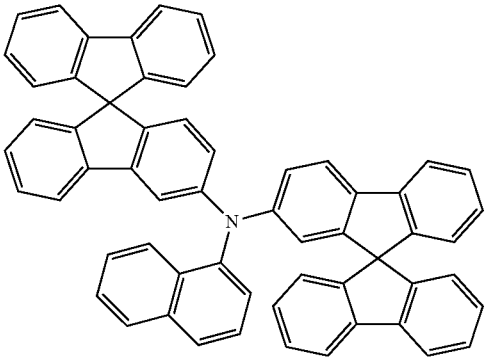
4-27
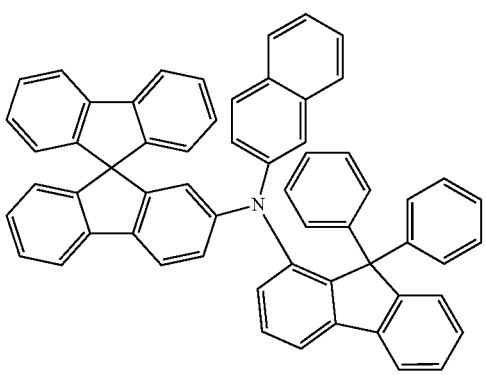

4-28
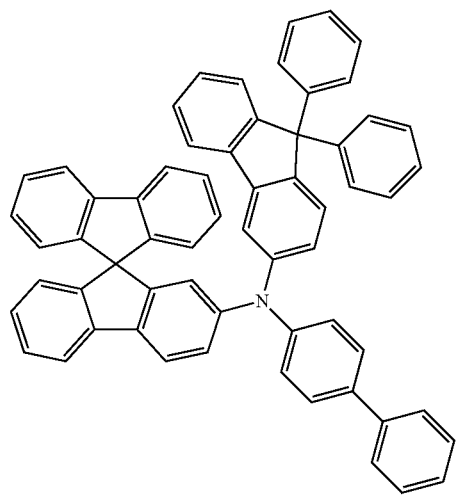
4-29
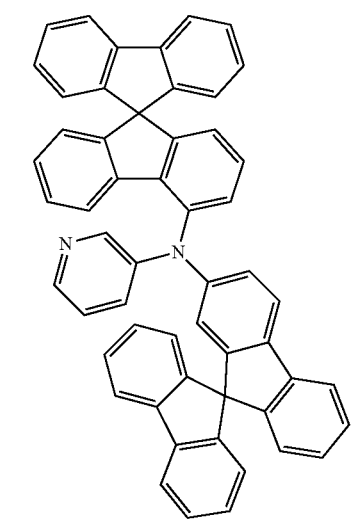
4-30
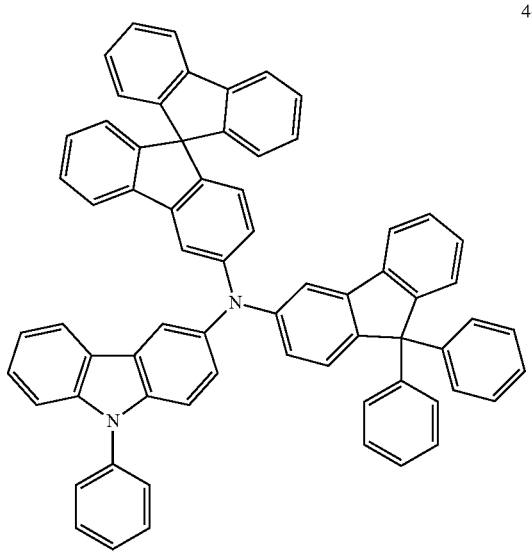
4-31
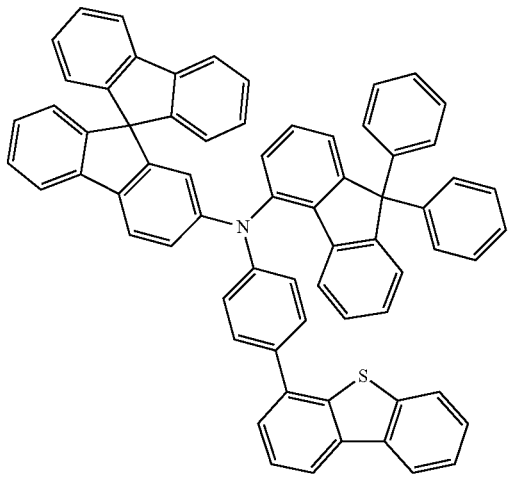
4-32
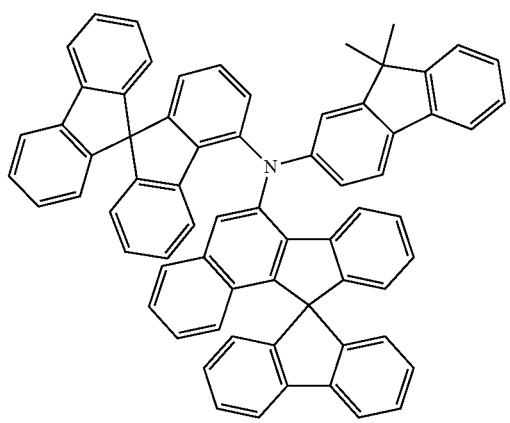
4-33
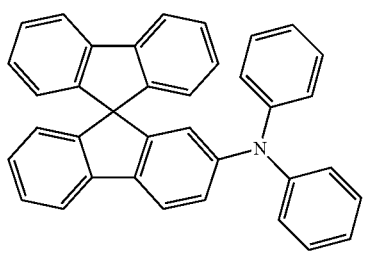
4-34
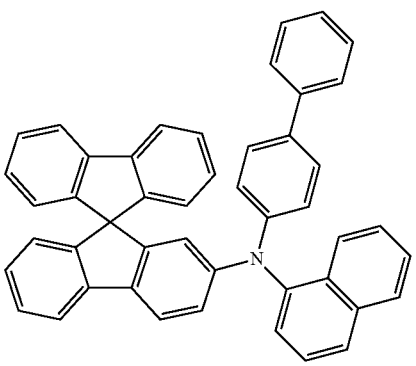

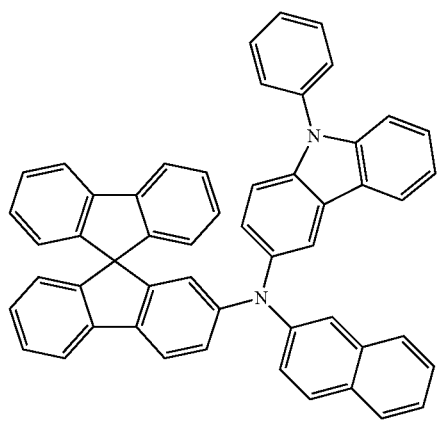

4-35

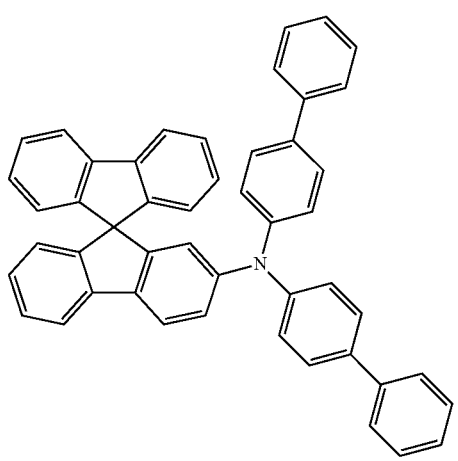

4-36

As another example, the present invention provides an organic electric element wherein the electron blocking layer comprises a compound represented by any one of Formulas (3) to (5), and the hole transport layer comprises a compound represented by any one of Formulas (6) to (8).

As another example, the present invention provides an organic electric element wherein the hole transport layer comprises any one of the compounds represented by Formulas 4-1 to 4-36, and the electron blocking layer comprises any one of the compounds represented by Formulas 1-1 to 3-12.

The present invention provides an organic electric element wherein the electron blocking layer comprises a composition in which two or more compounds having different structures among the compounds represented by Formula (1) are mixed.

Also, the present invention may comprise a composition wherein two or more compounds having different structures among the compounds represented by Formula (2) are mixed in the hole transport layer.

The present invention may further include a light efficiency enhancing layer formed on at least one of the opposite side to the organic material layer among one side of the first electrode and the second electrode, and the organic material layer is formed by one of a spin coating process, a nozzle printing process, an inkjet printing process, a slot coating process, a dip coating process or a roll-to-roll process.

Also, the present invention also provides an electronic device comprising a display device including the organic electric element; and a control unit for driving the display device.

According to another aspect, the present invention provides an electronic device characterized in that the organic electric element is at least one of an OLED, an organic solar cell, an organic photo conductor, an organic transistor and an element for monochromic or white illumination. Here, the electronic device may be a wired/wireless communication terminal which is currently used or will be used in the future, and covers all kinds of electronic devices including a mobile communication terminal such as a cellular phone, a personal digital assistant(PDA), an electronic dictionary, a point-to-multipoint(PMP), a remote controller, a navigation unit, a game player, various kinds of TVs, and various kinds of computers.

Hereinafter, synthesis examples of the compound represented by Formula according to the present invention and preparation examples of the organic electric element will be described in detail by way of example, but are not limited to the following examples of the invention.

Synthesis Example 1

The final products represented by Formula 1 according to the present invention can be synthesized by reaction between Sub 1 and Sub 2 as illustrated in the following Reaction Scheme 1.

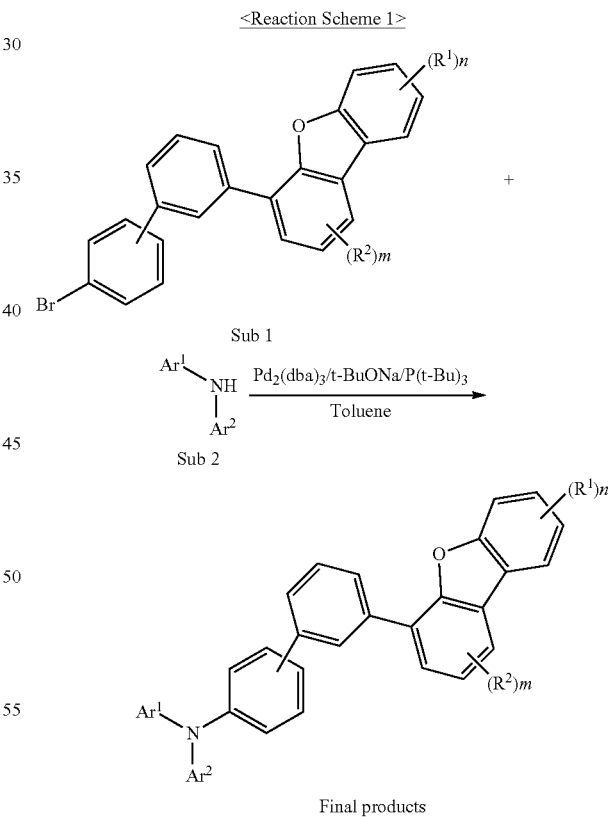

<Reaction Scheme 1>

Synthesis Examples of Sub 1

Sub 1 of Reaction Scheme 1 can be synthesized by the reaction path of the following Reaction Scheme 2, but is not limited thereto.

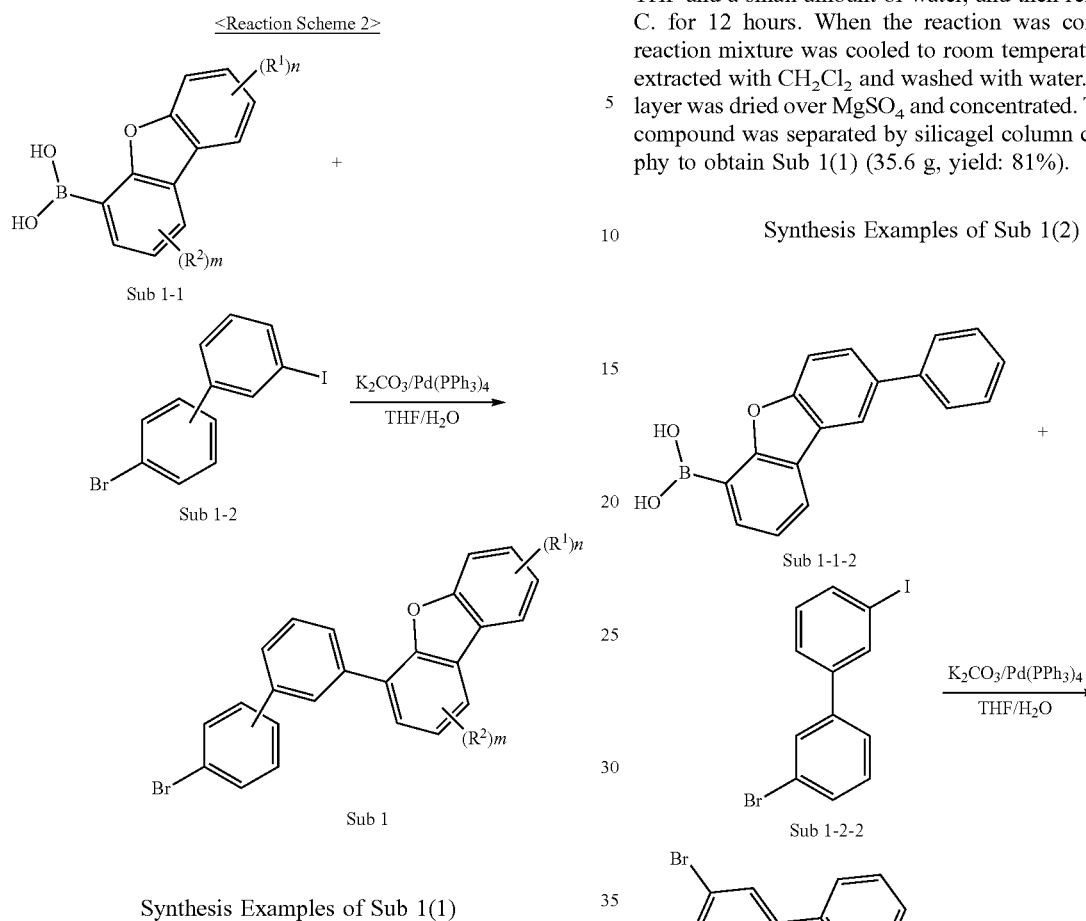

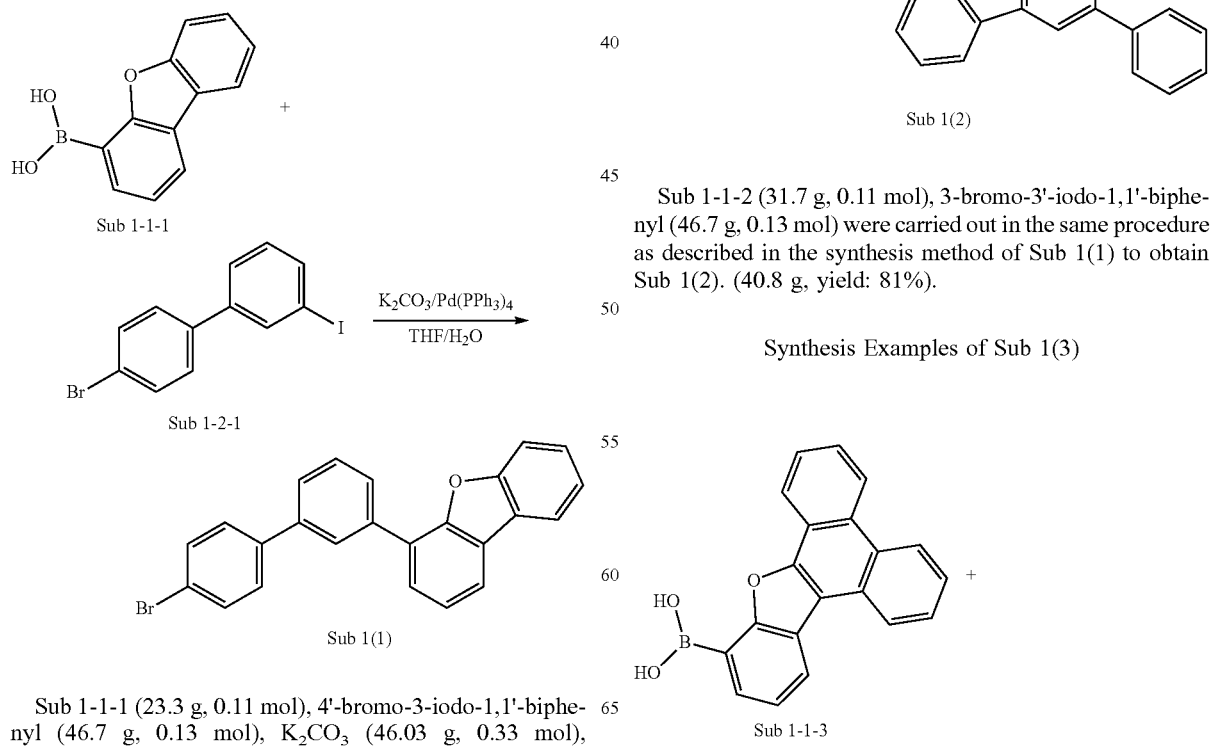

Synthesis Examples of Sub 1(1)

Sub 1-1-1 (23.3 g, 0.11 mol), 4'-bromo-3-iodo-1,1'-biphenyl (46.7 g, 0.13 mol), $K_2CO_3$ (46.03 g, 0.33 mol), $Pd(PPh_3)_4$ (5.13 g, 4 mol %) were dissolved in anhydrous THF and a small amount of water, and then refluxed at 80° C. for 12 hours. When the reaction was completed, the reaction mixture was cooled to room temperature, and was extracted with $CH_2Cl_2$ and washed with water. The organic layer was dried over $MgSO_4$ and concentrated. The resulting compound was separated by silicagel column chromatography to obtain Sub 1(1) (35.6 g, yield: 81%).

Synthesis Examples of Sub 1(2)

Sub 1-1-2 (31.7 g, 0.11 mol), 3-bromo-3'-iodo-1,1'-biphenyl (46.7 g, 0.13 mol) were carried out in the same procedure as described in the synthesis method of Sub 1(1) to obtain Sub 1(2). (40.8 g, yield: 81%).

Synthesis Examples of Sub 1(3)

-continued
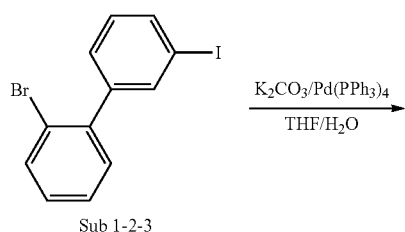
Sub 1-2-3
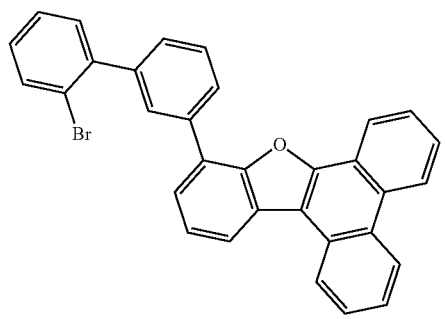
Sub 1(3)
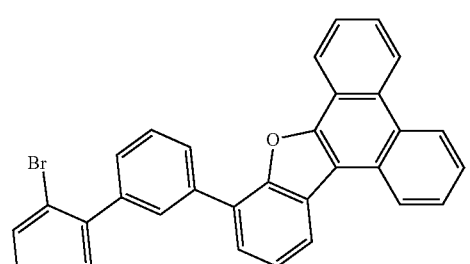
Sub 1(3)
Sub 1-1-3 (34.3 g, 0.11 mol), 2-bromo-3'-iodo-1,1'-biphenyl (46.7 g, 0.13 mol) were carried out in the same procedure as described in the synthesis method of Sub 1(1) to obtain Sub 1(3). (43.4 g, yield: 81%).
Examples of Sub 1 include, but are not limited to, the followings.
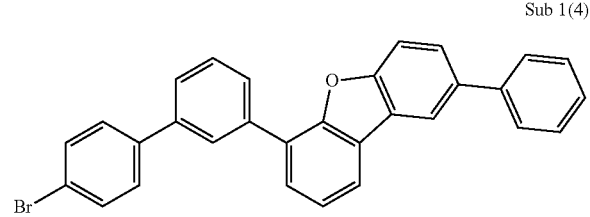
Sub 1(1)
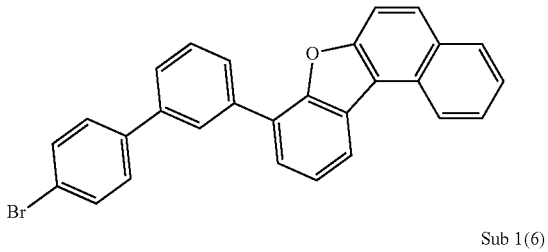
Sub 1(2)
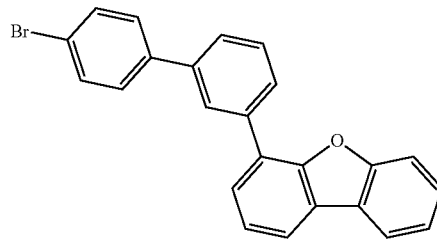
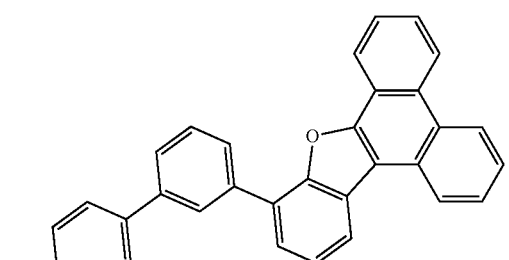
Sub 1(4)
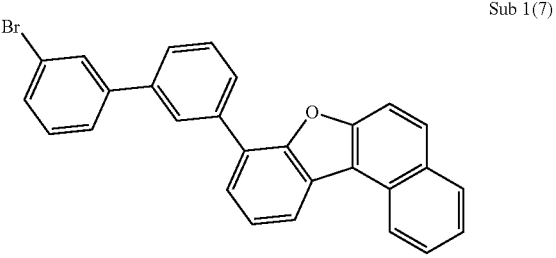
Sub 1(5)
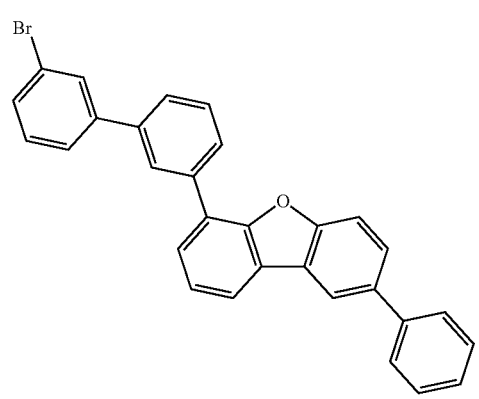
Sub 1(6)
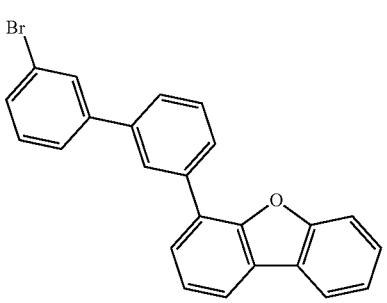
Sub 1(7)
Sub 1(8)

37
-continued

Sub 1(9)

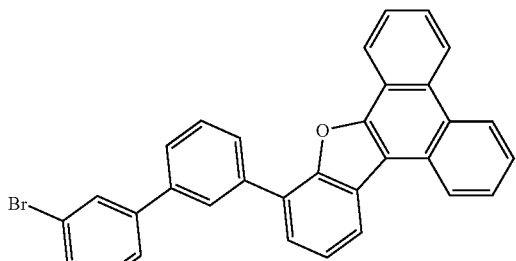

Sub 1(10)

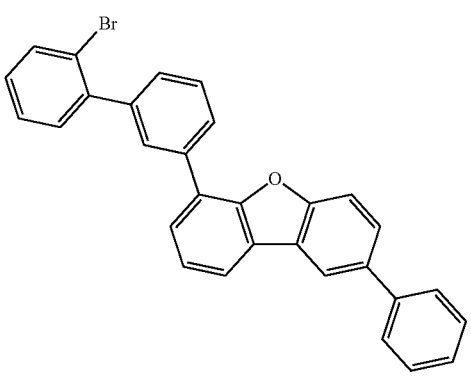

Sub 1(11)

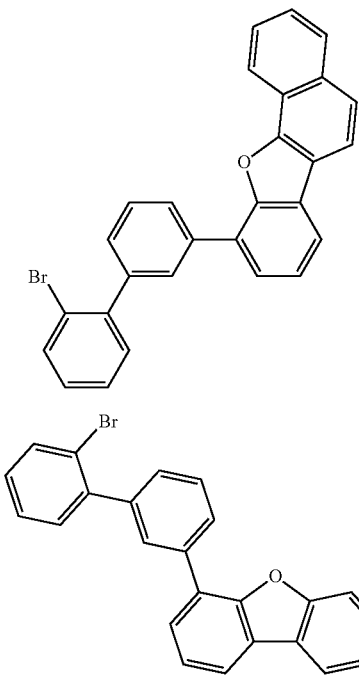

Sub 1(12)

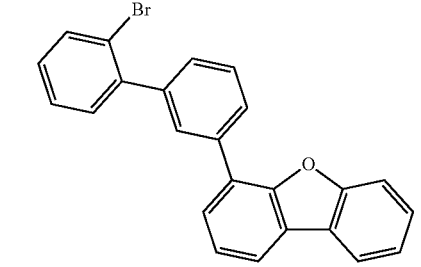

38
Synthesis Examples of Sub 2

Sub 2 of Reaction Scheme 1 can be synthesized by the reaction path of the following Reaction Scheme 3, but is not limited thereto.

<Reaction Scheme 3>

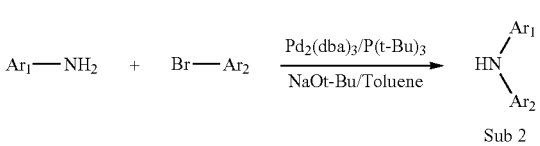

Synthesis Examples of Sub 2(1)

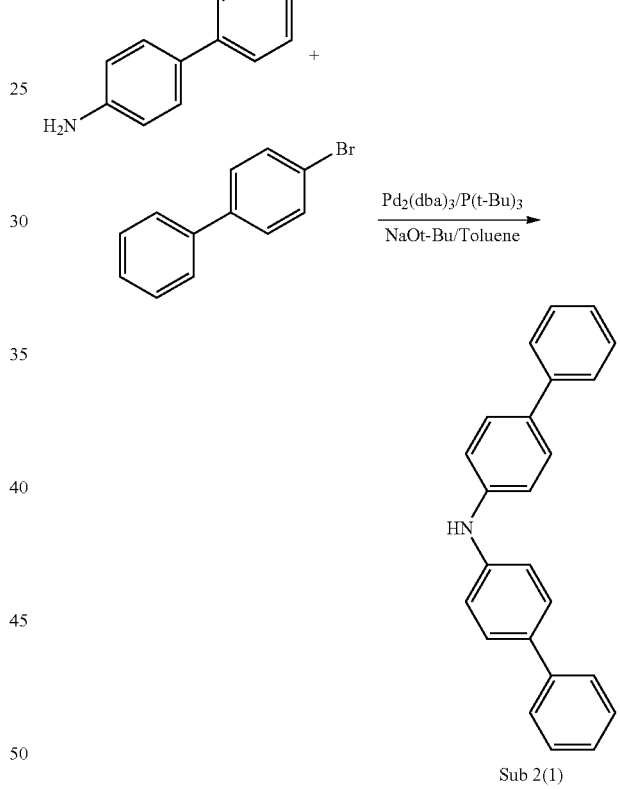

Sub 2(1)

After 4-bromo-1,1'-biphenyl (5.6 g, 24 mmol) was dissolved in toluene, [1,1'-biphenyl]-4-amine (3.4 g, 20 mmol), $Pd_2(dba)_3$ (0.5 g, 0.6 mmol), $P(t-Bu)_3$ (0.2 g, 2 mmol),

TABLE 1

| compound | FD-MS | compound | FD-MS |
|---|---|---|---|
| Sub 1(1) | m/z = 398.03($C_{24}H_{15}BrO$ = 399.28) | Sub 1(2) | m/z = 474.06($C_{30}H_{19}BrO$ = 475.38) |
| Sub 1(3) | m/z = 498.06($C_{32}H_{19}BrO$ = 499.40) | Sub 1(4) | m/z = 474.06($C_{30}H_{19}BrO$ = 475.38) |
| Sub 1(5) | m/z = 448.05($C_{28}H_{17}BrO$ = 449.34) | Sub 1(6) | m/z = 498.06($C_{32}H_{19}BrO$ = 499.40) |
| Sub 1(7) | m/z = 448.05($C_{28}H_{17}BrO$ = 449.34) | Sub 1(8) | m/z = 398.03($C_{24}H_{15}BrO$ = 399.28) |
| Sub 1(9) | m/z = 498.06($C_{32}H_{19}BrO$ = 499.40) | Sub 1(10) | m/z = 474.06($C_{30}H_{19}BrO$ = 475.38) |
| Sub 1(11) | m/z = 448.05($C_{28}H_{17}BrO$ = 449.34) | Sub 1(12) | m/z = 398.03($C_{24}H_{15}BrO$ = 399.28) |

NaOt-Bu (5.8 g, 60 mmol), toluene (300 mL) were added and refluxed with stirring at 100° C. for 24 hours. When the reaction was completed, the reaction mixture was extracted with ether and water. The organic layer was dried over MgSO$_4$ and concentrated. The resulting compound was separated by silicagel column chromatography and recrystallization to obtain 6.2 g of the product (yield: 80%).

Examples of Sub 2 include but are not limited to the followings

Sub 2(1)

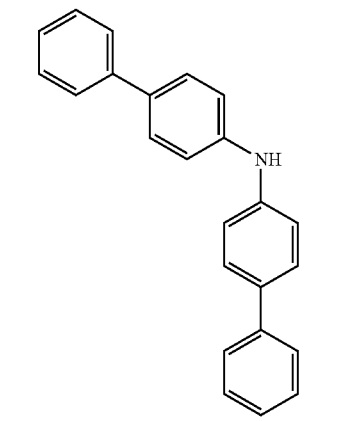

Sub 2(2)

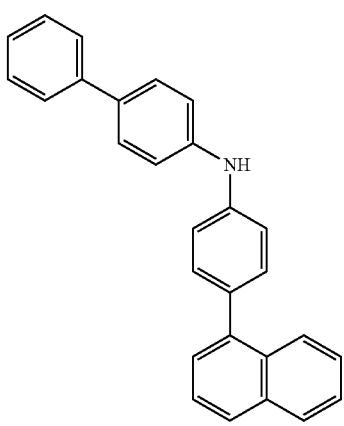

Sub 2(3)

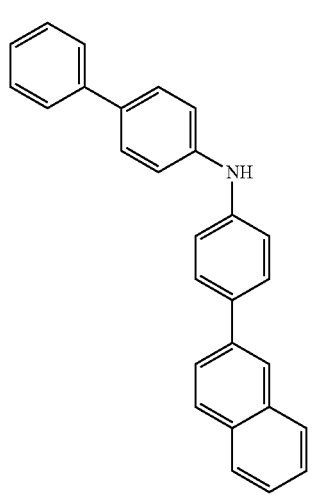

-continued

Sub 2(4)

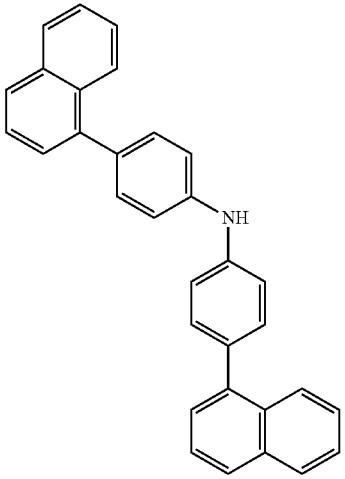

Sub 2(5)

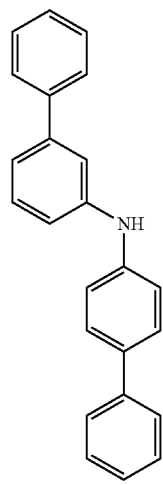

Sub 2(6)

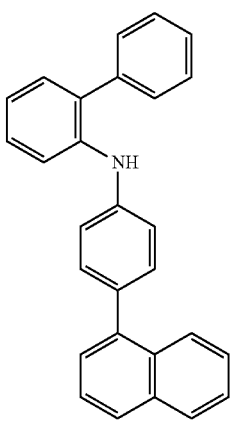

Sub 2(7)
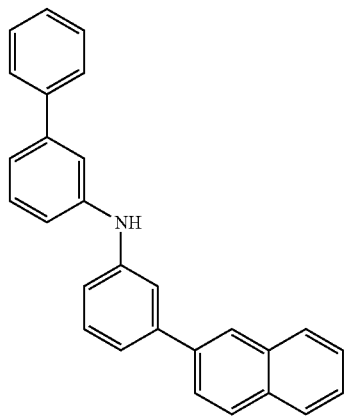
Sub 2(8)
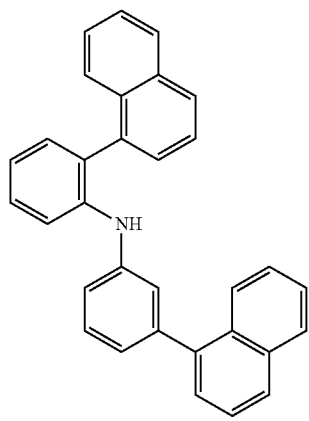
Sub 2(9)
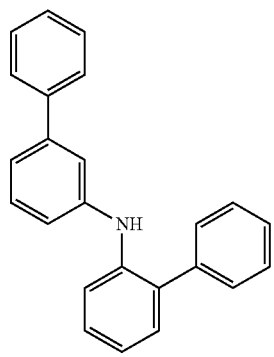
Sub 2(10)
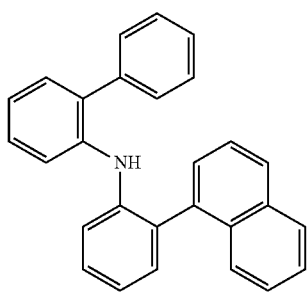
Sub 2(11)
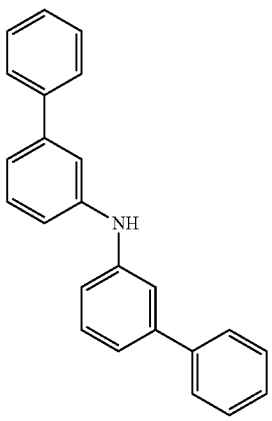
Sub 2(12)
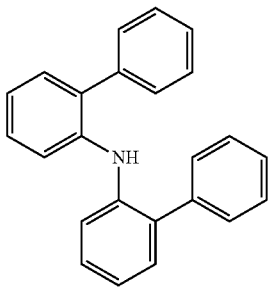
TABLE 2
| compound | FD-MS | compound | FD-MS |
| --- | --- | --- | --- |
| Sub 2(1) | m/z = 321.15($C_{24}H_{19}N$ = 321.41) | Sub 2(2) | m/z = 371.17($C_{28}H_{21}N$ = 371.47) |
| Sub 2(3) | m/z = 371.17($C_{28}H_{21}N$ = 371.47) | Sub 2(4) | m/z = 421.18($C_{32}H_{23}N$ = 421.53) |
| Sub 2(5) | m/z = 321.15($C_{24}H_{19}N$ = 321.41) | Sub 2(6) | m/z = 371.17($C_{28}H_{21}N$ = 371.47) |
| Sub 2(7) | m/z = 371.17($C_{28}H_{21}N$ = 371.47) | Sub 2(8) | m/z = 421.18($C_{32}H_{23}N$ = 421.53) |
| Sub 2(9) | m/z = 321.15($C_{24}H_{19}N$ = 321.41) | Sub 2(10) | m/z = 371.17($C_{28}H_{21}N$ = 371.47) |
| Sub 2(11) | m/z = 321.15($C_{24}H_{19}N$ = 321.41) | Sub 2(12) | m/z = 321.15($C_{24}H_{19}N$ = 321.41) |

Synthesis Example of Final Products

Synthesis Example of 1-1

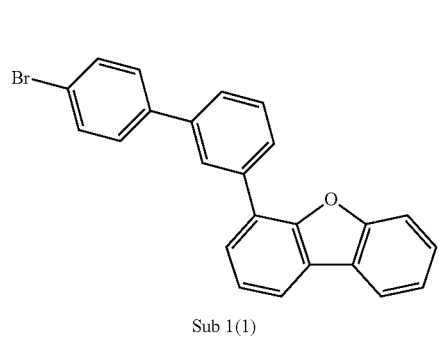

Sub 1(1)

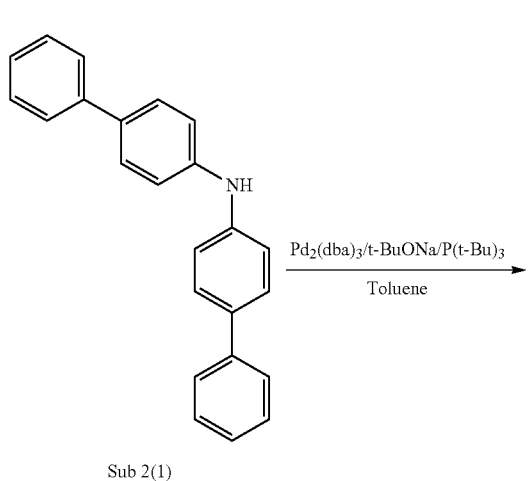

Sub 2(1)

1-1

Synthesis Example of 1-6

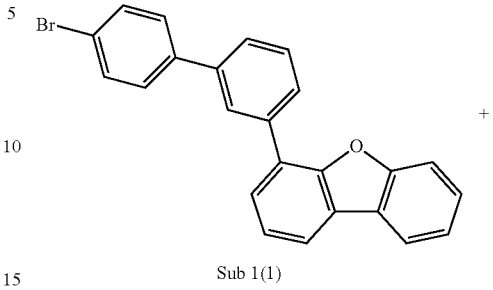

Sub 1(1)

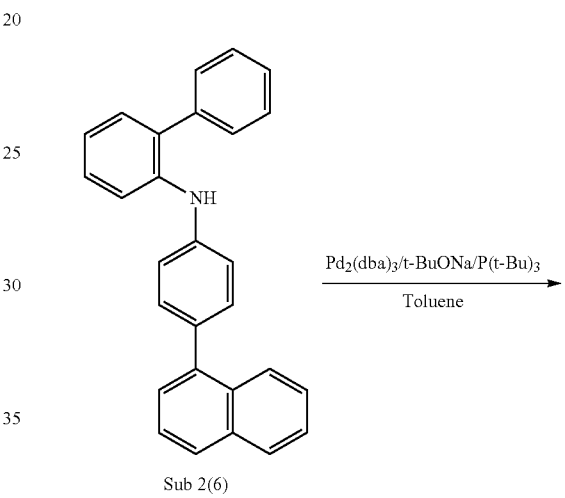

Sub 2(6)

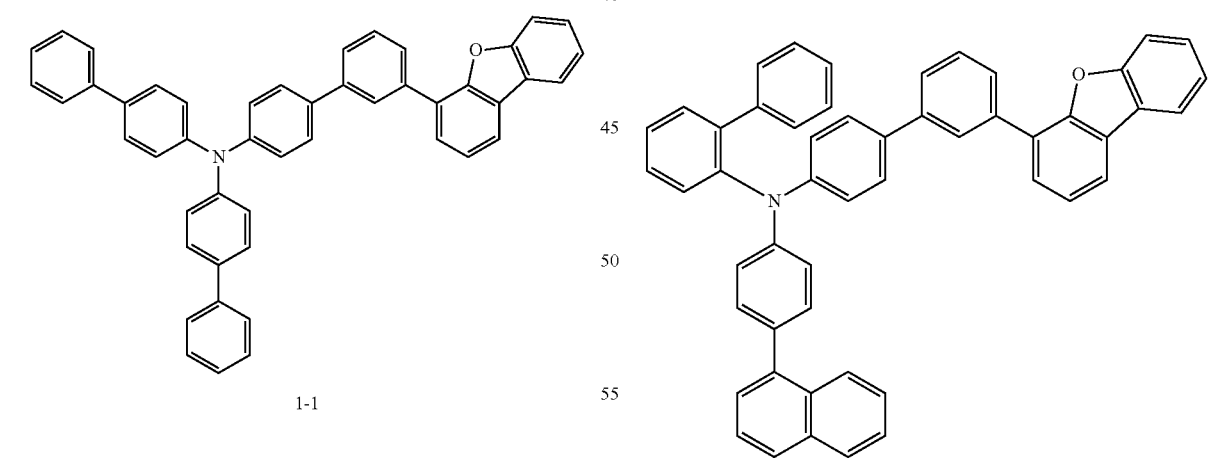

1-6

After Sub 1(1) (9.6 g, 24 mmol) was dissolved in toluene, Sub 2(1) (6.4 g, 20 mmol) was added and $Pd_2(dba)_3$ (0.5 g, 0.6 mmol), P(t-Bu)$_3$ (0.2 g, 2 mmol), NaOt-Bu (5.8 g, 60 mmol), toluene (300 mL) were added and refluxed with stirring at 100° C. for 24 hours. When the reaction was completed, the reaction mixture was extracted with ether and water. The organic layer was dried over $MgSO_4$ and concentrated. The resulting compound was separated by silica-gel column chromatography and recrystallization to obtain 13.1 g of the product (yield: 85%).

After Sub 1(1) (9.6 g, 24 mmol) was dissolved in toluene, Sub 2(6) (7.4 g, 20 mmol) was added, and carried out in the same procedure as described in the synthesis method of 1-1 to obtain 13.1 g of the final compound. (yield: 79%).

Synthesis Example of 1-11

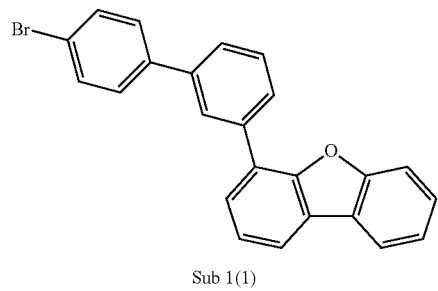

Synthesis Example of 2-4

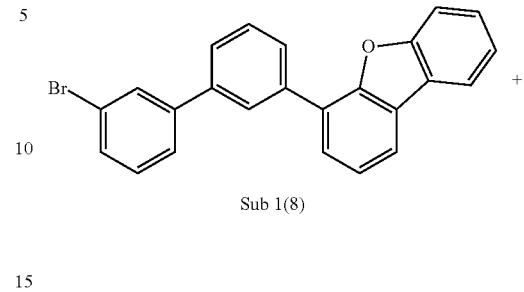

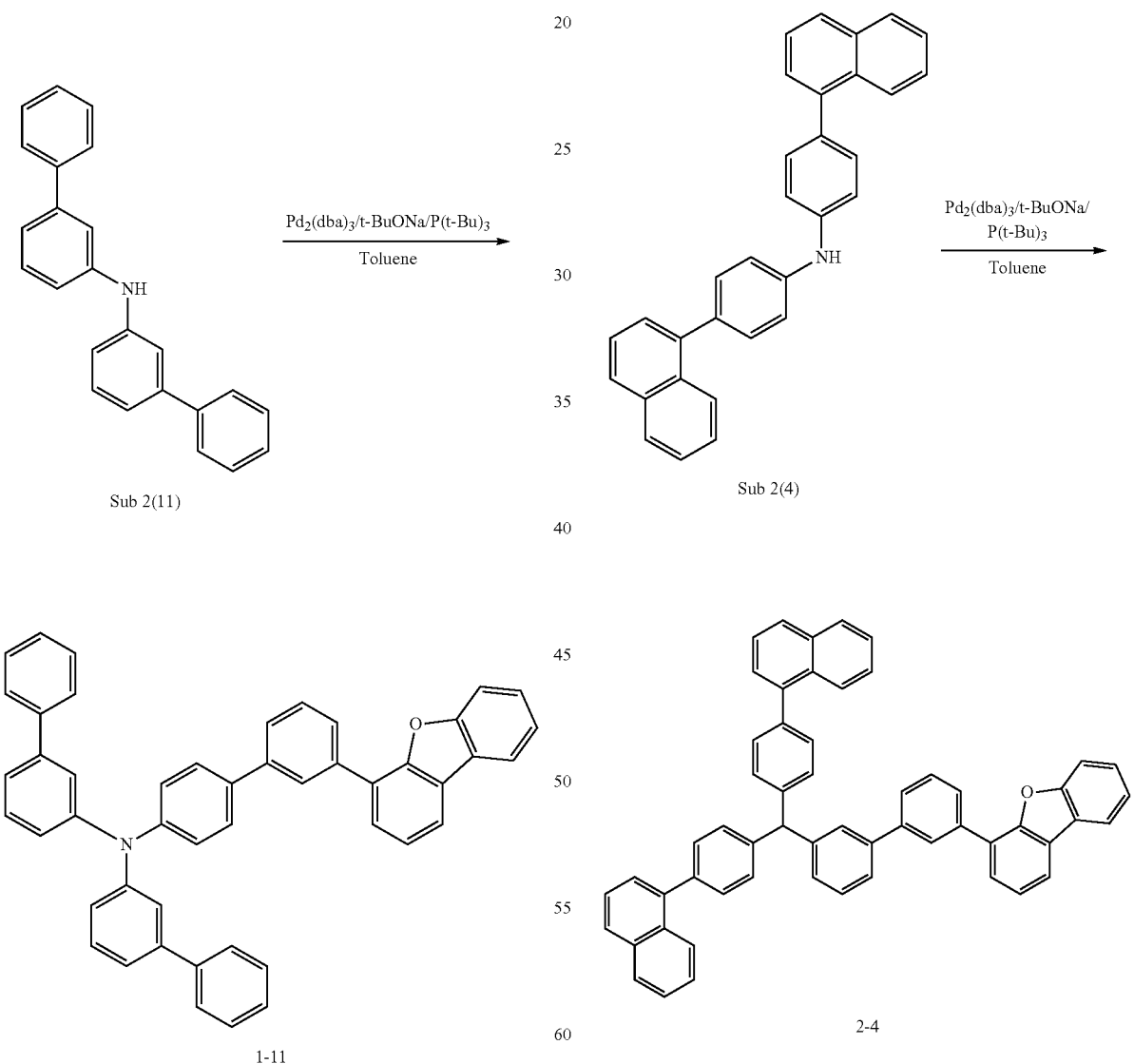

After Sub 1(1) (9.6 g, 24 mmol) was dissolved in toluene, Sub 2(11) (6.4 g, 20 mmol) was added, and carried out in the same procedure as described in the synthesis method of 1-1 to obtain 12.7 g of the final compound. (yield: 83%).

After Sub 1(8) (9.6 g, 24 mmol) was dissolved in toluene, Sub 2(4) (8.4 g, 20 mmol) was added, and carried out in the same procedure as described in the synthesis method of 1-1 to obtain 14.9 g of the final compound. (yield: 84%).

Synthesis Example of 2-5

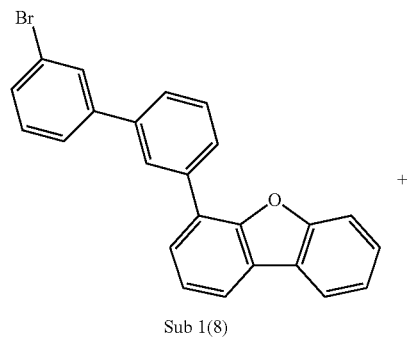

Sub 1(8)

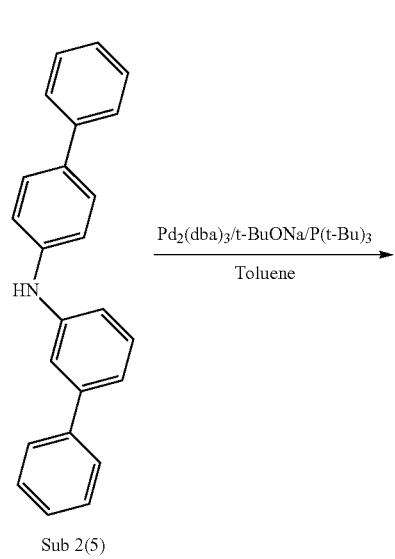

Sub 2(5)

2-5

Synthesis Example of 2-10

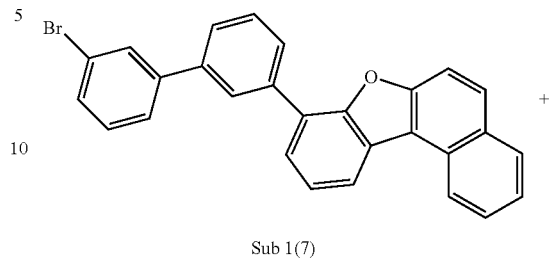

Sub 1(7)

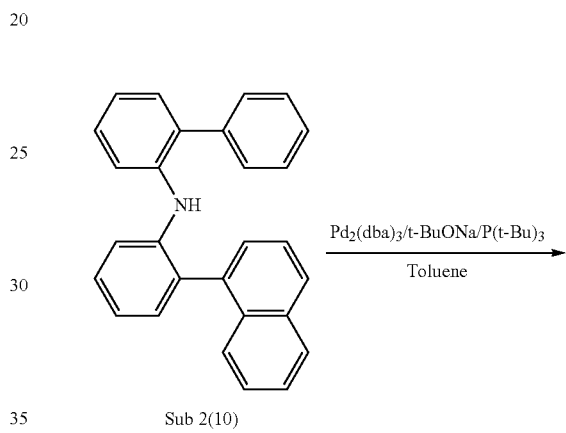

Sub 2(10)

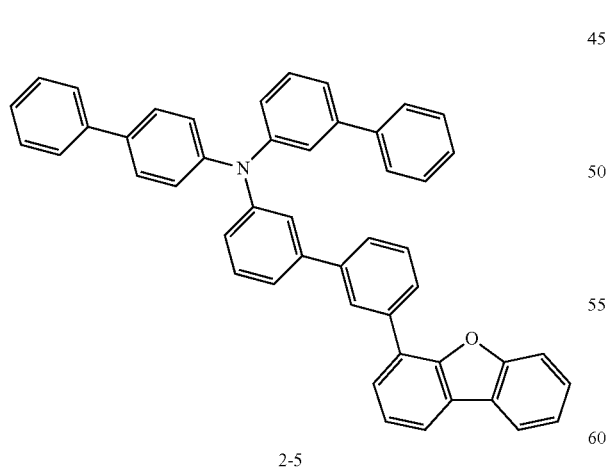

2-10

After Sub 1(8) (9.6 g, 24 mmol) was dissolved in toluene, Sub 2(5) (6.4 g, 20 mmol) was added, and carried out in the same procedure as described in the synthesis method of 1-1 to obtain 13.2 g of the final compound. (yield: 86%).

After Sub 1(7) (10.8 g, 24 mmol) was dissolved in toluene, Sub 2(10) (7.4 g, 20 mmol) was added, and carried out in the same procedure as described in the synthesis method of 1-1 to obtain 13.9 g of the final compound. (yield: 78%).

Synthesis Example of 3-3

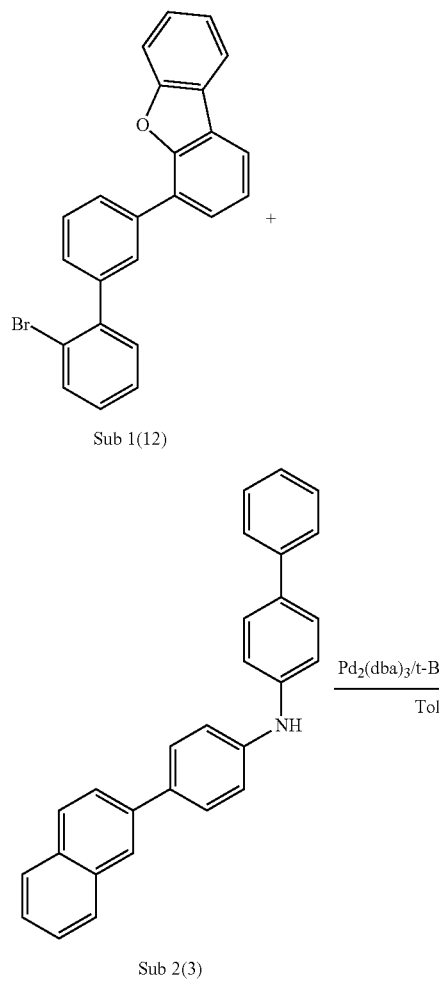

3-3

After Sub 1(12) (9.6 g, 24 mmol) was dissolved in toluene, Sub 2(3) (7.4 g, 20 mmol) was added, and carried out in the same procedure as described in the synthesis method of 1-1 to obtain 12.4 g of the final compound. (yield: 75%).

Synthesis Example of 3-8

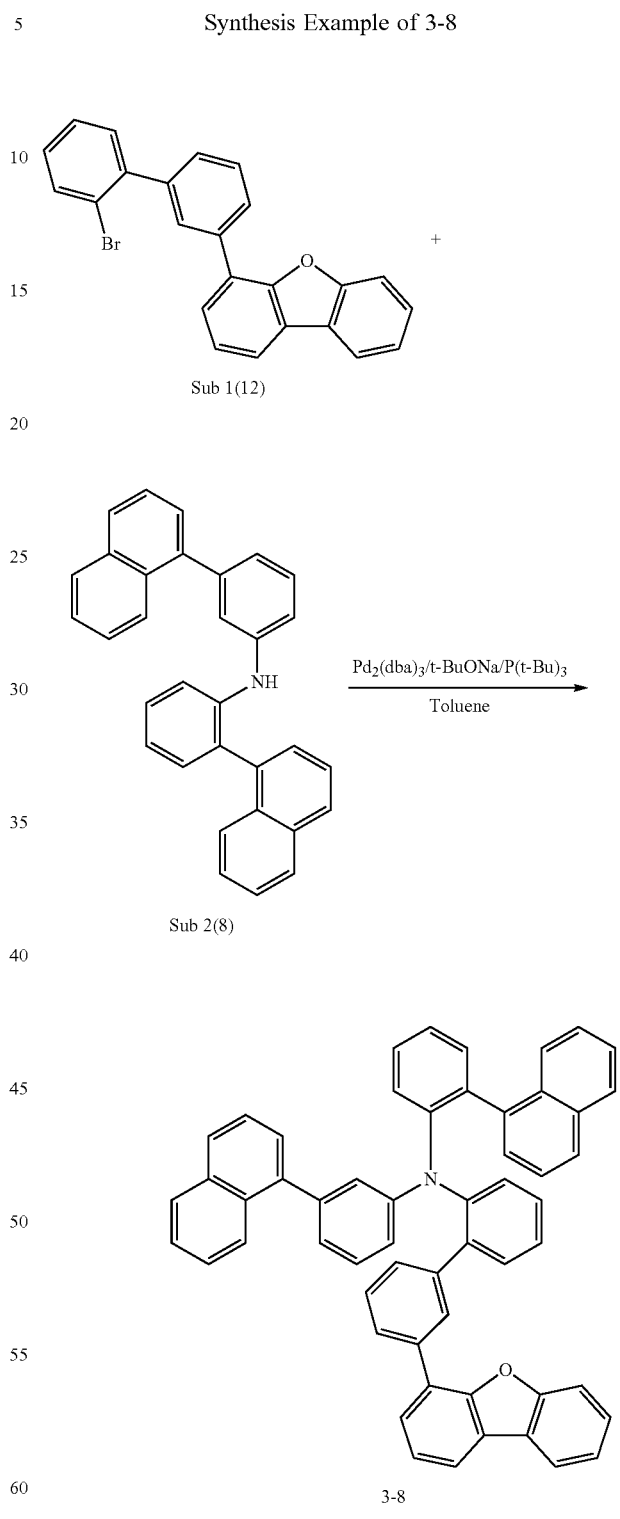

3-8

After Sub 1(12) (9.6 g, 24 mmol) was dissolved in toluene, Sub 2(8) (8.4 g, 20 mmol) was added, and carried out in the same procedure as described in the synthesis method of 1-1 to obtain 12.8 g of the final compound. (yield: 85%).

Synthesis Example of 3-9

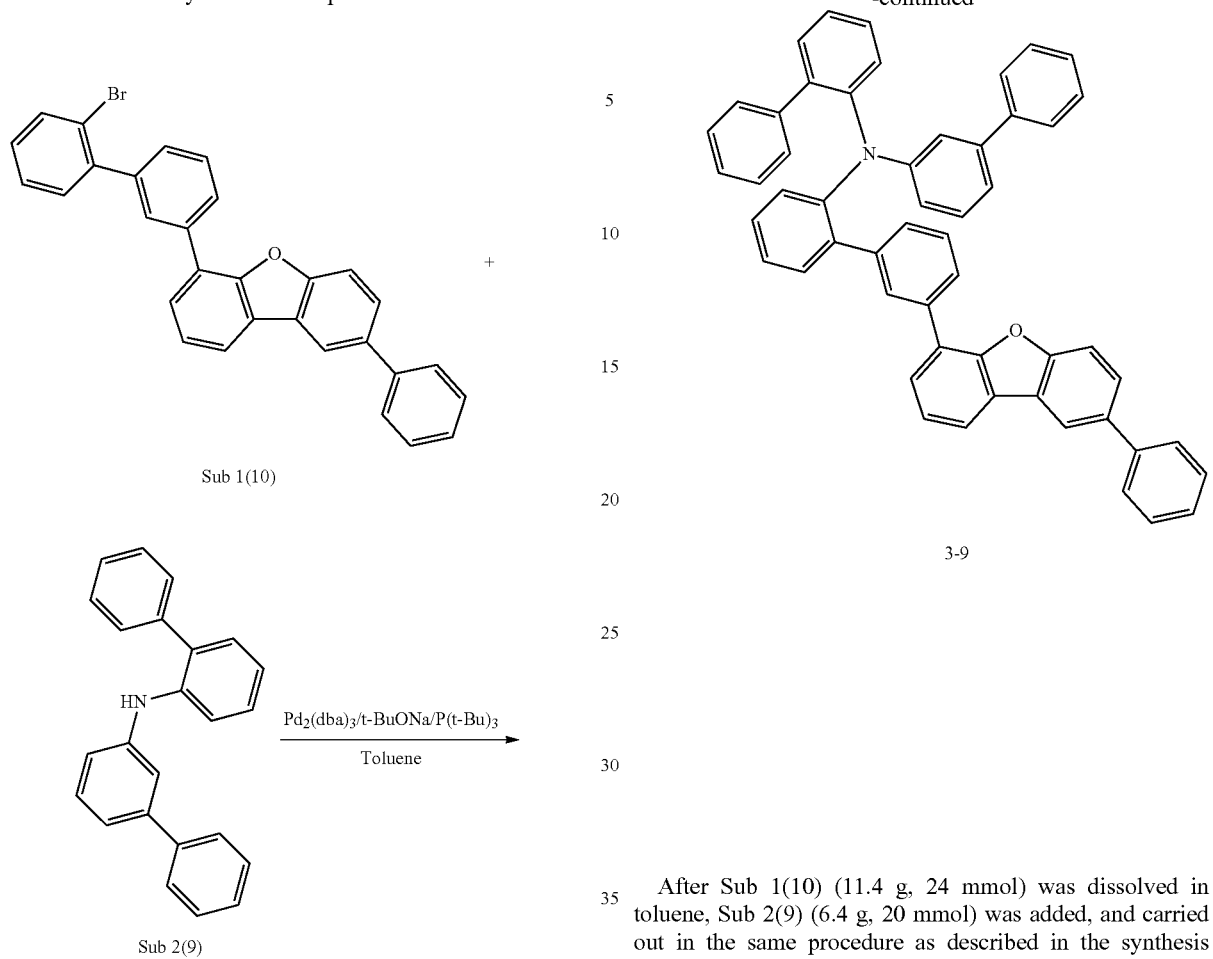

Sub 1(10)

Sub 2(9)

3-9

After Sub 1(10) (11.4 g, 24 mmol) was dissolved in toluene, Sub 2(9) (6.4 g, 20 mmol) was added, and carried out in the same procedure as described in the synthesis method of 1-1 to obtain 13.1 g of the final compound. (yield: 76%).

TABLE 3

| compound | FD-MS | compound | FD-MS |
|---|---|---|---|
| 1-1 | m/z = 639.26($C_{48}H_{33}NO$ = 639.78) | 1-2 | m/z = 689.27($C_{52}H_{35}NO$ = 689.84) |
| 1-3 | m/z = 689.27($C_{52}H_{35}NO$ = 689.84) | 1-4 | m/z = 739.29($C_{56}H_{37}NO$ = 739.90) |
| 1-5 | m/z = 639.26($C_{48}H_{33}NO$ = 639.78) | 1-6 | m/z = 689.27($C_{52}H_{35}NO$ = 689.84) |
| 1-7 | m/z = 689.27($C_{52}H_{35}NO$ = 689.84) | 1-8 | m/z = 739.29($C_{56}H_{37}NO$ = 739.90) |
| 1-9 | m/z = 715.29($C_{54}H_{37}NO$ = 715.88) | 1-10 | m/z = 739.29($C_{56}H_{37}NO$ = 739.90) |
| 1-11 | m/z = 639.26($C_{48}H_{33}NO$ = 639.78) | 1-12 | m/z = 739.29($C_{56}H_{37}NO$ = 739.90) |
| 2-1 | m/z = 639.26($C_{48}H_{33}NO$ = 639.78) | 2-2 | m/z = 689.27($C_{52}H_{35}NO$ = 689.84) |
| 2-3 | m/z = 689.27($C_{52}H_{35}NO$ = 689.84) | 2-4 | m/z = 739.29($C_{56}H_{37}NO$ = 739.90) |
| 2-5 | m/z = 639.26($C_{48}H_{33}NO$ = 639.78) | 2-6 | m/z = 689.27($C_{52}H_{35}NO$ = 689.84) |
| 2-7 | m/z = 689.27($C_{52}H_{35}NO$ = 689.84) | 2-8 | m/z = 739.29($C_{56}H_{37}NO$ = 739.90) |
| 2-9 | m/z = 715.29($C_{54}H_{37}NO$ = 715.88) | 2-10 | m/z = 739.29($C_{56}H_{37}NO$ = 739.90) |
| 2-11 | m/z = 639.26($C_{48}H_{33}NO$ = 639.78) | 2-12 | m/z = 739.29($C_{56}H_{37}NO$ = 739.90) |
| 3-1 | m/z = 639.26($C_{48}H_{33}NO$ = 639.78) | 3-2 | m/z = 689.27($C_{52}H_{35}NO$ = 689.84) |
| 3-3 | m/z = 689.27($C_{52}H_{35}NO$ = 689.84) | 3-4 | m/z = 739.29($C_{56}H_{37}NO$ = 739.90) |
| 3-5 | m/z = 639.26($C_{48}H_{33}NO$ = 639.78) | 3-6 | m/z = 689.27($C_{52}H_{35}NO$ = 689.84) |
| 3-7 | m/z = 689.27($C_{52}H_{35}NO$ = 689.84) | 3-8 | m/z = 739.29($C_{56}H_{37}NO$ = 739.90) |
| 3-9 | m/z = 715.29($C_{54}H_{37}NO$ = 715.88) | 3-10 | m/z = 739.29($C_{56}H_{37}NO$ = 739.90) |
| 3-11 | m/z = 639.26($C_{48}H_{33}NO$ = 639.78) | 3-12 | m/z = 739.29($C_{56}H_{37}NO$ = 739.90) |

Synthesis Example 2

The final products represented by Formula (2) of the present invention can be synthesized by reaction between Sub 3 and Sub 4 as illustrated in the following Reaction Scheme 4.

<Reaction Scheme 4>

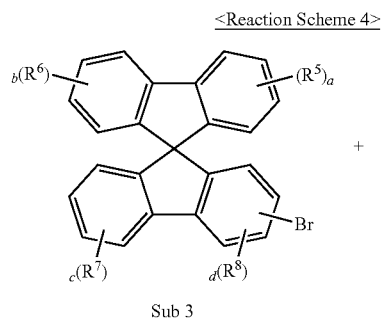

Sub 3

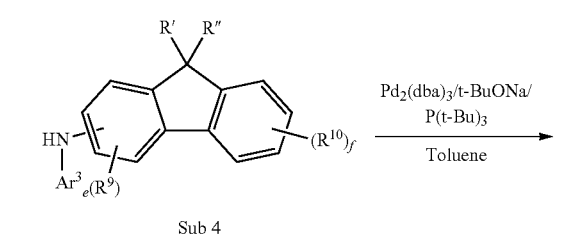

Sub 4

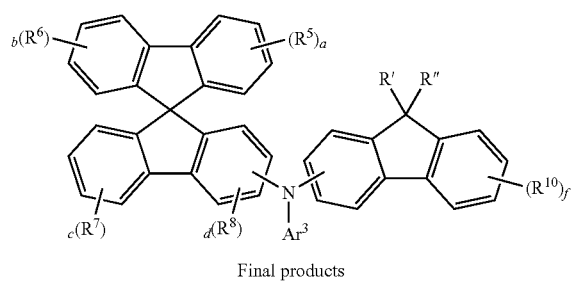

Final products

Synthesis Example 4-4

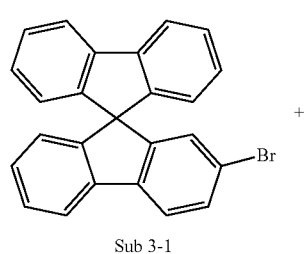

Sub 3-1

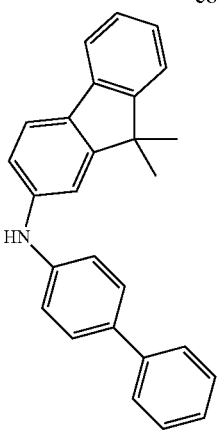

Sub 4-1

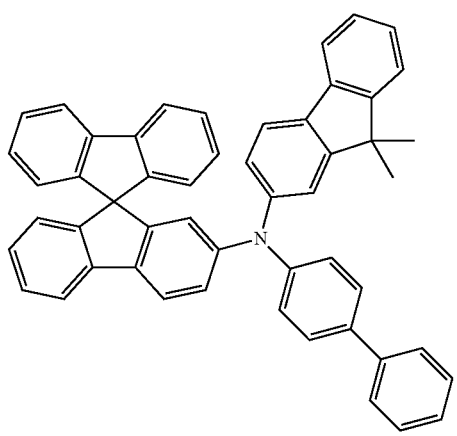

4-4

After Sub 3-1 (8.6 g, 24 mmol) was dissolved in toluene, Sub 4-1 (7.2 g, 20 mmol) was added, and Pd$_2$(dba)$_3$ (0.5 g, 0.6 mmol), P(t-Bu)$_3$ (0.2 g, 2 mmol), NaOt-Bu (5.8 g, 60 mmol), toluene (300 mL) were added and refluxed with stirring at 100° C. for 24 hours. When the reaction was completed, the reaction mixture was extracted with ether and water. The organic layer was dried over MgSO$_4$ and concentrated. The resulting compound was separated by silica-gel column chromatography and recrystallization to obtain 13.8 g of the product (yield: 85%).

Synthesis Example 4-9

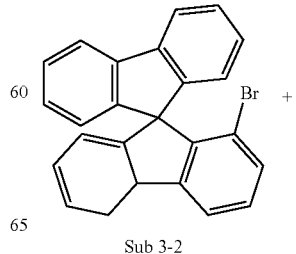

Sub 3-2

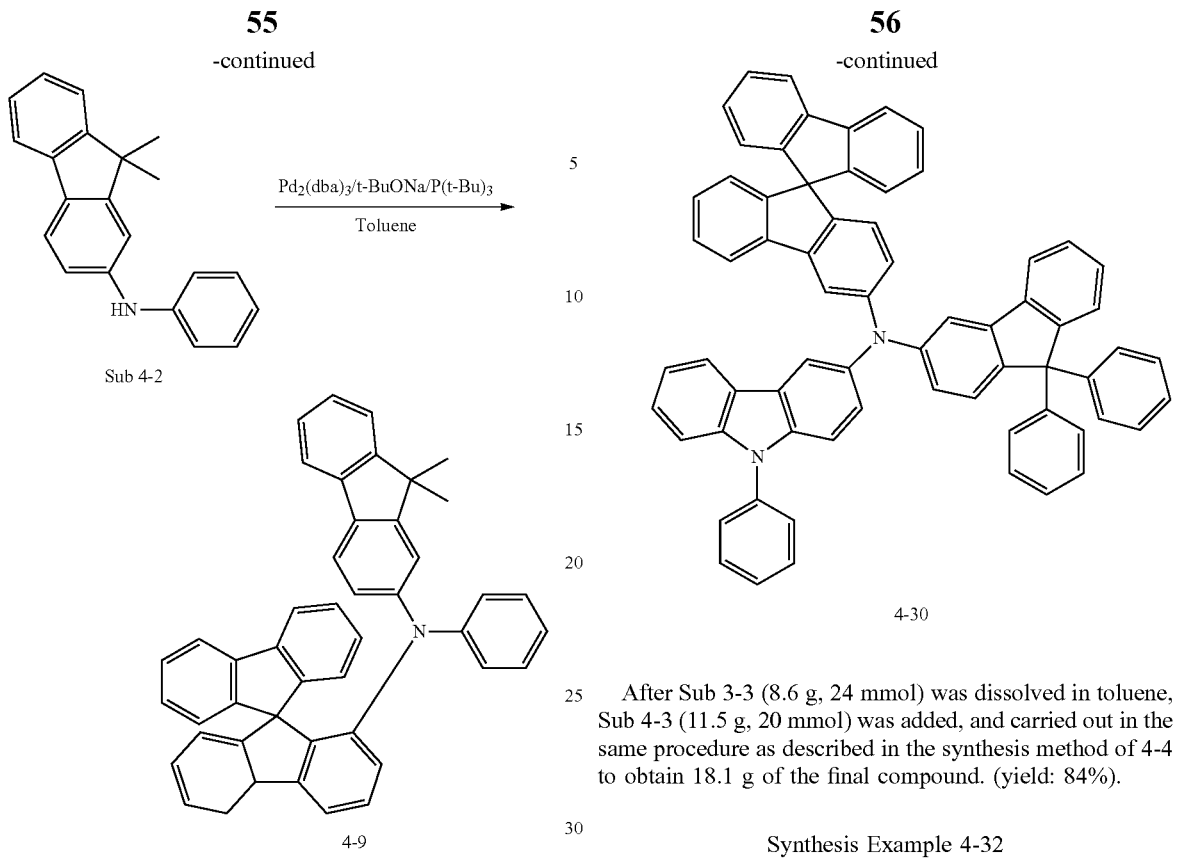

After Sub 3-2 (8.6 g, 24 mmol) was dissolved in toluene, Sub 4-2 (5.7 g, 20 mmol) was added, and carried out in the same procedure as described in the synthesis method of 4-4 to obtain 11.5 g of the final compound. (yield: 80%).

Synthesis Example 4-30

After Sub 3-3 (8.6 g, 24 mmol) was dissolved in toluene, Sub 4-3 (11.5 g, 20 mmol) was added, and carried out in the same procedure as described in the synthesis method of 4-4 to obtain 18.1 g of the final compound. (yield: 84%).

Synthesis Example 4-32

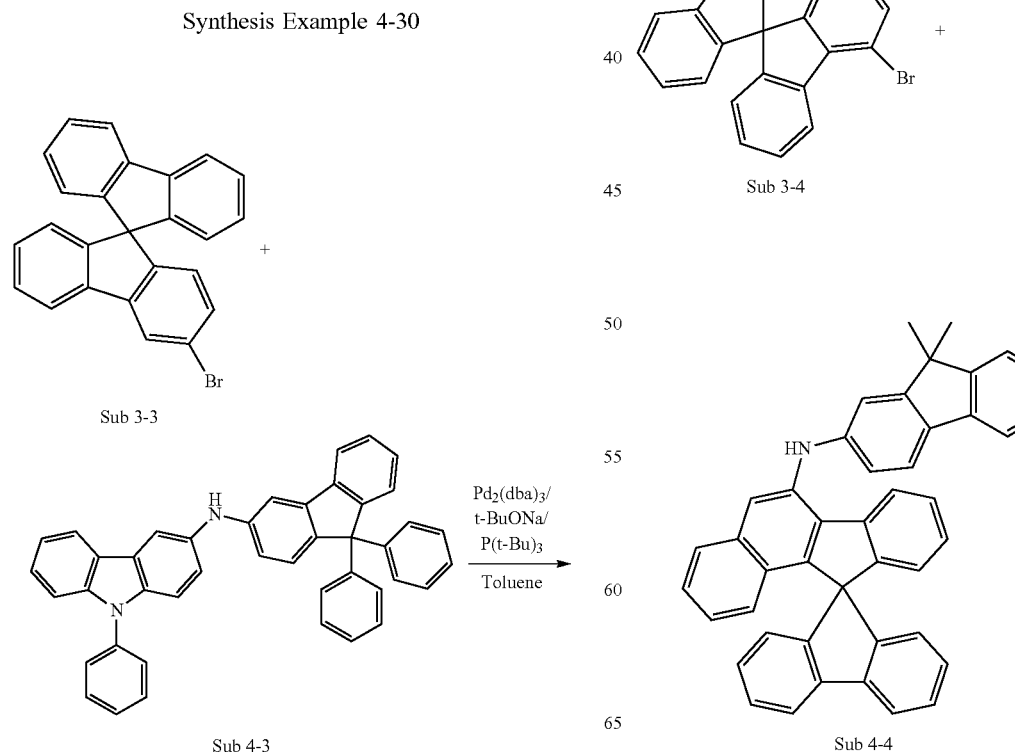

-continued

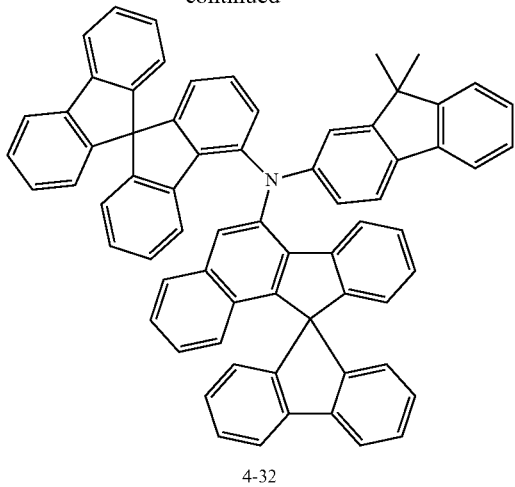

4-32

After Sub 3-4 (8.6 g, 24 mmol) was dissolved in toluene, Sub 4-4 (11.5 g, 20 mmol) was added, and carried out in the same procedure as described in the synthesis method of 4-4 to obtain 17.2 g of the final compound. (yield: 81%).

TABLE 4

| compound | FD-MS | compound | FD-MS |
|---|---|---|---|
| 4-1 | m/z = 599.26($C_{46}H_{33}N$ = 599.76) | 4-2 | m/z = 649.28($C_{50}H_{35}N$ = 649.82) |
| 4-3 | m/z = 649.28($C_{50}H_{35}N$ = 649.82) | 4-4 | m/z = 675.29($C_{52}H_{37}N$ = 675.86) |
| 4-5 | m/z = 600.26($C_{45}H_{32}N_2$ = 600.75) | 4-6 | m/z = 764.32($C_{58}H_{40}N_2$ = 764.95) |
| 4-7 | m/z = 781.28($C_{58}H_{39}NS$ = 782.00) | 4-8 | m/z = 765.34($C_{59}H_{43}N$ = 765.98) |
| 4-9 | m/z = 599.26($C_{46}H_{33}N$ = 599.76) | 4-10 | m/z = 649.28($C_{50}H_{35}N$ = 649.82) |
| 4-11 | m/z = 649.28($C_{50}H_{35}N$ = 649.82) | 4-12 | m/z = 675.29($C_{52}H_{37}N$ = 675.86) |
| 4-13 | m/z = 600.26($C_{45}H_{32}N_2$ = 600.75) | 4-14 | m/z = 764.32($C_{58}H_{40}N_2$ = 764.95) |
| 4-15 | m/z = 781.28($C_{58}H_{39}NS$ = 782.00) | 4-16 | m/z = 765.34($C_{59}H_{43}N$ = 765.98) |
| 4-17 | m/z = 723.29($C_{56}H_{37}N$ = 723.90) | 4-18 | m/z = 773.31($C_{60}H_{39}N$ = 773.96) |
| 4-19 | m/z = 773.31($C_{60}H_{39}N$ = 773.96) | 4-20 | m/z = 797.31($C_{62}H_{39}N$ = 797.98) |
| 4-21 | m/z = 724.29($C_{55}H_{36}N_2$ = 724.89) | 4-22 | m/z = 886.33($C_{68}H_{42}N_2$ = 887.07) |
| 4-23 | m/z = 903.30($C_{68}H_{41}NS$ = 904.12) | 4-24 | m/z = 889.37($C_{69}H_{47}N$ = 890.12) |
| 4-25 | m/z = 721.28($C_{56}H_{35}N$ = 721.88) | 4-26 | m/z = 771.29($C_{60}H_{37}N$ = 771.94) |
| 4-27 | m/z = 773.31($C_{60}H_{39}N$ = 773.96) | 4-28 | m/z = 799.32($C_{62}H_{41}N$ = 800.00) |
| 4-29 | m/z = 722.27($C_{55}H_{34}N_2$ = 722.87) | 4-30 | m/z = 888.35($C_{68}H_{44}N_2$ = 889.09) |
| 4-31 | m/z = 905.31($C_{68}H_{43}NS$ = 906.14) | 4-32 | m/z = 887.36($C_{69}H_{45}N$ = 888.10) |
| 4-33 | m/z = 483.20($C_{37}H_{25}N$ = 483.60) | 4-34 | m/z = 609.25($C_{47}H_{31}N$ = 609.76) |
| 4-35 | m/z = 698.27($C_{53}H_{34}N_2$ = 698.85) | 4-36 | m/z = 635.26($C_{49}H_{33}N$ = 635.79) |

Manufacture and Evaluation of Organic Electric Element

[Example 1] Manufacture and Evaluation of Blue Organic Electroluminescent Device (EBL)

First, on an ITO layer(anode) formed on a glass substrate, 2-TNATA was vacuum-deposited to form a hole injection layer with a thickness of 60 nm, and on the hole injection layer, the compound of the present invention represented by Formula (2) was vacuum deposited to a thickness of 60 nm to form a hole transport layer. Subsequently, on the hole transport layer, the compound of the present invention represented by Formula (1) was vacuum deposited to a thickness of 20 nm to form an EBL. Next, an emitting layer with a thickness of 30 nm was deposited on the EBL by doping 9,10-di(naphthalen-2-yl)anthracene as a host and BD-052X(Idemitsu kosan) as a dopant in a ratio of 96:4. As a hole blocking layer, (1,1'-bisphenyl)-4-olato)bis(2-methyl-8-quinolinolato)aluminum (hereinafter abbreviated as BAlq) was vacuum deposited to a thickness of 10 nm, and as an electron transport layer, tris(8-quinolinol)aluminum (hereinafter abbreviated as Alq3) was deposited to a thickness of 40 nm. After that, as an electron injection layer, an alkali metal halide, LiF was vacuum deposited to a thickness of 0.2 nm, and subsequently, Al was deposited to a thickness of 150 nm and was used as a cathode to produce an organic electroluminescent device.

To the OLEDs which were manufactured by examples and comparative examples, a forward bias direct current voltage was applied, and electroluminescent(EL) properties were measured using PR-650 of Photoresearch Co., and T95 life was measured using a life measuring apparatus manufactured by McScience Inc. with a reference luminance of 500 cd/m². In the following table, the manufacture of a device and the results of evaluation are shown.

Comparative Example 1

An organic electroluminescent device was manufactured in the same manner as in Example 1, except that Comparative Compound 1 was used as the hole transport compound and EBL was not used.

Comparative Example 2

An organic electroluminescent device was manufactured in the same manner as in Example 1, except that Comparative Compound 1 was used as the hole transport compound and Comparative Compound 2 was used as an EBL.

Comparative Example 3

An organic electroluminescent device was manufactured in the same manner as in Example 1, except that Comparative Compound 2 was used as an EBL.

Comparative Example 4

An organic electroluminescent device was manufactured in the same manner as in Example 1, except that Comparative Compound 1 was used as the hole transport compound.

Comparative Compound 1

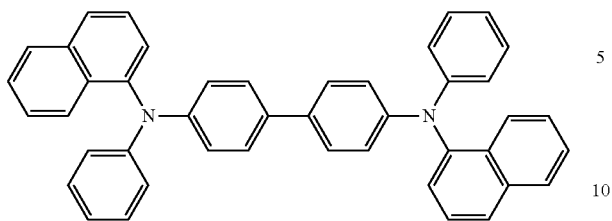

Comparative Compound 2

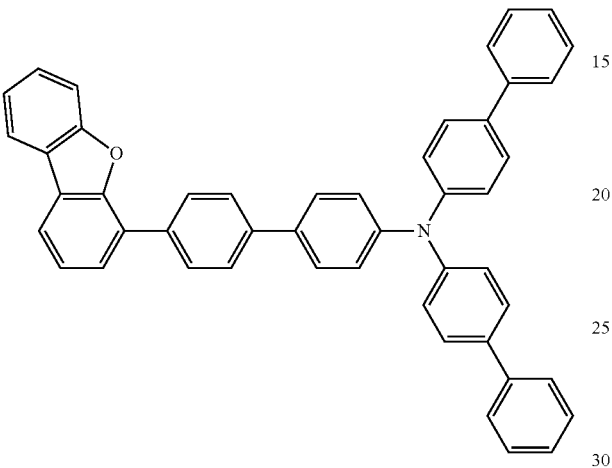

TABLE 5

| | Hole transport layer (HTL) | Electron blocking layer (EBL) | Voltage | Current Density | Brightness (cd/m$^2$) | Efficiency | Life time T(95) |
|---|---|---|---|---|---|---|---|
| comparative example(1) | Comparative compound 1 | — | 6.0 | 13.5 | 500.0 | 3.7 | 61.8 |
| comparative example(2) | Comparative compound 1 | Comparative compound 2 | 6.1 | 11.1 | 500.0 | 4.5 | 83.5 |
| comparative example(3) | compound 4-4 | Comparative compound 2 | 5.9 | 10.0 | 500.0 | 5.0 | 89.9 |
| comparative example (4) | Comparative compound 1 | compound 1-1 | 5.2 | 7.9 | 500.0 | 6.3 | 111.3 |
| example(1) | compound 4-4 | compound 1-1 | 4.3 | 5.6 | 500.0 | 9.0 | 120.9 |
| example(2) | compound 4-4 | compound 1-2 | 4.3 | 5.6 | 500.0 | 8.9 | 121.5 |
| example(3) | compound 4-4 | compound 1-3 | 4.2 | 5.6 | 500.0 | 9.0 | 127.2 |
| example(4) | compound 4-4 | compound 1-4 | 4.4 | 5.7 | 500.0 | 8.8 | 126.8 |
| example(5) | compound 4-4 | compound 2-5 | 4.3 | 5.8 | 500.0 | 8.6 | 126.4 |
| example(6) | compound 4-4 | compound 2-6 | 4.3 | 5.7 | 500.0 | 8.8 | 125.3 |
| example(7) | compound 4-4 | compound 2-7 | 4.3 | 5.8 | 500.0 | 8.6 | 122.1 |
| example(8) | compound 4-4 | compound 2-8 | 4.3 | 5.8 | 500.0 | 8.6 | 127.7 |
| example(9) | compound 4-4 | compound 3-1 | 4.2 | 5.9 | 500.0 | 8.4 | 124.1 |
| example(10) | compound 4-4 | compound 3-2 | 4.4 | 5.9 | 500.0 | 8.5 | 125.5 |
| example(11) | compound 4-4 | compound 3-6 | 4.3 | 5.9 | 500.0 | 8.5 | 129.8 |
| example(12) | compound 4-4 | compound 3-8 | 4.4 | 5.9 | 500.0 | 8.5 | 126.1 |
| example(13) | compound 4-17 | compound 1-1 | 4.6 | 6.1 | 500.0 | 8.2 | 129.8 |

TABLE 5-continued

| | Hole transport layer (HTL) | Electron blocking layer (EBL) | Voltage | Current Density | Brightness (cd/m$^2$) | Efficiency | Life time T(95) |
|---|---|---|---|---|---|---|---|
| example(14) | compound 4-17 | compound 1-2 | 4.5 | 6.1 | 500.0 | 8.2 | 125.4 |
| example(15) | compound 4-17 | compound 1-3 | 4.4 | 6.0 | 500.0 | 8.3 | 120.9 |
| example(16) | compound 4-17 | compound 1-4 | 4.5 | 6.1 | 500.0 | 8.2 | 127.9 |
| example(17) | compound 4-17 | compound 2-5 | 4.5 | 6.1 | 500.0 | 8.1 | 125.9 |
| example(18) | compound 4-17 | compound 2-6 | 4.5 | 6.1 | 500.0 | 8.2 | 120.6 |
| example(19) | compound 4-17 | compound 2-7 | 4.5 | 6.2 | 500.0 | 8.0 | 122.2 |
| example(20) | compound 4-17 | compound 2-8 | 4.5 | 6.2 | 500.0 | 8.1 | 127.2 |
| example(21) | compound 4-17 | compound 3-1 | 4.4 | 6.3 | 500.0 | 7.9 | 126.1 |
| example(22) | compound 4-17 | compound 3-2 | 4.5 | 6.3 | 500.0 | 8.0 | 121.5 |
| example(23) | compound 4-17 | compound 3-6 | 4.6 | 6.3 | 500.0 | 7.9 | 121.1 |
| example(24) | compound 4-17 | compound 3-8 | 4.5 | 6.3 | 500.0 | 7.9 | 126.5 |
| example(25) | compound 4-20 | compound 1-1 | 4.8 | 6.5 | 500.0 | 7.7 | 124.8 |
| example(26) | compound 4-20 | compound 1-2 | 4.7 | 6.4 | 500.0 | 7.8 | 121.8 |
| example(27) | compound 4-20 | compound 1-3 | 4.8 | 6.4 | 500.0 | 7.8 | 124.9 |
| example(28) | compound 4-20 | compound 1-4 | 4.7 | 6.6 | 500.0 | 7.6 | 123.2 |
| example(29) | compound 4-20 | compound 2-5 | 4.6 | 6.7 | 500.0 | 7.4 | 129.8 |
| example(30) | compound 4-20 | compound 2-6 | 4.6 | 6.7 | 500.0 | 7.5 | 126.3 |
| example(31) | compound 4-20 | compound 2-7 | 4.6 | 6.7 | 500.0 | 7.5 | 126.4 |
| example(32) | compound 4-20 | compound 2-8 | 4.7 | 6.6 | 500.0 | 7.6 | 126.4 |
| example(33) | compound 4-20 | compound 3-1 | 4.7 | 6.9 | 500.0 | 7.3 | 122.6 |
| example(34) | compound 4-20 | compound 3-2 | 4.6 | 6.9 | 500.0 | 7.2 | 127.7 |
| example(35) | compound 4-20 | compound 3-6 | 4.8 | 6.9 | 500.0 | 7.2 | 129.4 |
| example(36) | compound 4-20 | compound 3-8 | 4.7 | 6.9 | 500.0 | 7.3 | 128.3 |

As can be seen from the results of Table 5, when the organic electric element material of the present invention represented by the Formula (2) was used as a hole transport layer and the organic electric element material of the present invention represented by the Formula (1) was used as an electron blocking layer, it was confirmed that the driving voltage, efficiency, and life span were significantly improved as compared with the elements not using the same.

Examples of devices using a hole blocking layer were superior to those of Comparative Example 1 not using a hole blocking layer, and Inventive Examples 1 to 36 using Formula (2) as the hole transport layer and Formula (1) as the electron blocking layer were significantly better than Examples using at least one of Comparative Compound 1 or Comparative Compound 2 as a hole transporting layer or an electron blocking layer(Comparative Examples 2 and 4 using Comparative Compound 1 as a hole transport layer, Comparative Examples 2 and 3 using Comparative Compound 2 as an electron blocking layer) in driving voltage, efficiency and lifetime.

The inventive compound represented by Formula (2) has a stronger mobility and an excellent packing density in the case of the device measurement as compared with Comparative Compound 1, and the inventive compound represented by Formula (1) has a higher LUMO and a wider band gab and is excellent in electron blocking ability as compared with Comparative Compound 2. Therefore, it is considered that the combination of the two makes the hole and the electron charge balance and emits light inside the emitting layer rather than the interface of the hole transport layer, thereby lowering the driving voltage and maximizing the efficiency and lifetime.

That is, it is considered that the combination of Formula (1) and Formula (2) performs electrochemical synergistic action, thereby improving the performance of the entire device.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

What is claimed is:

1. An organic electric element comprising a first electrode, a second electrode, and an organic material layer formed between the first electrode and the second electrode,
wherein the organic material layer forms a hole transport layer between the first electrode and the emitting layer, and includes an electron blocking layer between the hole transport layer and the emitting layer,
wherein the electron blocking layer comprises a compound represented by Formula (1), and wherein the hole transport layer comprises a compound represented by Formula (2):

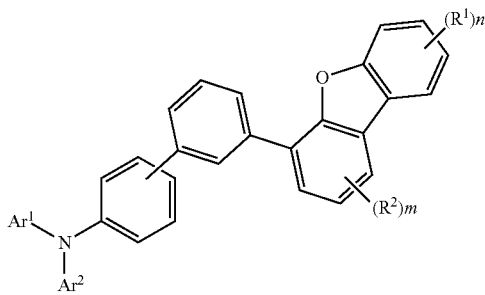

Formula (1)

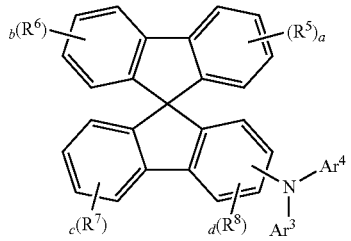

Formula (2)

in Formula (1) to (2), 1) n is an integer of 0 to 4, and m is an integer of 0 to 3,
2) $R^1$ and $R^2$ are each independently selected from the group consisting of a deuterium; a halogen; a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$)(where, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and the $R_a$ and $R_b$ may be independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P), or in case m and n are each 2 or more a plurality of $R^1$ or a plurality of $R^2$, each same or different, may be bonded to each other to form a ring, 3) $Ar^1$ and $Ar^2$ are each independently a $C_{12}$-$C_{20}$ aryl group unsubstituted or substituted with deuterium, 4) a, b, and c are each independently integer of 0 to 4, and d is an integer of 0 to 3, 5) $R^5$, $R^6$, $R^7$ and $R^8$ are each independently selected from the group consisting of a deuterium; a halogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or in case a, b, c, d, e and f are each 2 or more, a plurality of $R^5$ or a plurality of $R^6$ or a plurality of $R^7$ or a plurality of $R^8$, each same or different, may be bonded to each other to form a ring, 6) $Ar^3$ and $Ar^4$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring;

in Formula (2), the aryl group, the fluorenyl group, the heterocyclic group, the fused ring group, the alkyl group, the alkenyl group, the alkynyl group, the alkoxyl group and the aryloxy group may be each independently substituted with one or more substituents selected from a group consisting of a deuterium; halogen; a silane group; a siloxane group; a boron group; a germanium group; a cyano; a nitro group; -L'-N($R_a$)($R_b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, and also, these substituents may combine each other and form a ring, wherein the term 'ring' means $C_3$-$C_{60}$ aliphatic ring or $C_6$-$C_{60}$ aromatic ring or a $C_2$-$C_{60}$ heterocyclic ring or a fused ring formed by the combination of them, and includes a saturated or unsaturated ring.

2. The organic electric element of claim 1, wherein the compound represented by Formula (1) of the electron blocking layer is represented by any one of the following Formulas (3) to (5):

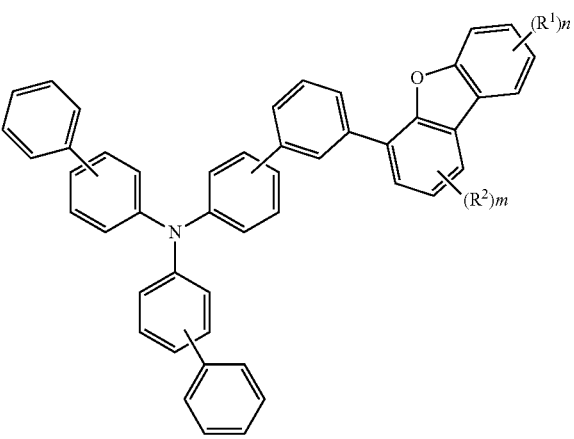

<Formula (3)>

-continued

<Formula (4)>

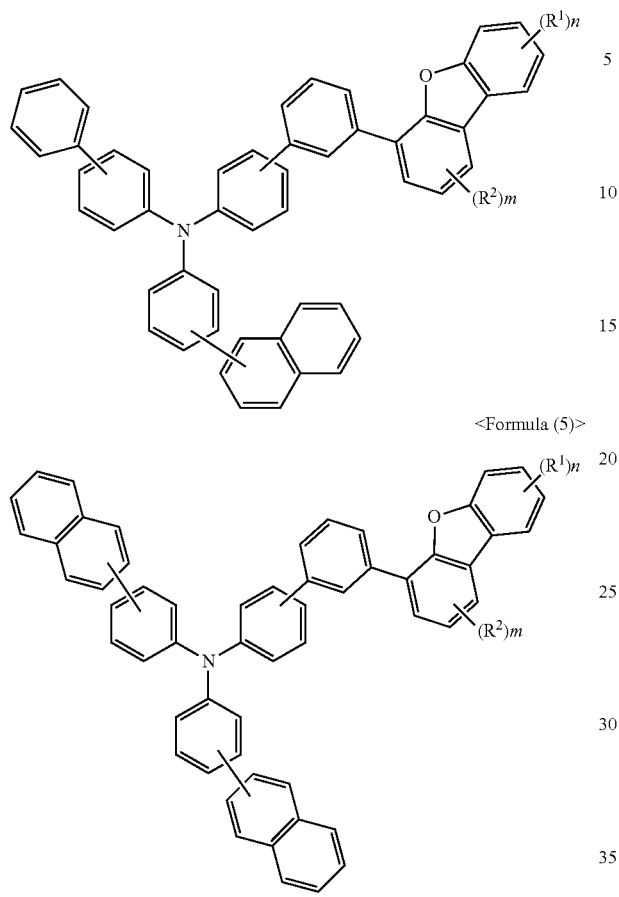

<Formula (5)>

<Formula (8)>

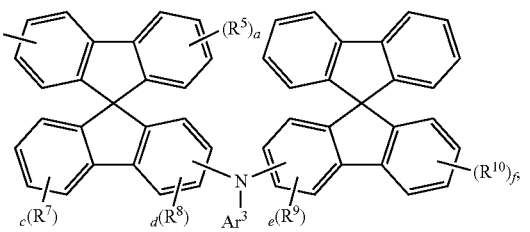

wherein
1) $R^5, R^6, R^7, R^8$, a, b, c, d and $Ar^3$ are the same as defined in the claim 1,
2) f is an integer of 0 to 4, and e is an integer of 0 to 3,
3) $R^9$ and $R^{10}$ are each independently selected from the group consisting of a deuterium; halogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$), or in case e and f are 2 or more, a plurality of $R^9$ or a plurality of $R^{10}$, each same or different, may be bonded to each other to form a ring.

4. The organic electric element of claim 1, wherein the compound represented by Formula (1) in the electron blocking layer comprises any one of the following compounds 1-1 to 3-12;

in Formula (3) to (5), $R^1$, $R^2$, m and n are the same as defined in the claim 1.

3. The organic electric element of claim 1, wherein a compound represented by Formula (2) of the hole transport layer is represented by any one of the following Formulas (6) to (8):

<Formula (6)>

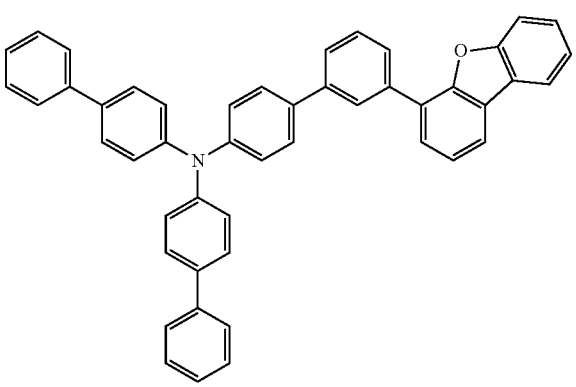

<Formula (7)>

1-1

1-2

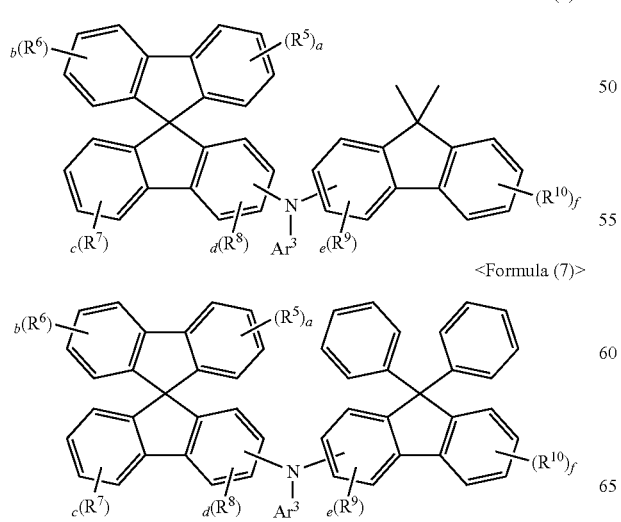

1-3
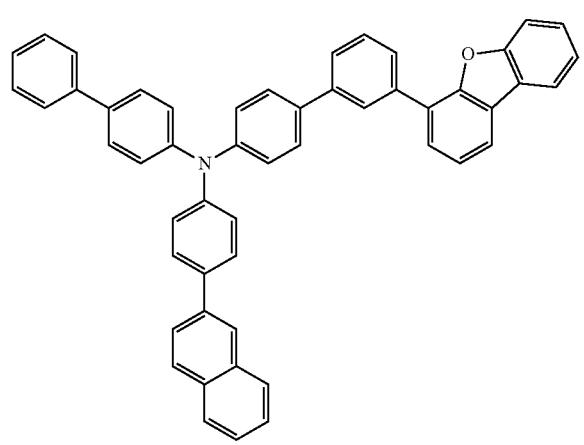
1-4
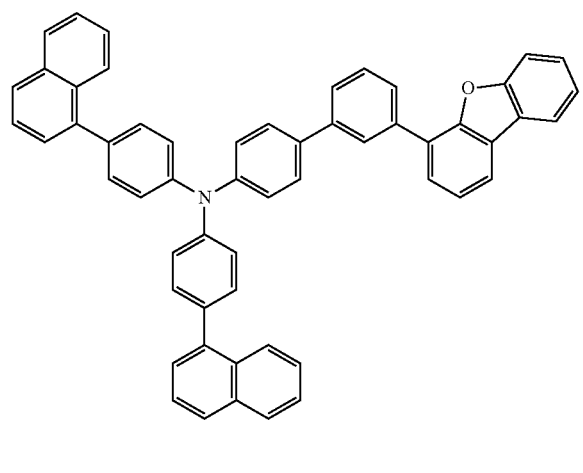
1-5
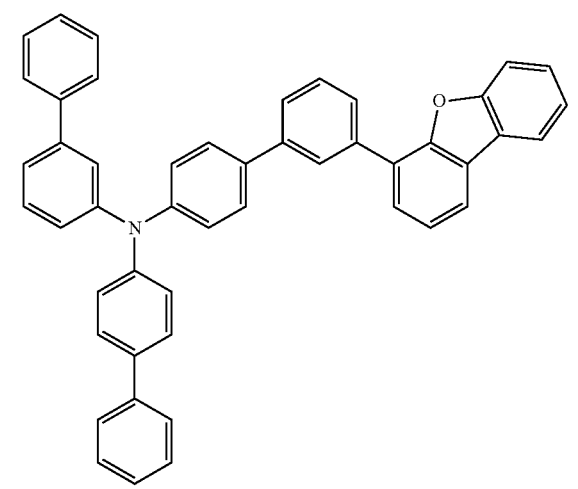
1-6
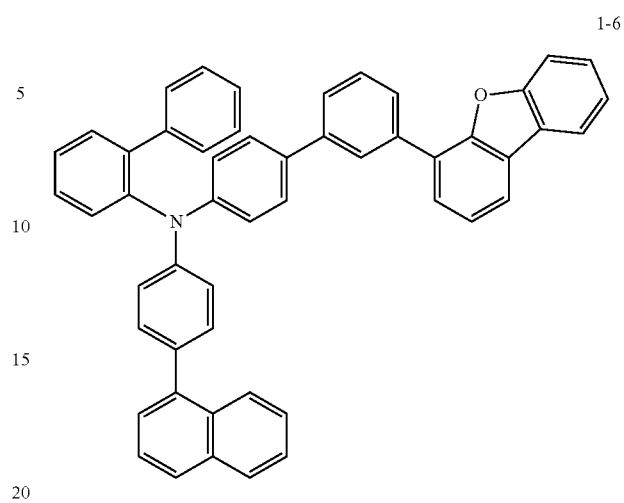
1-7
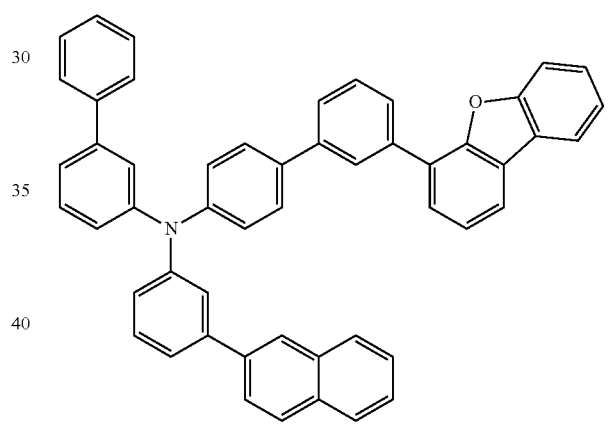
1-8
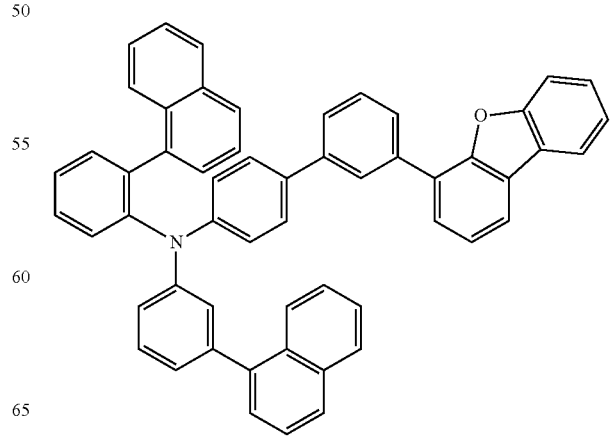

1-9
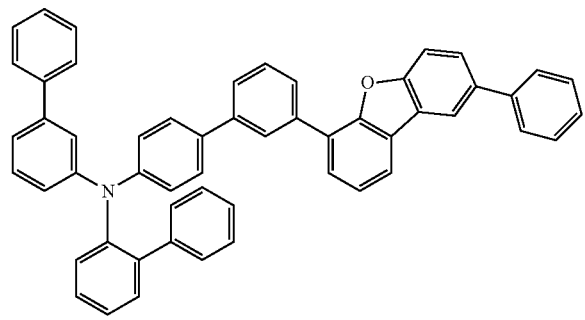
1-10
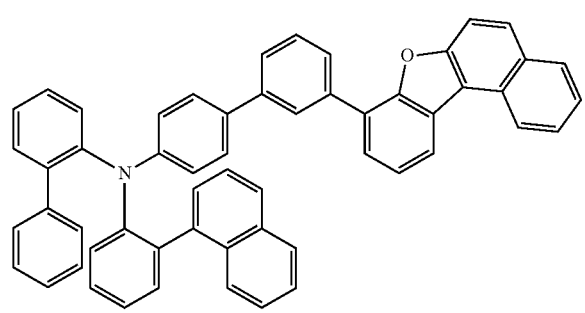
1-11
1-12
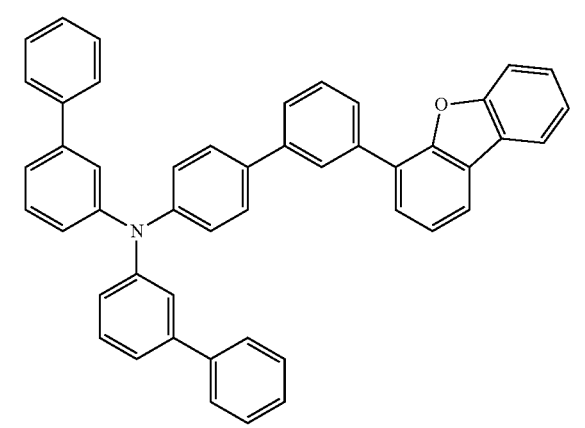
2-1
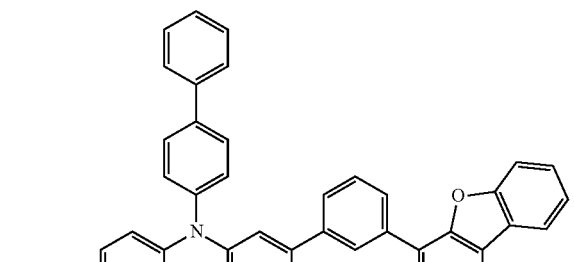
2-2
2-3
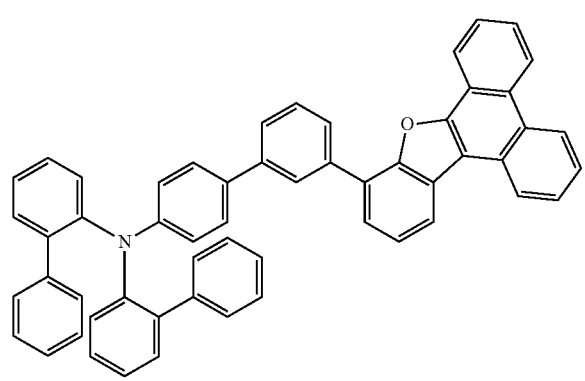
2-4
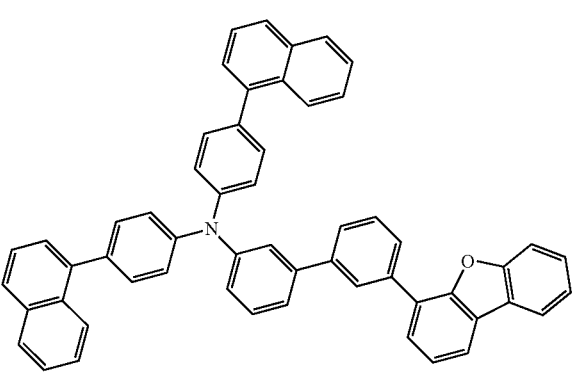

2-5
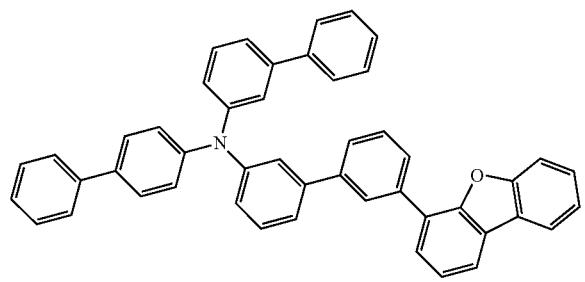
2-8
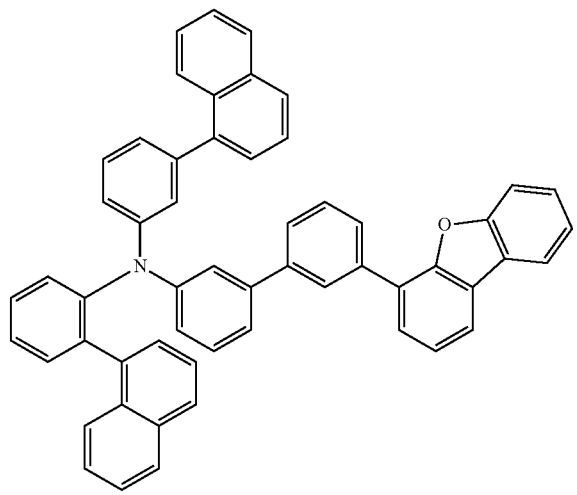
2-6
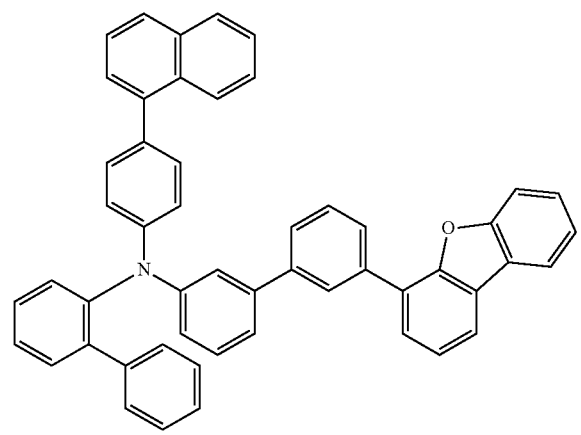
2-9
2-10
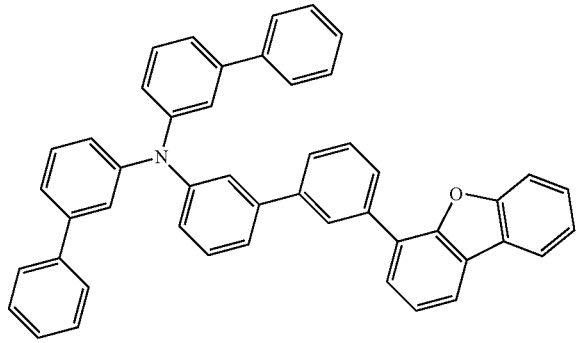
2-7
2-11
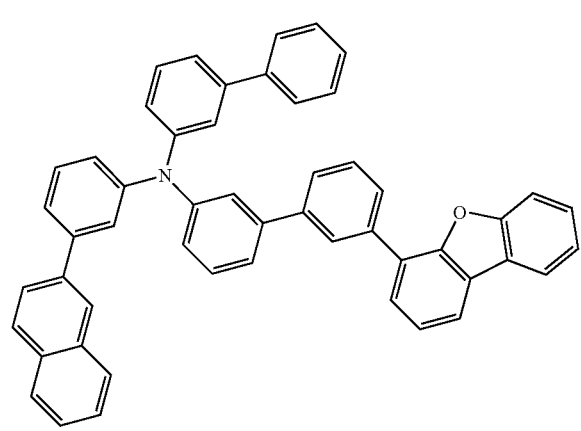

2-12
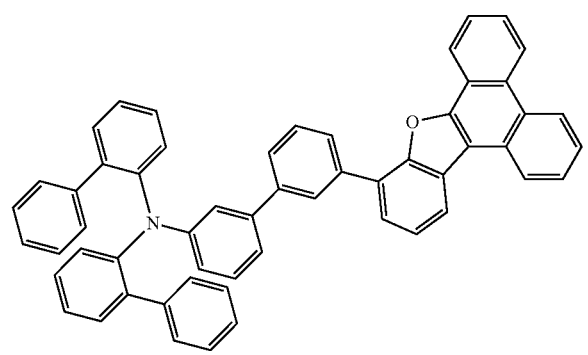
3-1
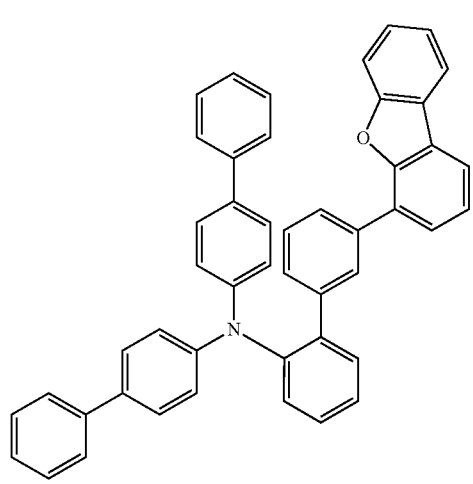
3-2
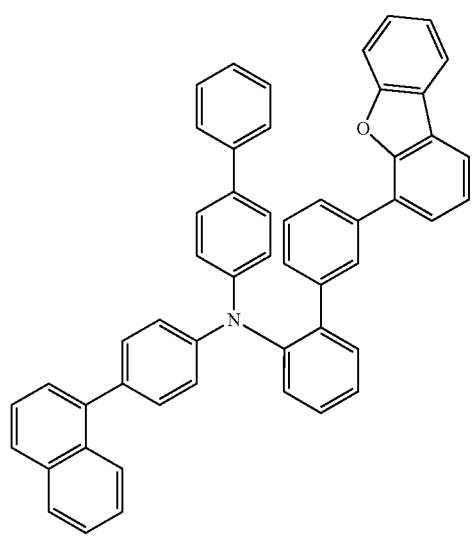
3-3
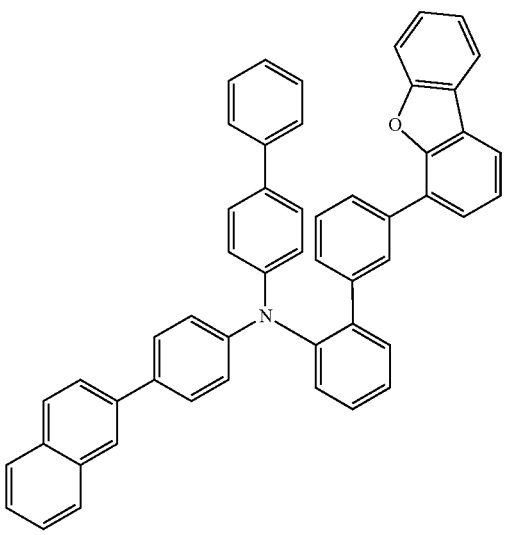
3-4
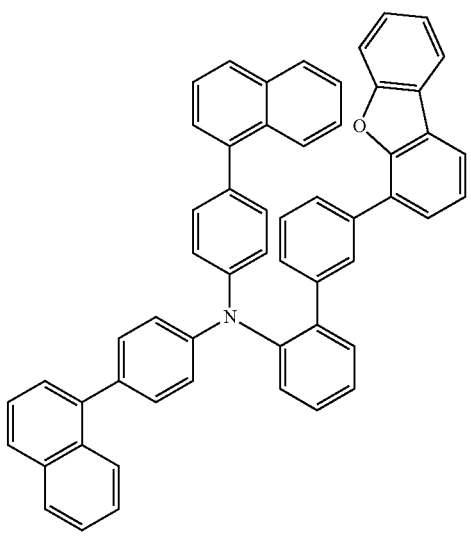
3-5
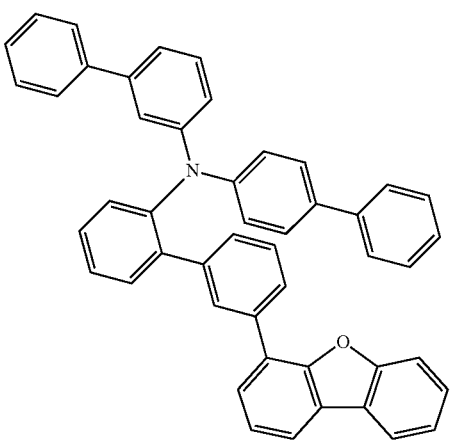

-continued
3-6
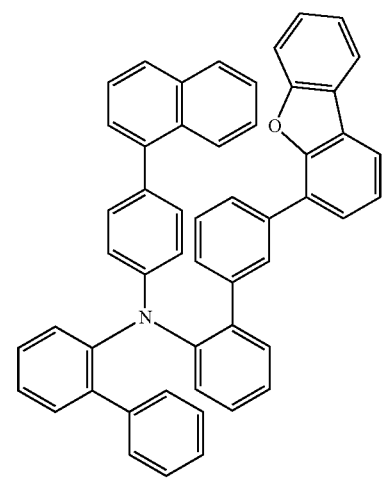
3-7
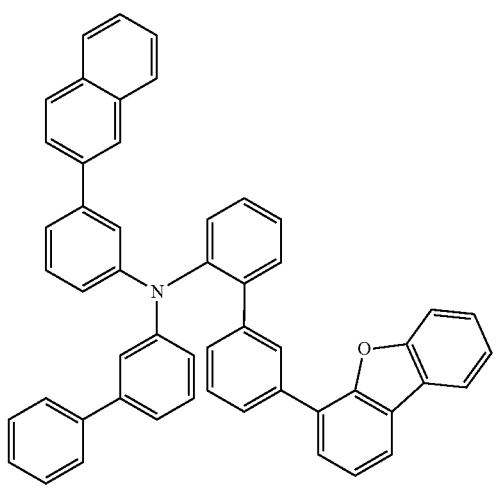
3-8
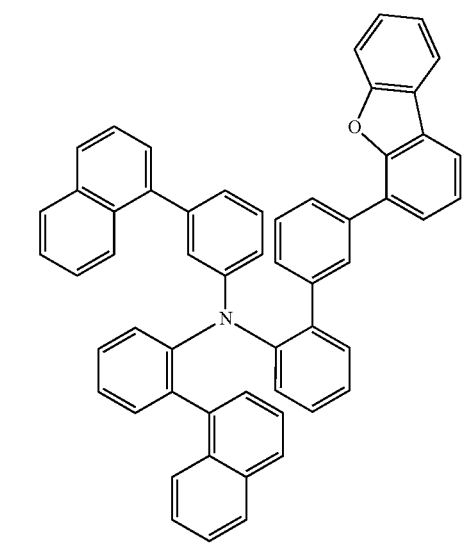
3-9
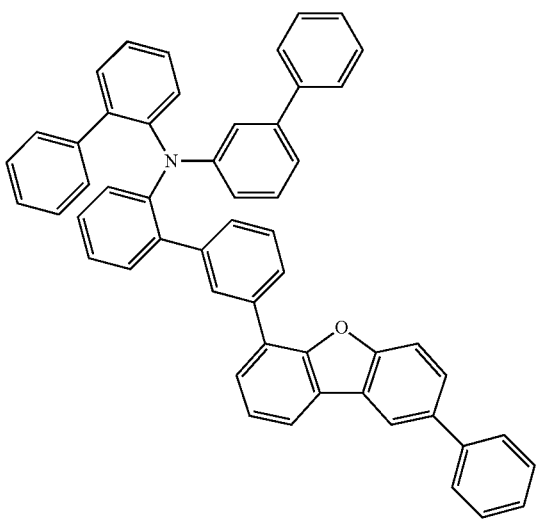
3-10
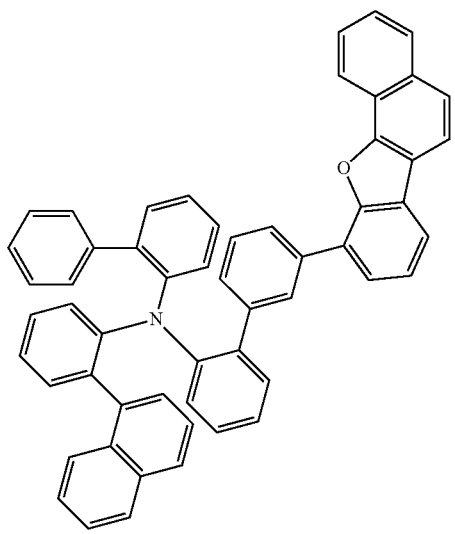
3-11
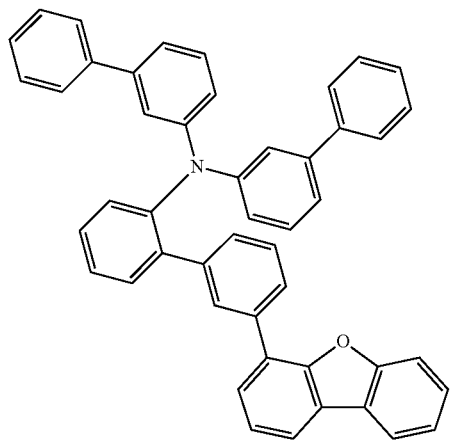

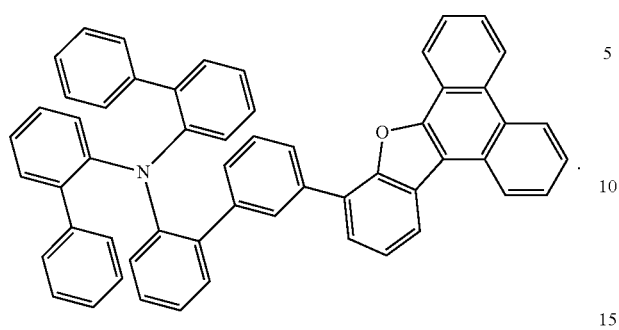
3-12
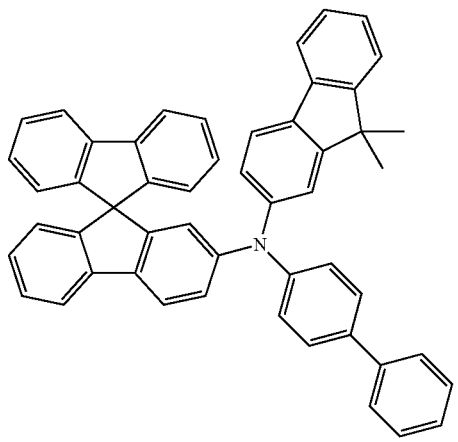
4-4
5. The organic electric element of claim 1, wherein the compound represented by Formula (2) in the hole transport layer comprises any one of the following compounds 4-1 to 4-36:
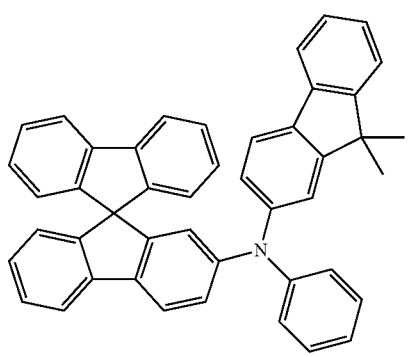
4-1
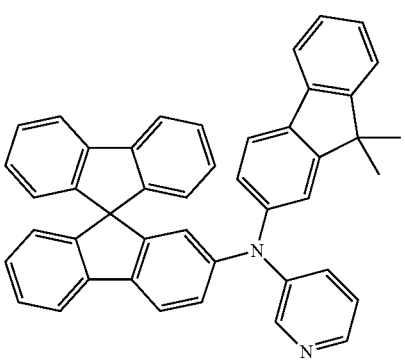
4-5
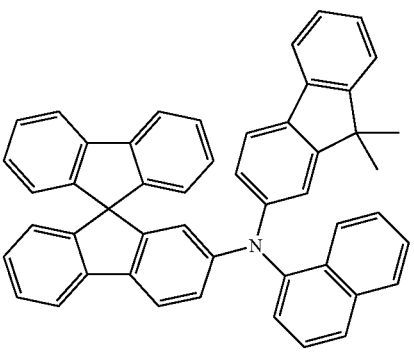
4-2
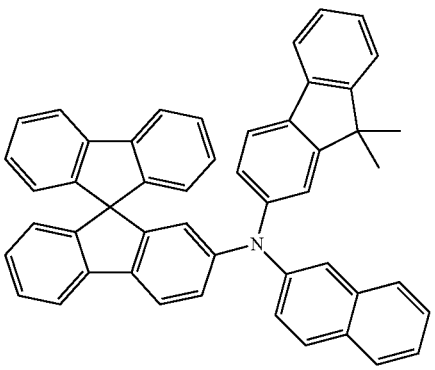
4-3
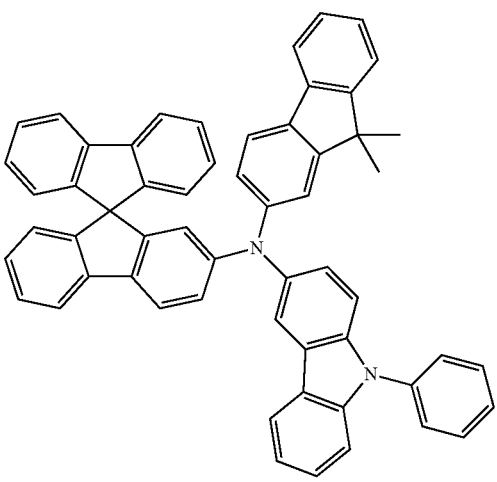
4-6

4-7
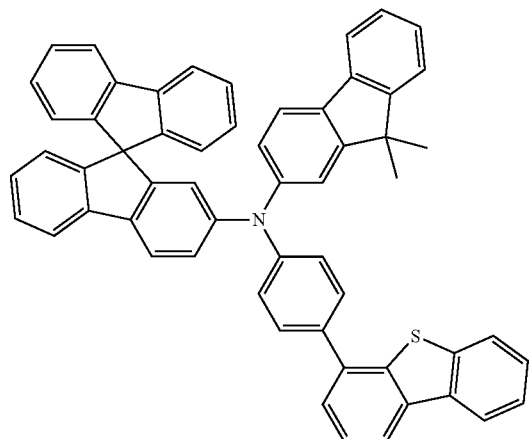
4-8
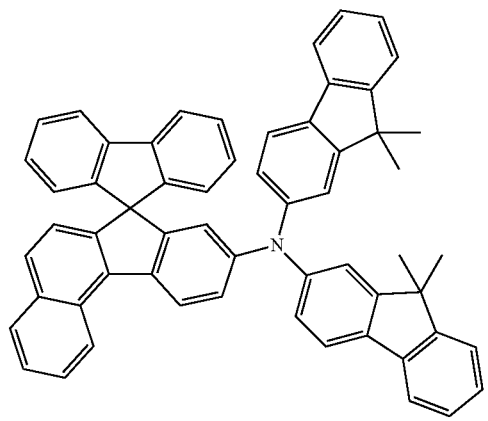
4-9
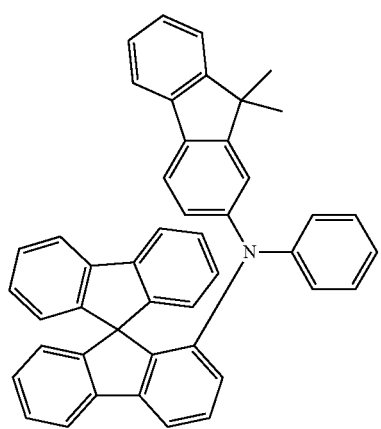
4-10
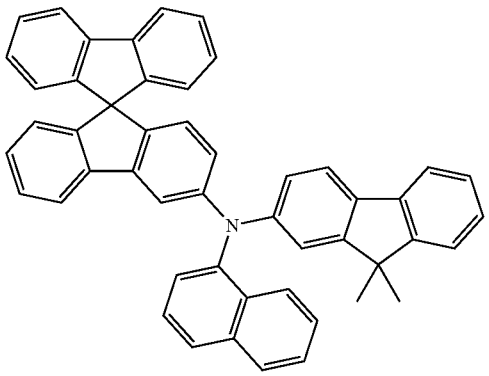
4-11
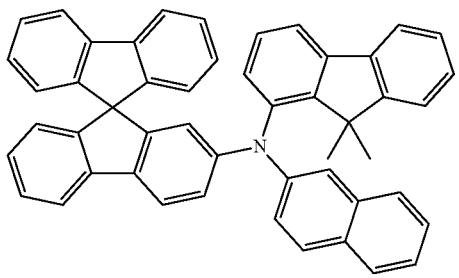
4-12
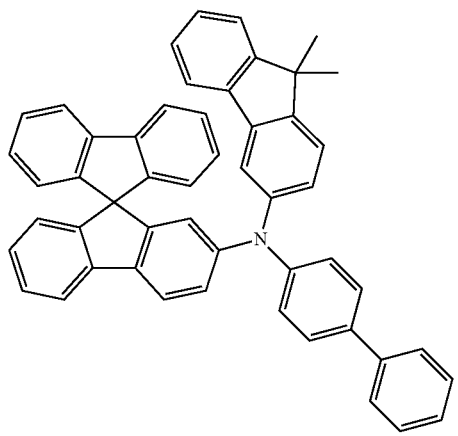
4-13
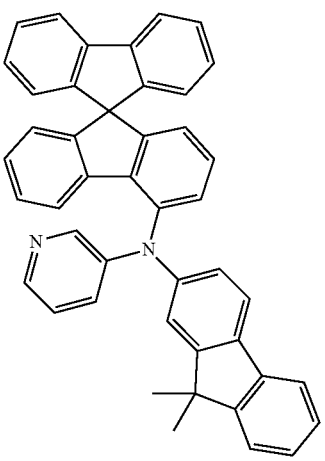

4-14
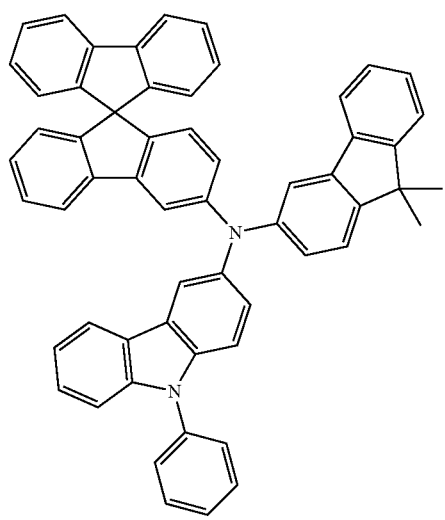
4-15
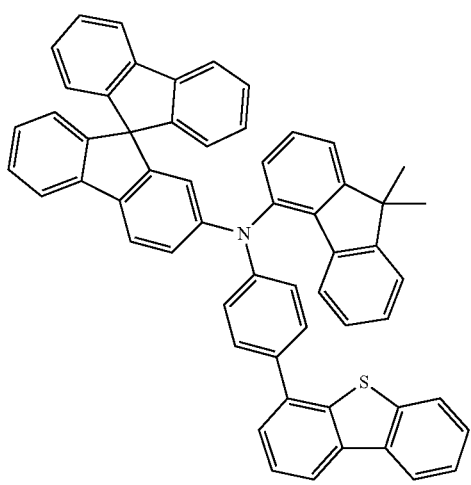
4-16
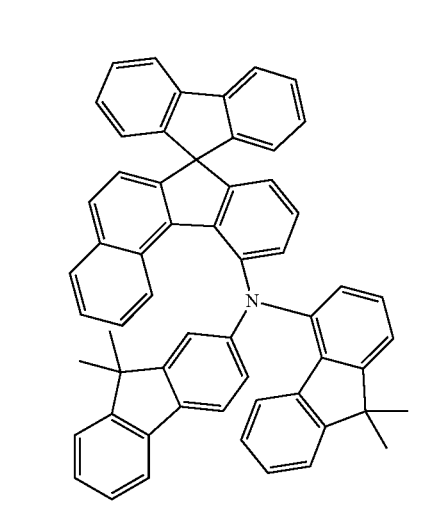
4-17
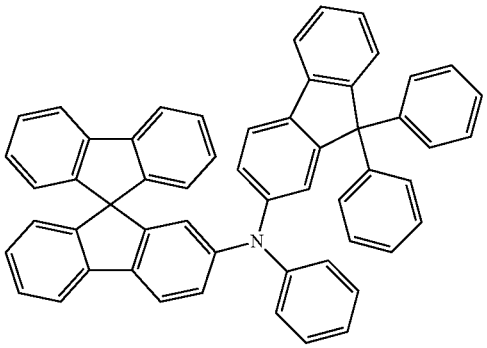
4-18
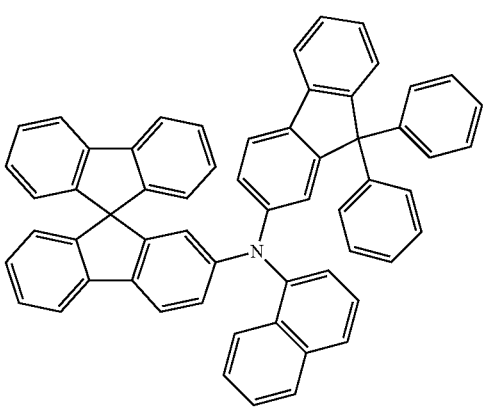
4-19
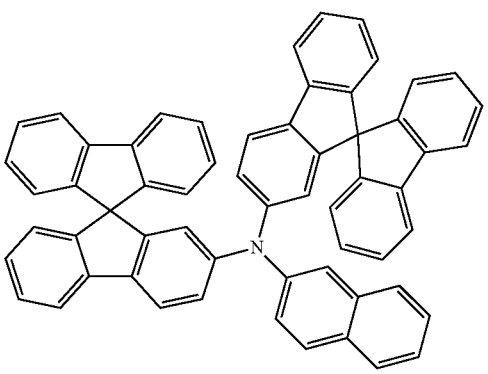
4-20
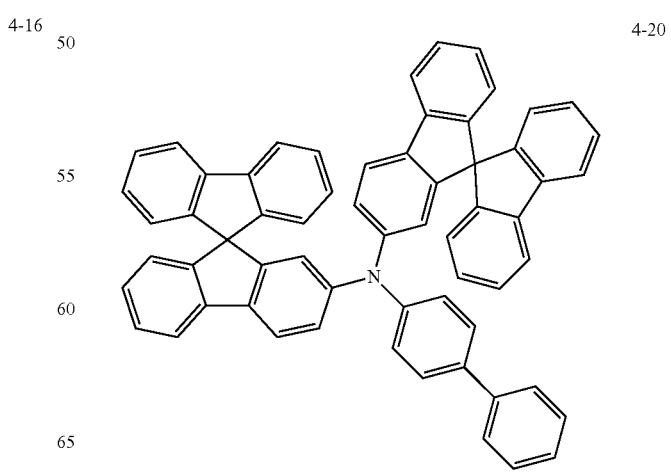

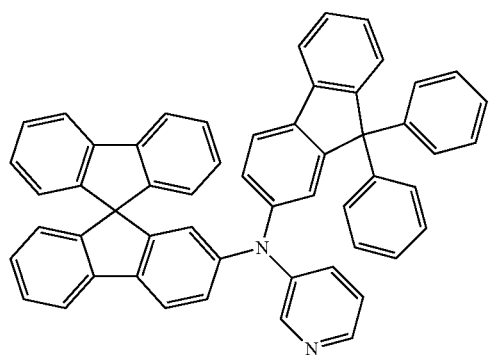
4-21
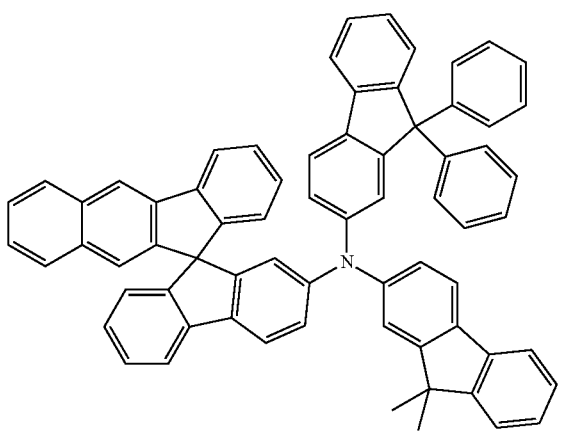
4-24
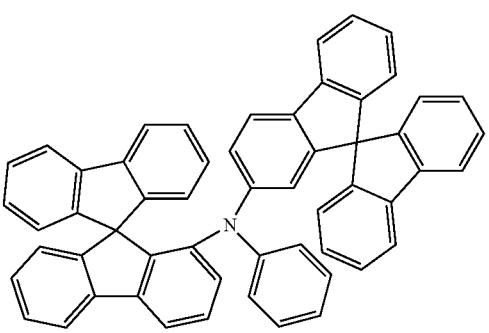
4-25
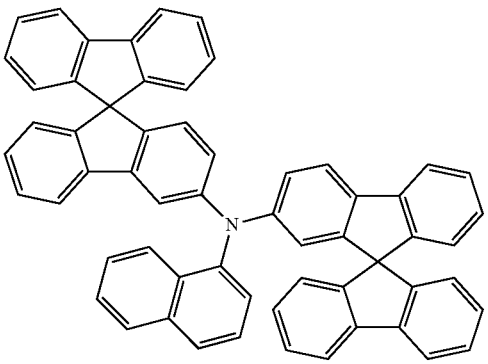
4-26
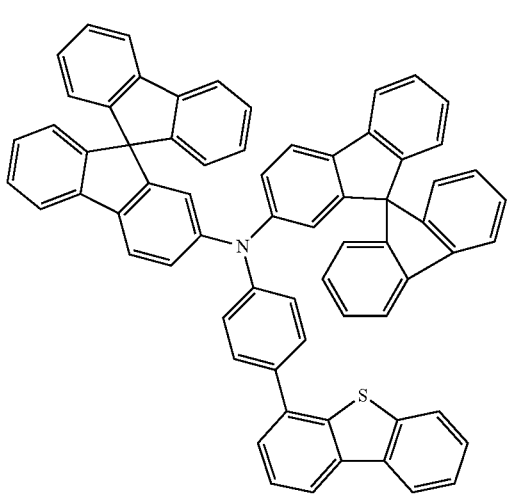
4-23
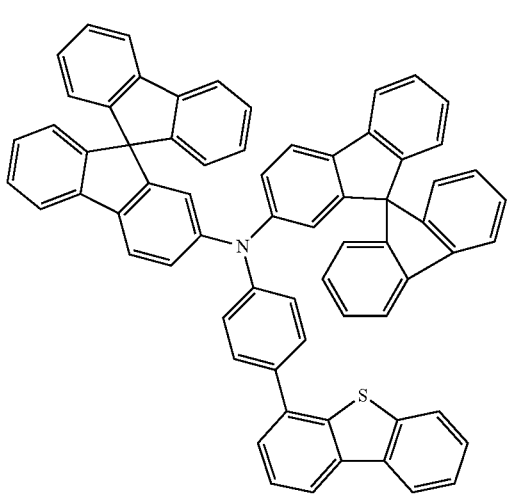
4-27

4-28
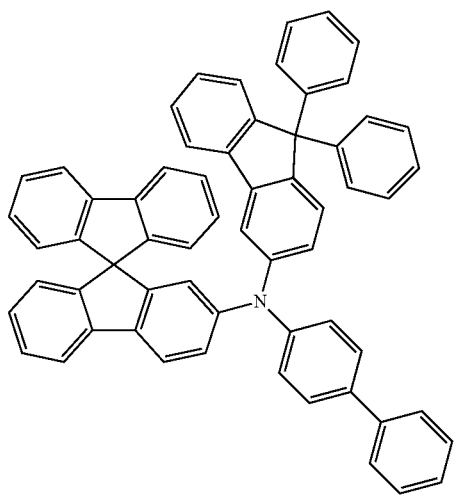
4-31
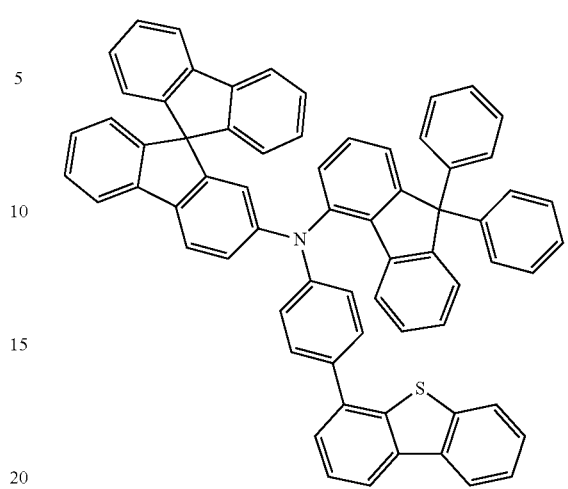
4-29
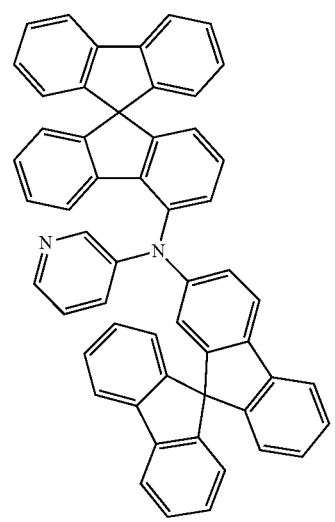
4-32
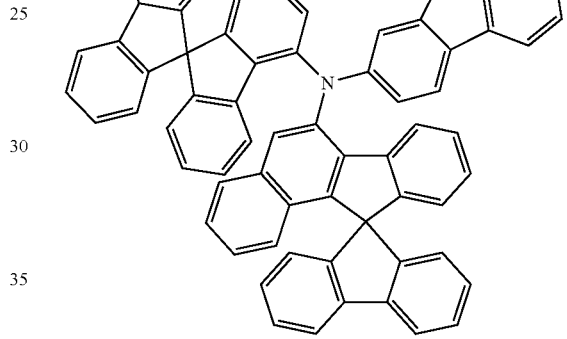
4-33
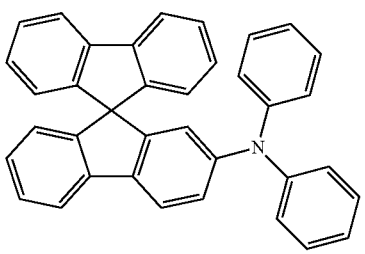
4-30
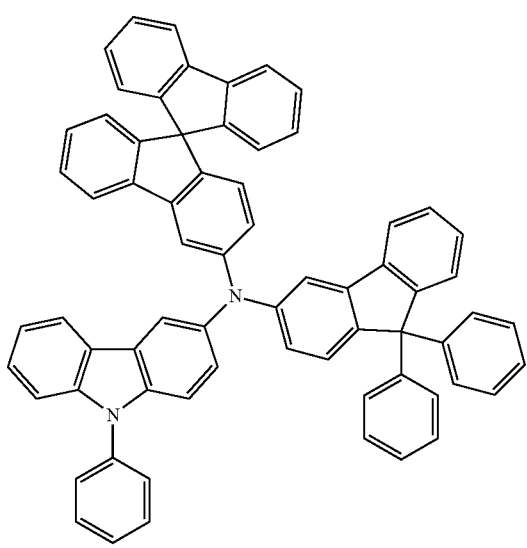
4-34
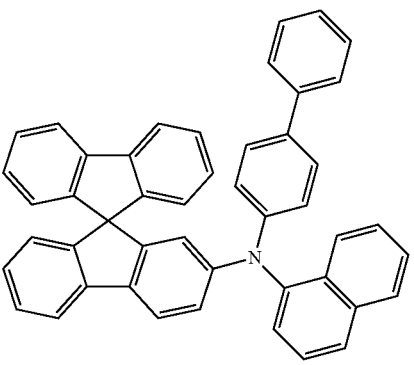

4-35

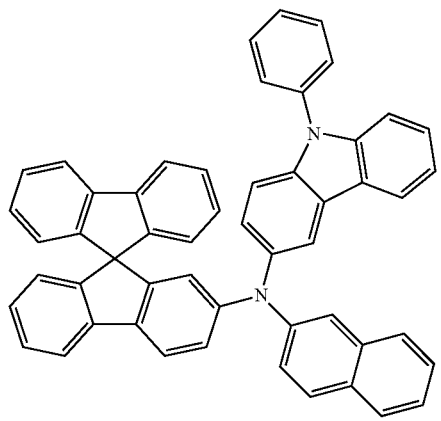

4-36

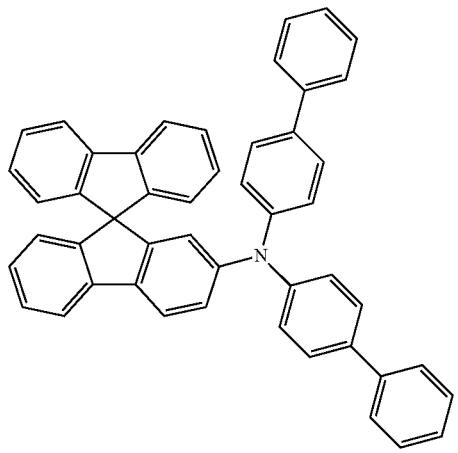

6. The organic electric element of claim 2, wherein the hole transport layer comprises a compound represented by any one of Formulas (6) to (8):

<Formula (6)>

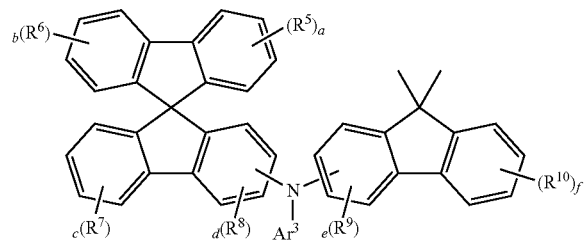

<Formula (7)>

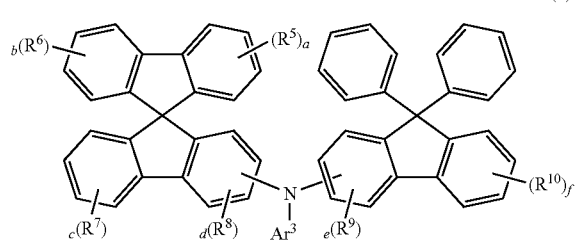

<Formula (8)>

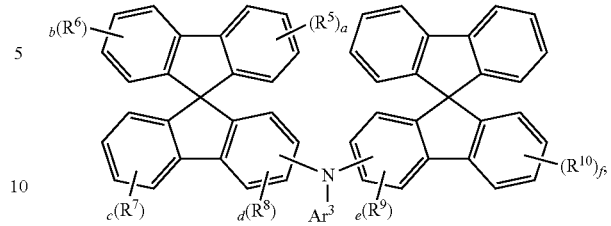

in Formulas (6) to (8), $R^5$, $R^6$, $R^7$, $R^8$, a, b, c, d and $Ar^3$ are the same as defined in claim 2.

7. The organic electric element of claim 4, wherein the hole transport layer comprises any one of compounds represented by Formulas (6) to (8):

<Formula (6)>

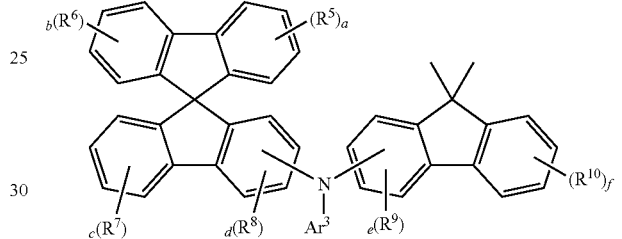

<Formula (7)>

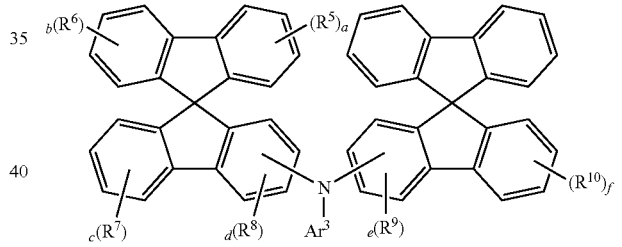

<Formula (8)>

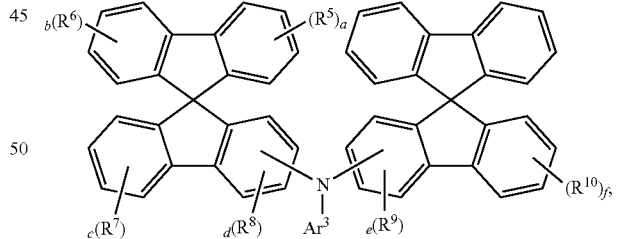

wherein:

1) $Ar^3$ is selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring;

2) $R^5$, $R^6$, $R^7$ and $R^8$ are each independently selected from the group consisting of a deuterium; a halogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or in case a, b, c, d, e and f are each 2 or more, a plurality of $R^5$ or a plurality of $R^6$ or a plurality of $R^7$ or a plurality of $R^8$, each same or different, may be bonded to each other to form a ring, 3) a, b, and c are each independently integer of 0 to 4, and d is an integer of 0 to 3, 4) $R^9$ and $R^{10}$ are each independently selected from the group consisting of a deuterium; halogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$), or in case e and f are 2 or more, a plurality of $R^9$ or a plurality of $R^{10}$, each same or different, may be bonded to each other to form a ring 5) f is an integer of 0 to 4, and e is an integer of 0 to 3.

8. The organic electric element of claim 4, wherein the hole transport layer comprises any one of compounds represented by Formulas 4-1 to 4-36:

4-1

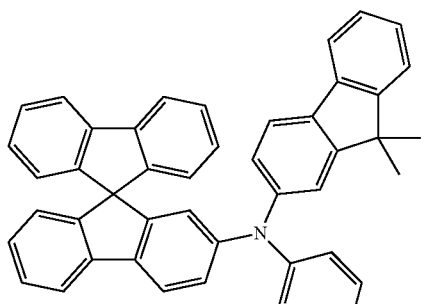

4-2

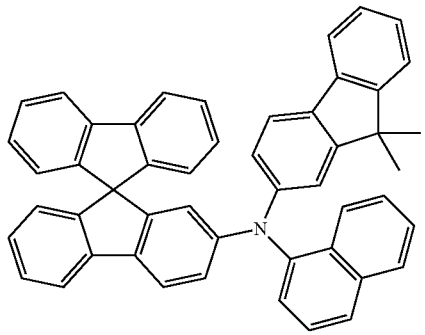

4-3

4-4

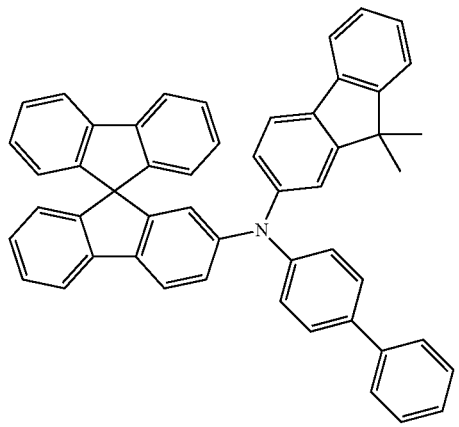

4-5

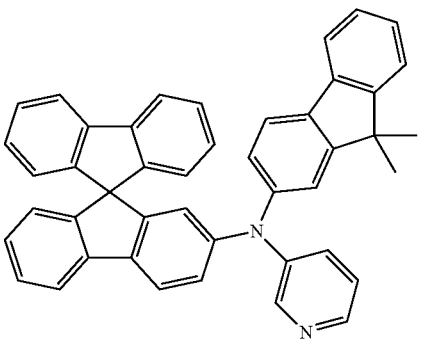

4-6

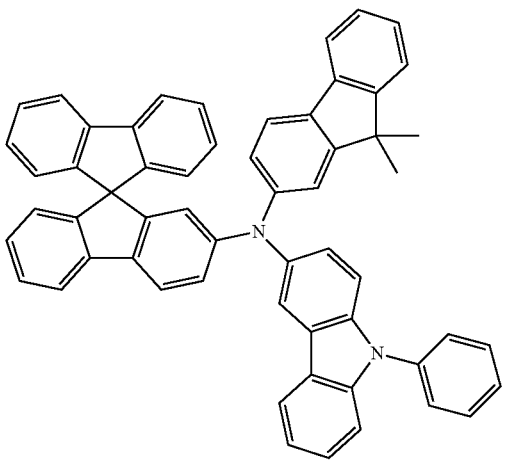

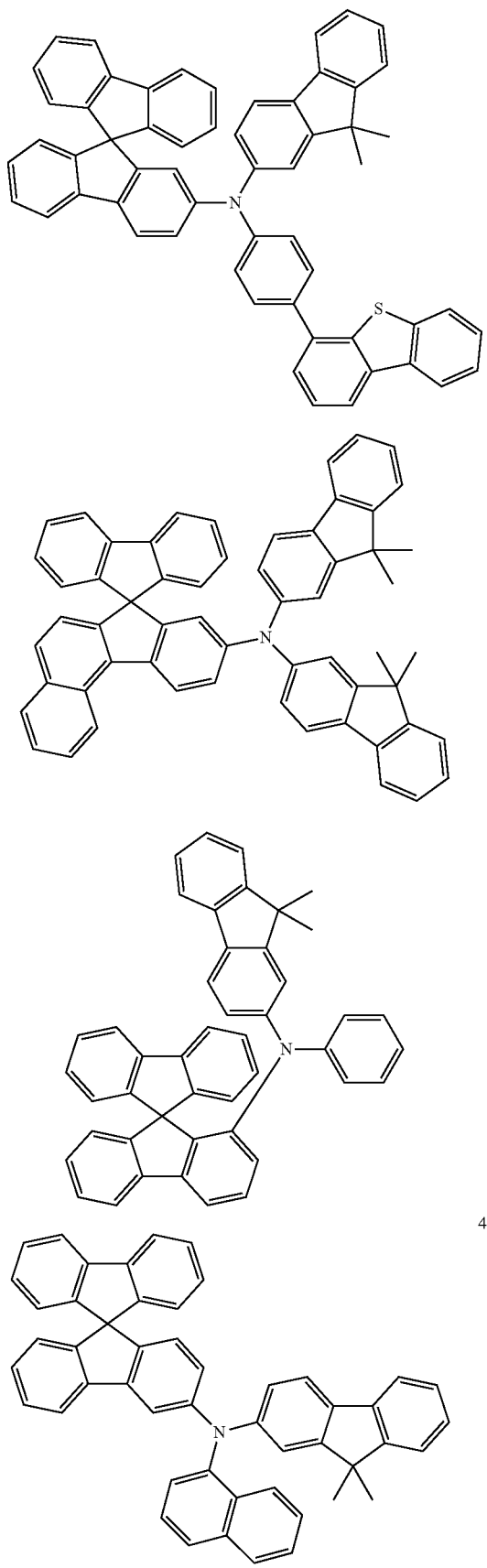
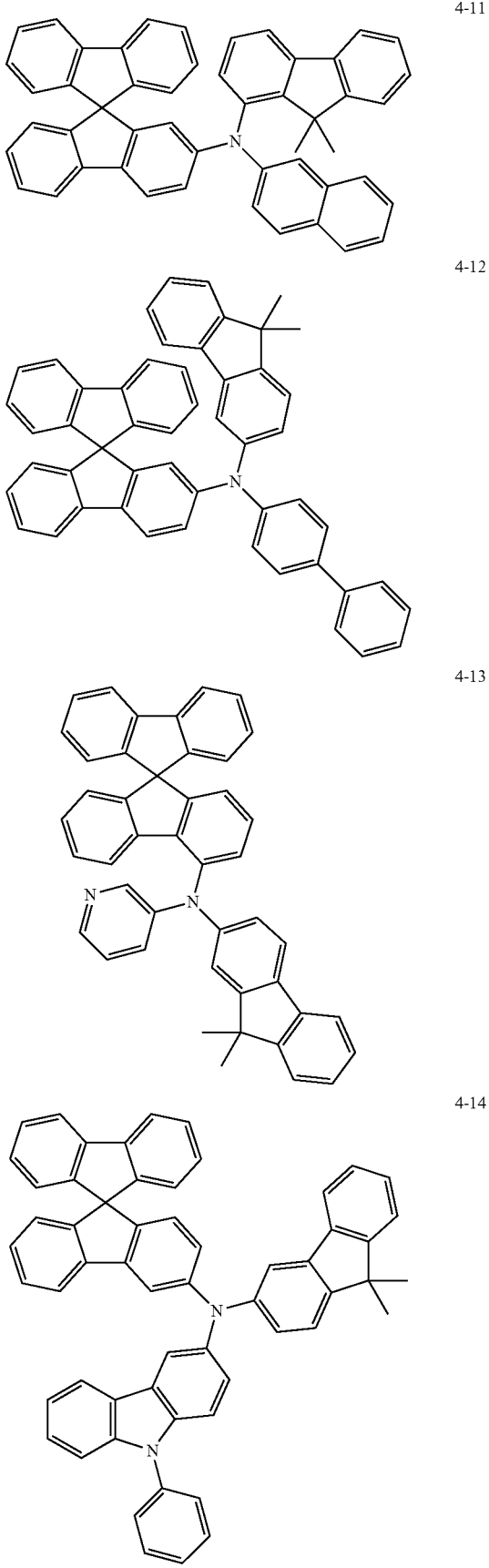

4-15
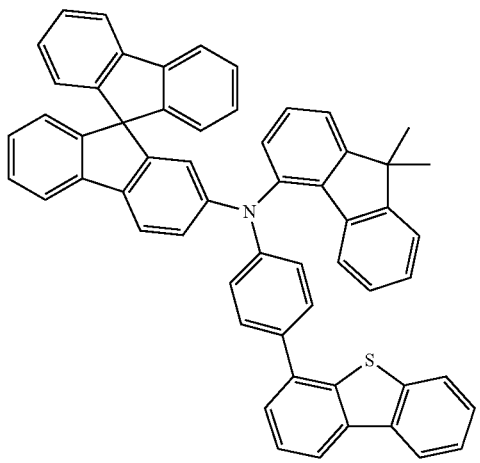
4-16
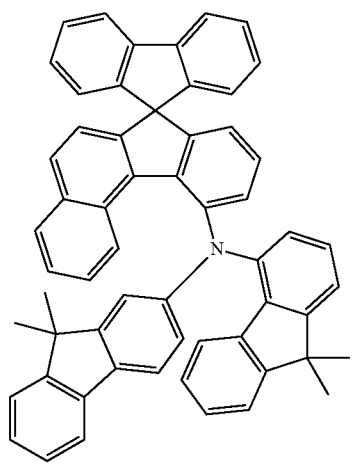
4-17
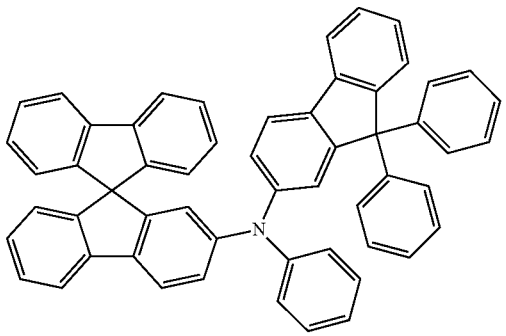
4-18
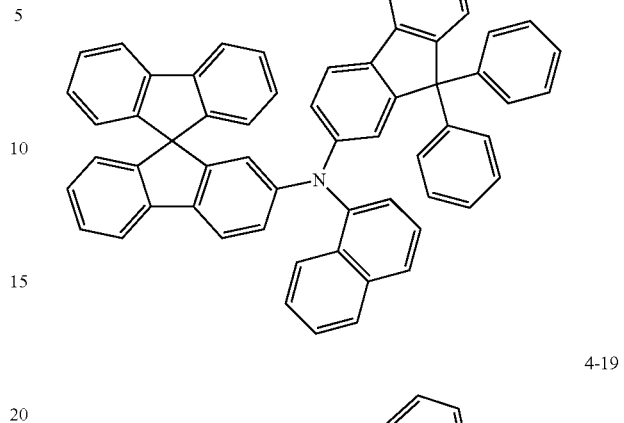
4-19
4-20
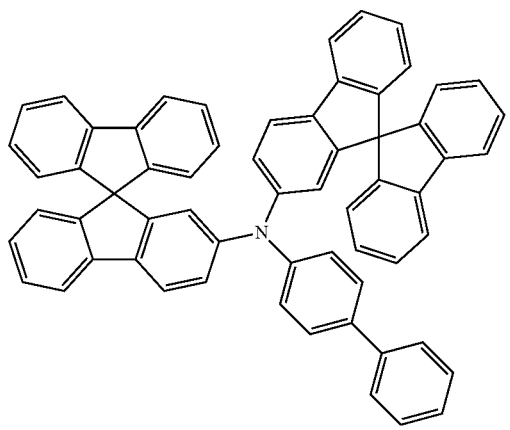
4-21
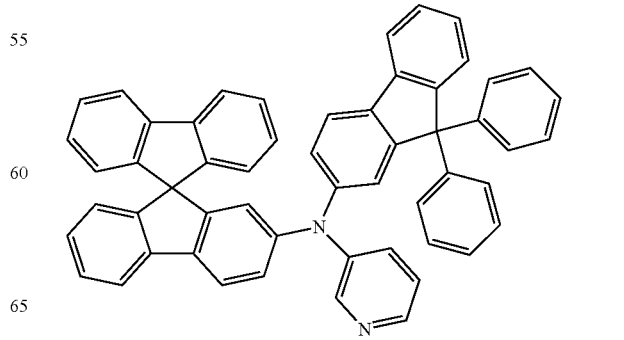

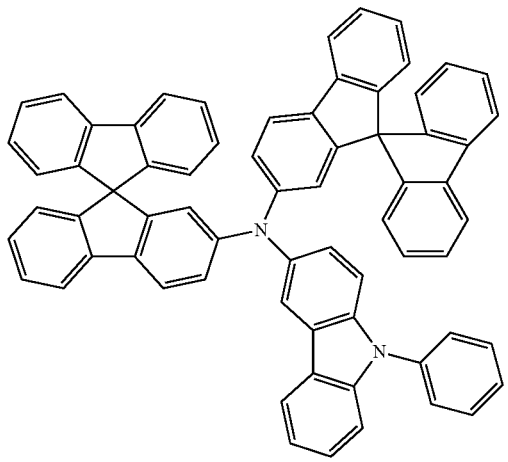
4-22
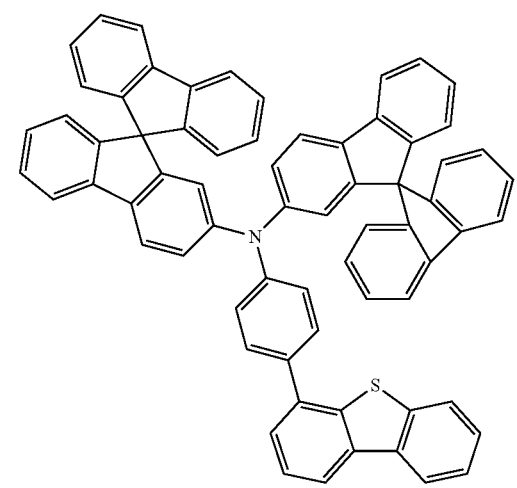
4-23
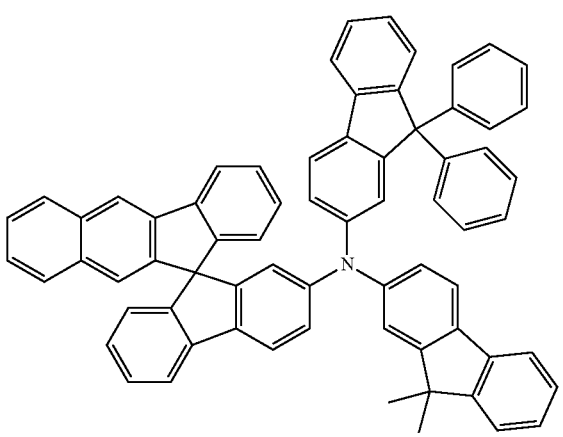
4-24
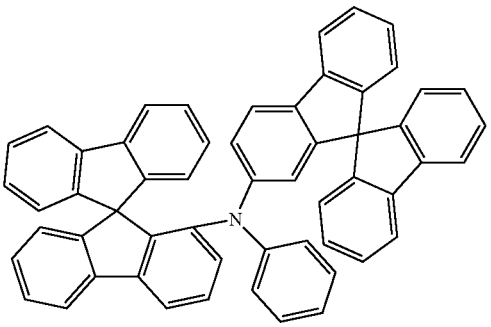
4-25
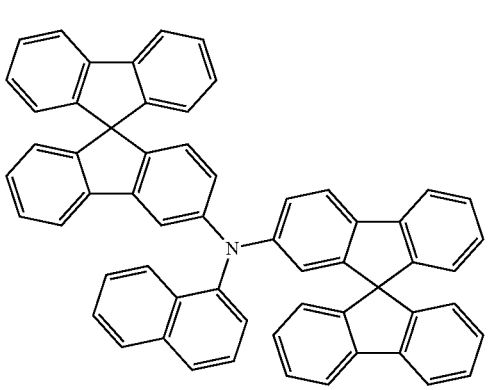
4-26
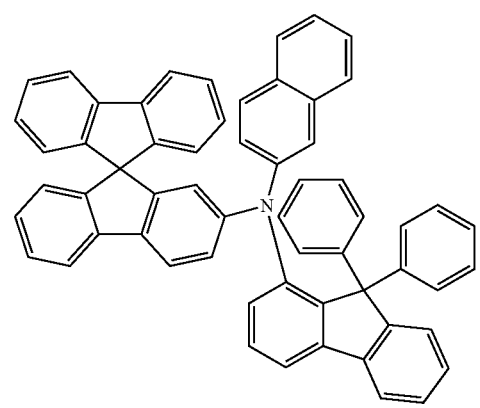
4-27
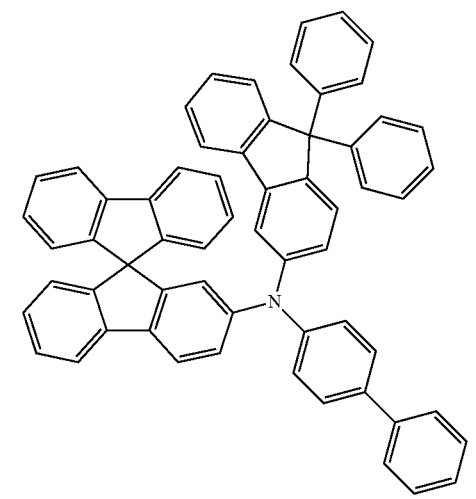
4-28

4-29
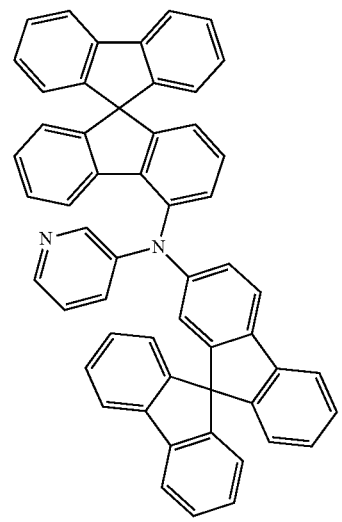
4-30
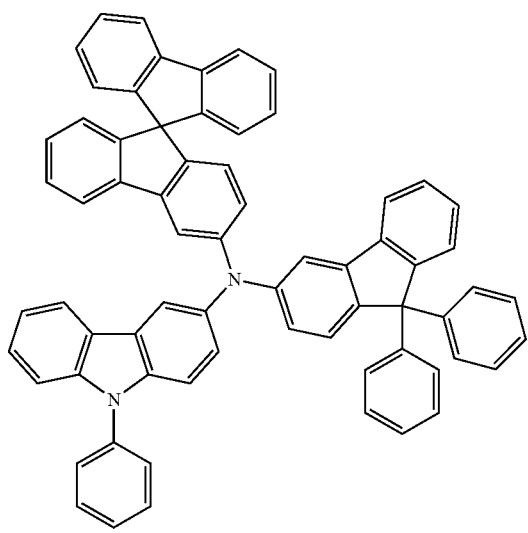
4-31
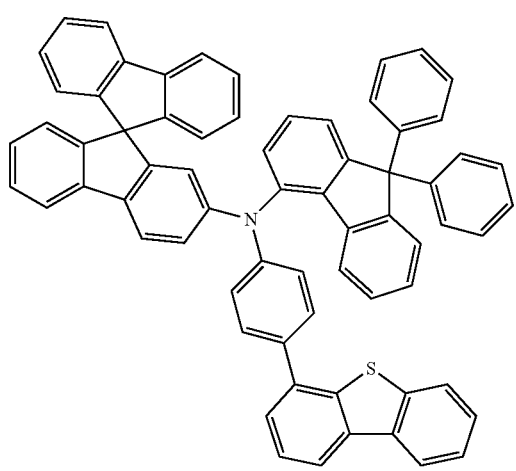
4-32
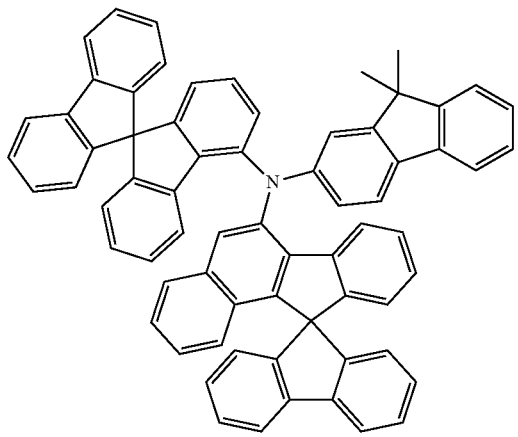
4-33
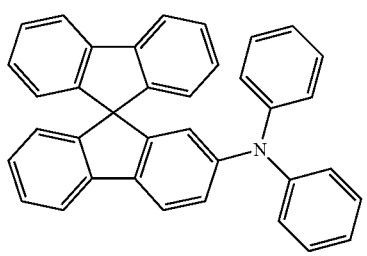
4-34
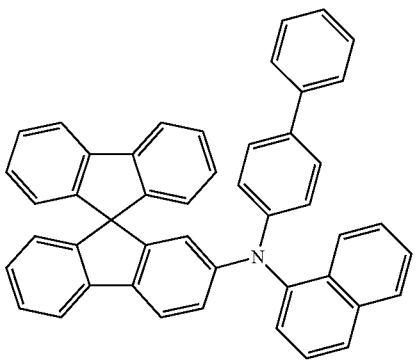
4-35
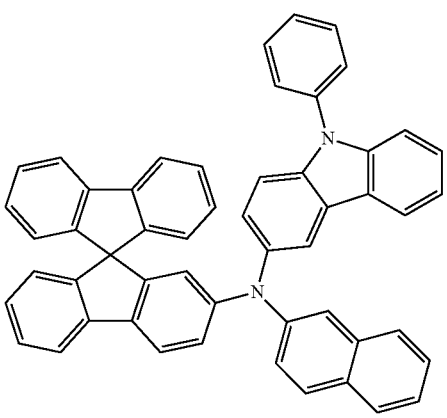

-continued 4-36

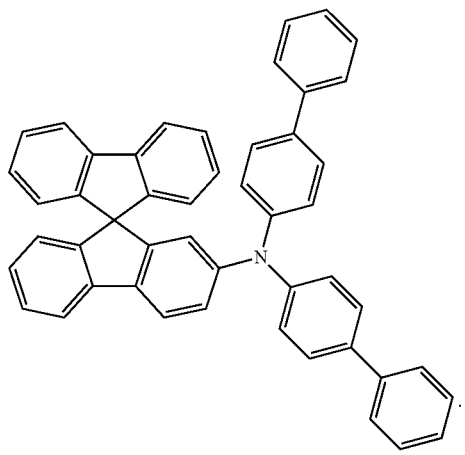

9. The organic electric element of claim 1, wherein the electron blocking layer comprises a composition in which two or more compounds having different structures among the compounds represented by the formula (1) are mixed.

10. The organic electric element of claim 1, wherein the hole transport layer comprises a composition in which two or more compounds having different structures among the compounds represented by the formula (2) are mixed.

11. The organic electric element of claim 1, further comprising a light efficiency enhancing layer formed on at least one side opposite to the organic material layer among one side of the first electrode and the second electrode.

12. The organic electric element of claim 1, wherein the organic material layer is formed by a spin coating process, a nozzle printing process, an inkjet printing process, a slot coating process, a dip coating process or a roll-to-roll process.

13. An electronic device comprising a display device comprising the organic electric element of claim 1; and a control part driving the display device.

14. The electronic device of claim 11, wherein the organic electric element is one of an OLED, an organic solar cell, an organic photo conductor(OPC), Organic transistor(organic TFT) and an element for monochromic or white illumination.

* * * * *